US012270015B2

(12) United States Patent
Tamayol et al.

(10) Patent No.: US 12,270,015 B2
(45) Date of Patent: Apr. 8, 2025

(54) BIOPRINTER DEVICES, SYSTEMS AND METHODS FOR PRINTING SOFT GELS FOR THE TREATMENT OF MUSCULOSKELETAL AND SKIN DISORDERS

(71) Applicant: NUtech Ventures, Lincoln, NE (US)

(72) Inventors: Ali Tamayol, Lincoln, NE (US); Azadeh Mostafavi, Lincoln, NE (US); Carina Russell, Lincoln, NE (US); Tyrell Williams, Lincoln, NE (US); Indranil Sinha, Boston, MA (US); Jacob Quint, Lincoln, NE (US)

(*) Notice: Subject to any disclaimer, the term of this patent is extended or adjusted under 35 U.S.C. 154(b) by 1530 days.

(21) Appl. No.: 16/659,326

(22) Filed: Oct. 21, 2019

(65) Prior Publication Data
US 2020/0123485 A1 Apr. 23, 2020

Related U.S. Application Data

(60) Provisional application No. 62/748,124, filed on Oct. 19, 2018.

(51) Int. Cl.
C12M 3/00 (2006.01)
A61F 2/00 (2006.01)
(Continued)

(52) U.S. Cl.
CPC .......... *C12M 21/08* (2013.01); *A61F 2/0063* (2013.01); *A61M 5/178* (2013.01); *C12M 33/00* (2013.01);
(Continued)

(58) Field of Classification Search
CPC ...... A61F 2/0063; A61M 5/178; C12M 33/00
See application file for complete search history.

(56) References Cited

U.S. PATENT DOCUMENTS 8,603,028 B2 * 12/2013 Mudd ............... A61M 5/19
604/82
8,821,434 B2 * 9/2014 Hunter ............. A61M 5/30
604/59
(Continued)

OTHER PUBLICATIONS

B. Corona et al., "Inflammatory and Physiological Consequences of Debridement of Fibrous Tissue after Volumetric Muscle Loss Injury", *Clinical and Translational Science.*; 11(2):208-17. doi: doi:10.1111/cts.12519. (2018).
(Continued)

*Primary Examiner* — Julian W Woo
(74) *Attorney, Agent, or Firm* — Gerald T. Gray; Leydig, Voit, Mayer, LTD.

(57) ABSTRACT

Systems and methods are described that utilize bioprinters to form scaffold structures in situ to facilitate treatment of the musculoskeletal or skin disorders in patients. A method for treating a musculoskeletal disorder of a patient includes positioning a bioprinter at a situs of the musculoskeletal disorder, or a situs of a skin injury, in the patient. The method includes extruding a hydrogel formulation from the bioprinter into the situs. The method includes curing the hydrogel formulation in the situs. The hydrogel formulation has a composition effective to generate, upon the curing, a scaffold structure in the situs to facilitate muscle hypertrophy and/or new muscle fibers, or skin wound healing, in the situs.

14 Claims, 42 Drawing Sheets
(22 of 42 Drawing Sheet(s) Filed in Color)

(51) Int. Cl.
  *A61M 5/178* (2006.01)
  *C12M 1/26* (2006.01)
  *C12N 5/00* (2006.01)
  *B33Y 10/00* (2015.01)
  *B33Y 30/00* (2015.01)
  *B33Y 70/00* (2020.01)
  *B33Y 80/00* (2015.01)

(52) U.S. Cl.
  CPC ............ *C12N 5/0062* (2013.01); *B33Y 10/00* (2014.12); *B33Y 30/00* (2014.12); *B33Y 70/00* (2014.12); *B33Y 80/00* (2014.12)

(56) References Cited

U.S. PATENT DOCUMENTS

| | | | | |
|---|---|---|---|---|
| 11,203,151 | B2* | 12/2021 | Solorzano | C12N 5/0062 |
| 11,254,901 | B2* | 2/2022 | Langenfeld | C12M 1/26 |
| 11,400,183 | B2* | 8/2022 | Pang | A61L 27/3847 |
| 2015/0105891 | A1* | 4/2015 | Golway | G06F 30/00 |
| | | | | 700/98 |
| 2019/0232558 | A1* | 8/2019 | You | B29C 64/386 |

OTHER PUBLICATIONS

Beth E. Pollot et al. "Volumetric muscle loss" *Skeletal Muscle Regeneration in the Mouse: Springer*, p. 19-31. (2016).

Brian M. Sicari et al., "An acellular biologic scaffold promotes skeletal muscle formation in mice and humans with volumetric muscle loss", *Science translational medicine.* ; 6(234):234ra58-ra58. (2014).

H.W. Kang et al. "A 3D bioprinting system to produce human-scale tissue constructs with structural integrity", *Nature biotechnology* ;34(3):312. (2016).

S.V. Murphy et al., "3D bioprinting of tissues and organs", *Nature biotechnology*;32(8):773. (2014).

S. Wu et al., "Living nano-micro fibrous woven fabric/hydrogel composite scaffolds for heart valve engineering", *Acta Biomaterialia*;51:89-100. doi: http://doi.org/10.1016/i.actbio.2017.01.051. (2017).

M. Akbari et al., "Composite Living Fibers for Creating Tissue Constructs Using Textile Techniques" *Advanced Functional Materials*;24(26):4060-7. doi: doi:10.1002/adfm.201303655. (2014).

K. Garg et al., "Transplantation of devitalized muscle scaffolds is insufficient for appreciable de novo muscle fiber regeneration after volumetric muscle loss injury" *Cell Tissue Res* 358, 857-873, doi:10.1007/s00441-014-2006-6 (2014).

* cited by examiner

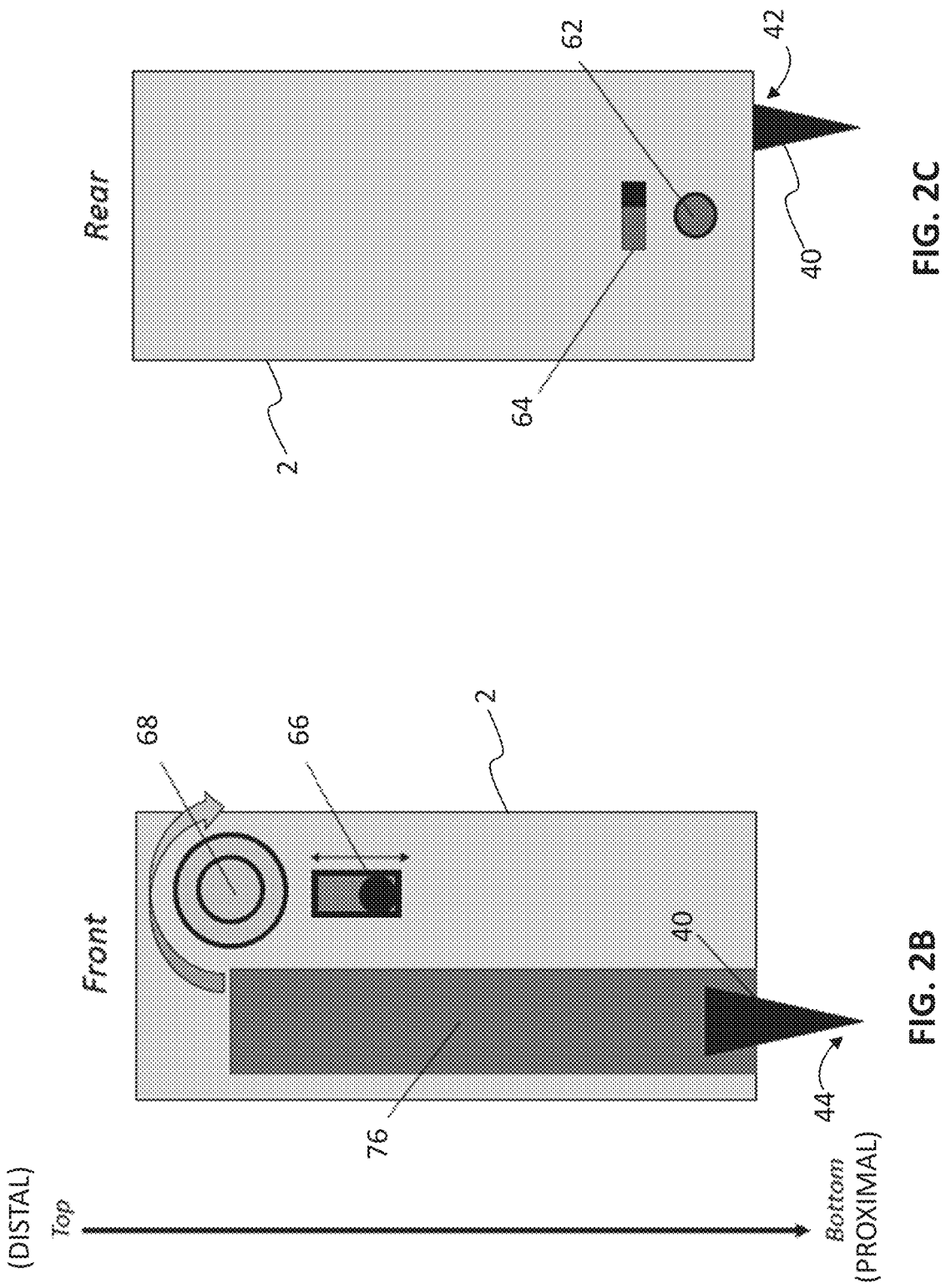

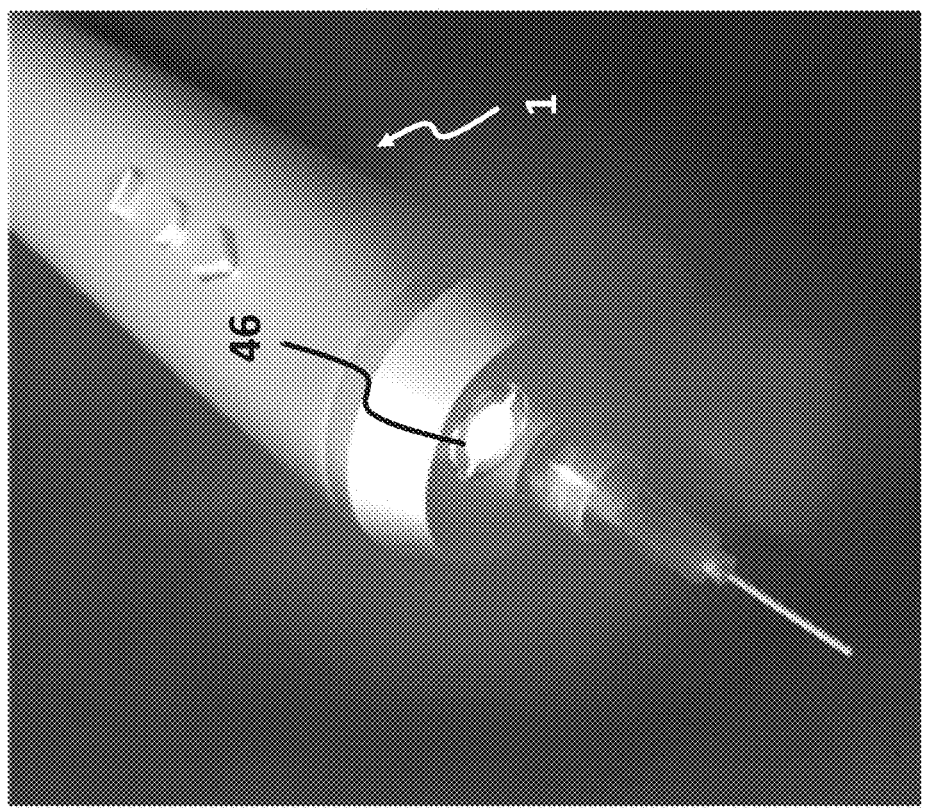
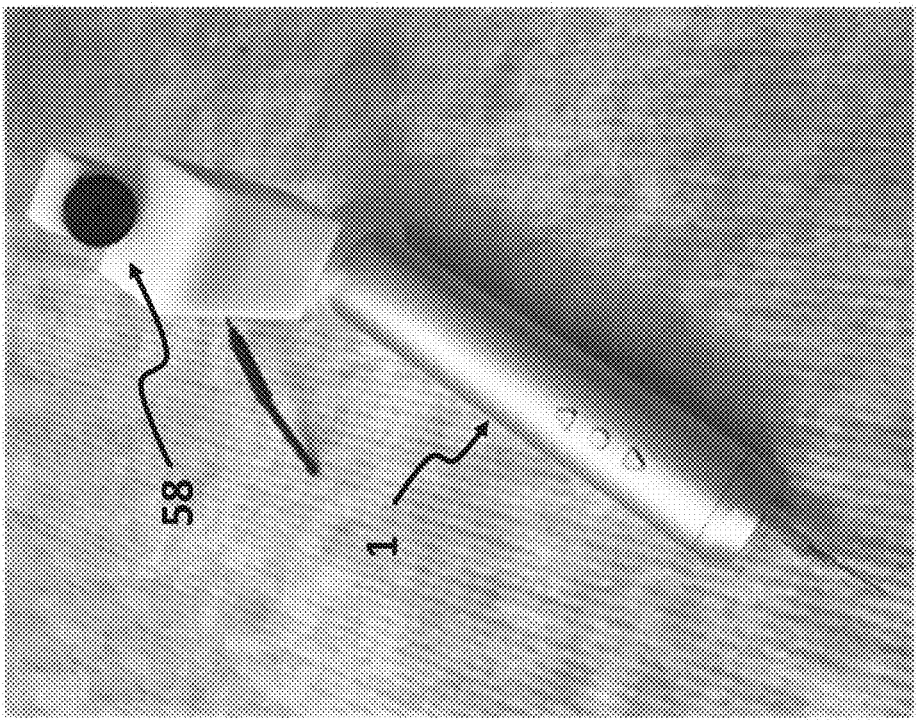

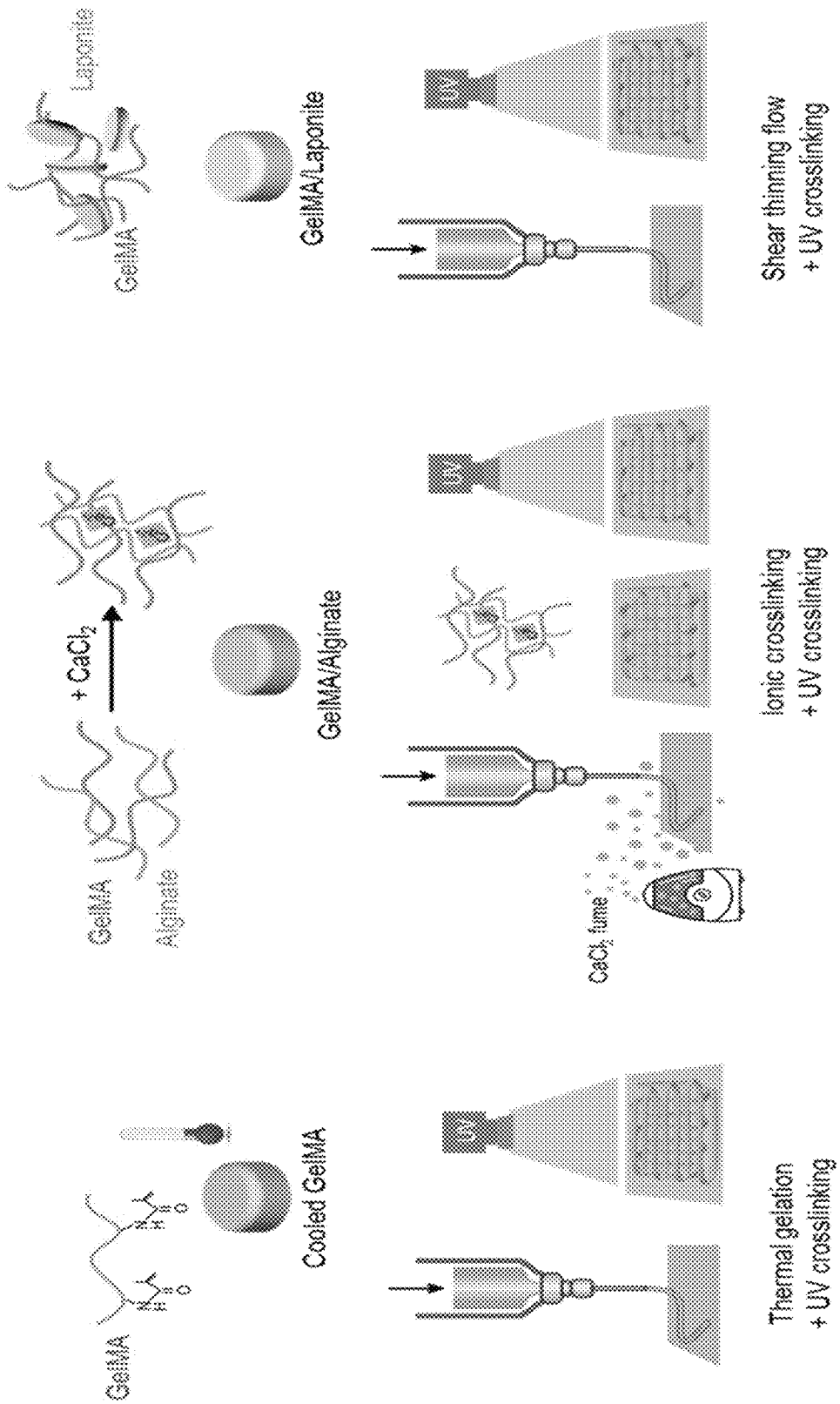

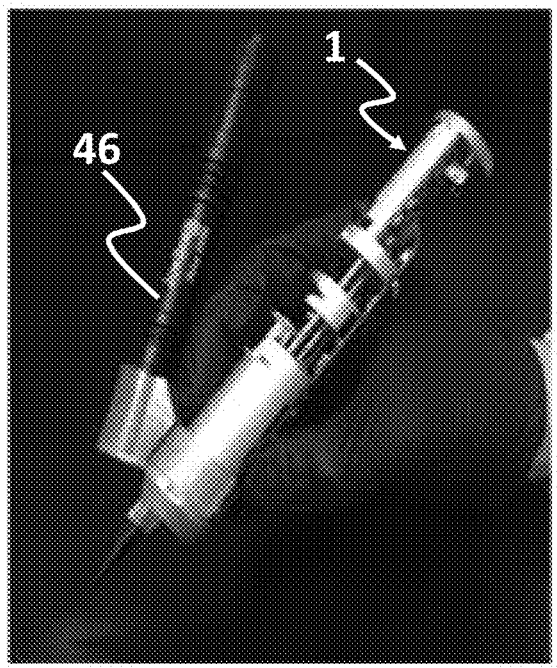
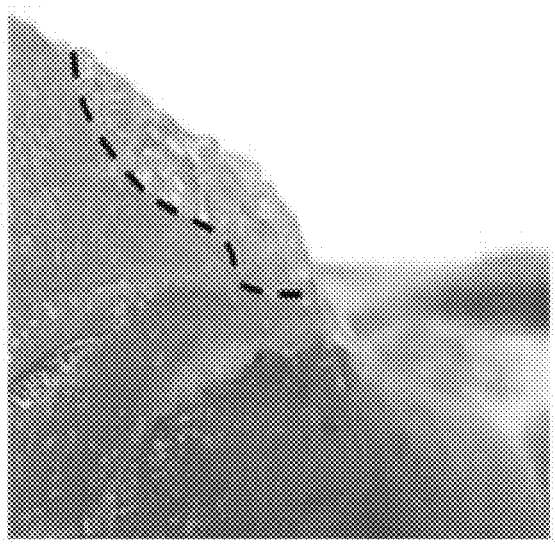
FIG. 9B  FIG. 9C
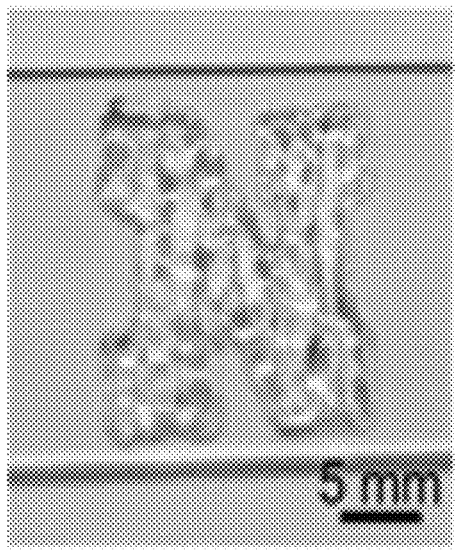
FIG. 9D

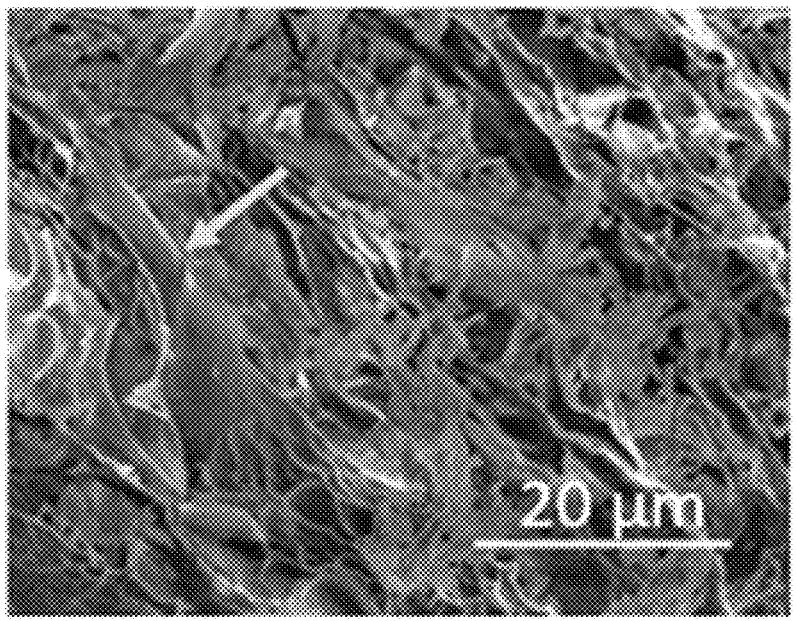
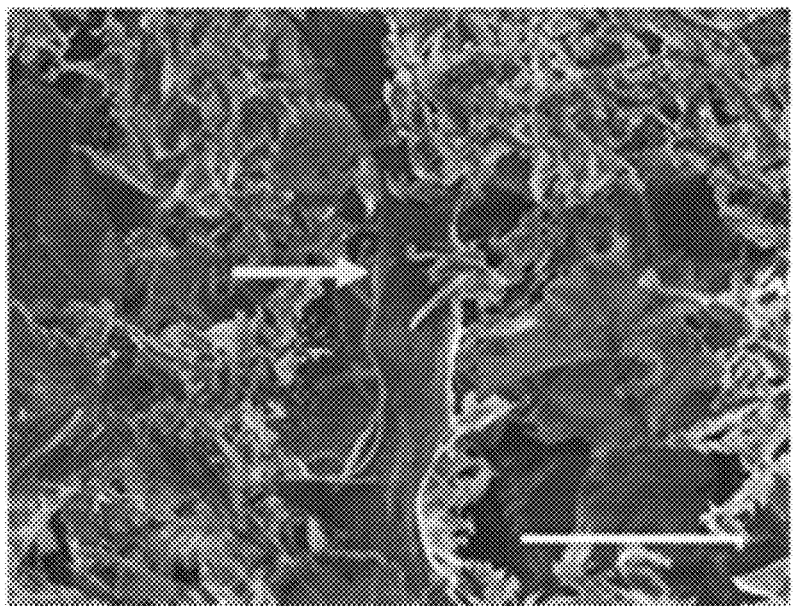
FIG. 16F

BIOPRINTER DEVICES, SYSTEMS AND METHODS FOR PRINTING SOFT GELS FOR THE TREATMENT OF MUSCULOSKELETAL AND SKIN DISORDERS

CROSS-REFERENCE TO RELATED APPLICATIONS

This application claims the benefit of U.S. Provisional Application No. 62/748,124, filed Oct. 19, 2018, which is incorporated herein by reference in its entirety.

STATEMENT AS TO FEDERALLY SPONSORED RESEARCH

This invention was made with government support under GM126831 and AR073822 awarded by the National Institutes of Health. The government has certain rights in the invention.

TECHNICAL FIELD

The present disclosure relates to medical devices for treatment of musculoskeletal and skin disorders, and more particularly to devices, systems and methods that utilize bioprinters to form scaffold structures in situ to facilitate treatment of the musculoskeletal and skin disorders in patients.

BACKGROUND

Skeletal muscle damage, which can be caused by varied etiologies including crush injuries, burns, and tumors, are a leading cause of loss of independence, disability, and mortality (50). Volumetric muscle loss (VML), specifically, is caused by traumatic injuries or other underlying conditions necessitating surgical intervention, and results in an en bloc loss of skeletal muscle with corollary functional impairment (3). Regenerative medicine approaches such as growth factor and stem cell delivery have shown some promise, but the majority of these approaches have been limited by low cell engraftment and factor bioavailability (51). Thus, a new paradigm for the treatment of musculoskeletal tissue damage is needed that can provide an effective and long-term therapy for most patients.

In the past decade, bioprinting has emerged as a technology that can create highly organized tissue constructs that mimic the complex architecture of various organs (52). Three-dimensional (3D) bioprinters are capable of printing both hard and soft polymers (53). The scaffolds 3D printed for the engineering of soft tissue are typically hydrogel-based. Despite the impressive level of the structural details achievable with 3D bioprinters, the implantation of hydrogel-based constructs has remained a major rate-limiting step. Hydrogels are not suturable and once fabricated do not adhere properly to tissues (54, 55). Moreover, conventional 3D bioprinters are slow in responding to the urgent clinical needs. For example, in the case of a traumatic injury, it takes several hours to take 3D images from the injury site and reconstruct the SDL file. The printing process on its own takes several hours. Thus, by the time that the construct is ready, the patient has already gone through surgical procedures and the implantation of the scaffold even if, requires a secondary surgery.

VML is seen in traumatic injuries or other underlying conditions necessitating surgical intervention and results in an en bloc loss of skeletal muscle with corollary functional impairment (1). VML is often a result of traumatic extremity injury and results in major social tribulations and economic hardship. Skeletal muscle is a highly organized tissue that usually maintains a robust ability to regenerate (2). VML injuries, however, are characterized by substantial soft tissue destruction, incomplete tissue regeneration, and extensive fibrosis; all of which limit the recovery of extremity function (3). Although conventional reconstructive treatments for these injuries can prevent amputation, they are limited in their ability to restore muscle strength and movement. Current VML treatment methods include autogenic muscle flap transplantation and prosthetic bracing (1, 4-6). Muscle tissue transplantation is the current standard clinical VML treatment, but is limited by the availability, functional and wound complications at the donor site, incomplete functional restoration, and high failure rates (1, 2, 4-10). Additionally, muscle flap transfer is a technically difficult operation and requires a highly skilled surgical team. Thereby, this approach is principally limited to tertiary care centers (4). These complications can result in the need for further surgical procedures at the wound site (2). In addition, muscle flap transfer is capable of only partial restoration of native function (1, 6). Prosthetic bracing is another treatment paradigm for patients with VML. Although the complications of surgical procedures are avoided, prosthetics must be custom made for each patient, which is expensive (4). Braces also fail to restore the native structure and function of the muscle and do not work for all types of VML (4, 6). Due to a lack of definitive treatment, VML often leads to permanent disability and pain, despite multiple interventions (1, 11). Regenerative medicine approaches such as growth factor and stem cell delivery have shown some promise, but the majority of these approaches have been limited by low cell engraftment or factor bioavailability (1).

Tissue engineering holds great potential as an alternative therapy by creating functional tissue constructs that can re-establish the structure and function of injured muscle (12). For VML treatment, a scaffold is required that can promote cellular ingrowth and tissue function (13). The scaffold should offer biomimetic mechanical and biochemical properties, a suitable degradation profile, proper biocompatibility, and adequate porosity (14). Various biomaterials and biofabrication strategies have been developed to fabricate such scaffolds. In the past decade, 3D printing has received significant attention due to its ability to produce highly defined constructs matching the geometry of the defect site (15-18). 3D printers are capable of printing both hard and soft polymers (19, 20). Bioprinters have the unique ability to print multiple biomaterials or their gradients with and without cells (21, 22). Furthermore, bioprinting has allowed for the encapsulation of cells and tissue-specific biological factors in stable 3D architectures mimicking the native ECM without adversely affecting cell viability and function (23-26).

Bioprinted 3D scaffolds for the engineering of soft tissue are typically hydrogel-based bioinks (27). Despite the impressive level of structural detail achievable with 3D bioprinters, the implantation of hydrogel-based constructs has remained a major rate-limiting step. Hydrogels are not suturable and once fabricated, they do not adhere properly to tissues (23, 28). Moreover, conventional 3D bioprinting methods are slow in responding to urgent clinical needs. For example, in the case of a traumatic injury, it takes several hours to take 3D images of the injury site, reconstruct a graphical model, and convert the model into a stereolithography (STL) file. Furthermore, the duration of the printing process is highly dependent on the printing method and can take several hours. Thus, by the time that the construct is ready, the patient has already undergone initial surgical intervention, and the implantation of the scaffold requires secondary surgery. Recent research has explored the possibility of developing 3D printers that are mobile and can be used for direct printing on targeted surfaces for cartilage and skin regeneration (29, 30). These in situ printers are typically extrusion-based devices and partially automated, where only some of them are capable of automatically positioning the biological materials in the planned location. In one recent study, a sophisticated bioprinter was reported for the printing of autologous cells directly into the wound bed (31). Despite the excellent resolution of this bioprinter, it was not feasibly portable for use in remote settings. Furthermore, a technology that can adequately address the limitations associated with skeletal muscle defects has not been developed.

SUMMARY OF THE DISCLOSURE

The use of the disclosed bioprinters capable of in situ printing of adhesive scaffolds overcome important challenges associated with the treatment of VML injury. Disclosed are bioprinter devices, bioprinter systems, and associated methods. The bioprinter according to the disclosure is an extrusion-based device capable of continuously extruding biomaterials and includes an integrated light source for crosslinking of the extruded bioink. The platform can print photocrosslinkable hydrogels such as gelatin methacryloyl (GelMA) for VML injuries immediately in situ. GelMA is a collagen-derived biomaterial that closely mimics the extracellular matrix (ECM) of native skeletal muscles. (32) Furthermore, GelMA adheres to body tissues and has been used as a bioadhesive in the literature. (33, 34) Thus, the in situ printing of GelMA is expected to eliminate the need for additional surgeries and solve the challenges of hydrogel-based scaffold implantation. In addition, the use of handheld bioprinters facilitates the deposition of bioink and the formation of scaffolds on non-flat surfaces at the injury site.

By way of examples, the disclosure discusses development of the disclosed bioprinter devices, systems and methods that are capable of in situ printing and crosslinking of hydrogel scaffolds. The bioprinter benefits from an integrated ultraviolet (UV) light source to photocrosslink the deposited bioink hydrogels in the geometry of the defect. The in situ crosslinking resulted in proper adhesion of the hydrogels to the injury site of skeletal muscle tissue. The bioprinter was also used for the delivery of muscle cells without negatively impacting their viability and proliferation. The in situ bioprinted scaffolds supported the formation of multinucleated myotubes. The engineered partially automated bioprinter was successfully tested in the reconstruction of the defect site in a murine VML injury model, where the placement of the scaffold promoted muscle hypertrophy following injury.

Recent advancements in the field of device manufacturing enabled the design and manufacture of the disclosed bioprinter devices, systems and methods that can print photocrosslinkable hydrogels such as GelMA in situ at the time of injury. This eliminates the need for a second surgery and the in situ printing of adhesive hydrogels solves the challenge of implantation of hydrogel-based scaffolds.

Embodiments of a bioprinter are provided and are unique and can revolutionize the use of 3D bioprinters in surgical procedures. The handheld printer is robust and can be used in any place and in any setting without the need of accessing an expensive imaging modality. The surgeon can inspect the defect and adjust the printing rate and fill the defect area. The in situ printing and crosslinking enhances the adhesion of the material to the surrounding tissue, which eliminates the risk of scaffold slippage. An integrated camera allows on the fly inspection of the printing quality and adjusting the speed to avoid printing defects. This bioprinter can even be used in settings without the physical presence of the surgeon as the procedure can be recorded and viewed remotely. The surgeon can remotely make recommendations on the printing process. The device minimizes the response time to traumatic injuries leading to VML.

In one aspect, the disclosure describes a bioprinter device. The bioprinter device includes a housing defining: a proximal end, and a distal end opposite the proximal end. The housing includes a receptacle for receiving at least a portion of a syringe assembly within the housing. The bioprinter includes a power supply disposed within the housing. The bioprinter device includes an electric actuator disposed within the housing at a position sufficient to facilitate an operable coupling of the electric actuator to at least a portion of a plunger of the syringe assembly upon an insertion into the receptacle. The bioprinter device includes a control interface positioned at least partially within the housing and including at least one control device operable from an exterior of the housing. The bioprinter device includes a controller disposed within the housing and coupled to: the power supply, the electric actuator, and the control interface. The controller regulates a flow of power from the power supply to the electric actuator based on signals received from the at least one control device, to facilitate regulating an actuation of the plunger by the electric actuator.

In another aspect, the disclosure describes a bioprinter system. The bioprinter system includes a housing defining: a proximal end, and a distal end opposite the proximal end. The housing includes a receptacle. The bioprinter system includes a syringe assembly positioned at least partially in the receptacle. The bioprinter system includes: a barrel for containing a liquid, a nozzle in flow communication with the barrel, and a plunger slidably disposed inside the barrel. The bioprinter system includes a power supply disposed within the housing. The bioprinter system includes an electric actuator disposed within the housing and operably coupled to at least a portion of the plunger. The bioprinter system includes: a control interface positioned at least partially within the housing, and at least one control device operable from an exterior of the housing. The bioprinter system includes a controller disposed within the housing and coupled to: the power supply, the electric actuator, and the control interface. The controller regulates an actuation of the plunger by the electric actuator by regulating a flow of power from the power supply to the electric actuator based on signals received from the at least one control device, to facilitate regulating a flow of the liquid from the barrel through the nozzle and to the exterior of the housing.

In yet another aspect, the disclosure describes a method for treating a musculoskeletal disorder of a patient. The method includes positioning a bioprinter at a situs of the musculoskeletal disorder in the patient. The method includes extruding a hydrogel formulation from the bioprinter into the situs. The method includes curing the hydrogel formulation in the situs. The hydrogel formulation has a composition effective to generate, upon the curing, a scaffold structure in the situs to facilitate muscle hypertrophy and/or new muscle fibers in the situs.

In still another aspect, the disclosure describes a method for treating a skin disorder of a patient. The method includes positioning a bioprinter at a situs of the skin disorder in the patient. The method includes extruding a hydrogel formulation from the bioprinter into the situs. The method includes curing the hydrogel formulation in the situs. The hydrogel formulation has a composition effective to generate, upon the curing, a scaffold structure in the situs to facilitate wound healing in the situs.

Further and alternative aspects and features of the disclosed principles will be appreciated from the following detailed description and the accompanying drawings. As will be appreciated, the principles related to devices, systems and methods that utilize bioprinters to form scaffold structures in situ to facilitate treatment of the musculoskeletal and skin disorders in patients disclosed herein are capable of being carried out in other and different embodiments, and capable of being modified in various respects. Accordingly, it is to be understood that both the foregoing general description and the following detailed description are exemplary and explanatory only and do not restrict the scope of the appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 2A-2D are schematic diagrams of a bioprinter system and bioprinter device that may be used in the method of FIG. 1 according to embodiments of the disclosure.

FIG. 4A illustrates a handheld printer with attached high definition (HD) camera for in situ monitoring according to an embodiment of the disclosure.

FIG. 4B illustrates UV light curing capability attached to soft gel printer according to an embodiment of the disclosure.

FIG. 6A illustrates pristine GelMA bioinks according to embodiments of the disclosure.

FIG. 6B illustrates GelMA:Alginate (0.5%) formulation where alginate is crosslinked during printing with $CaCl_2$ fume followed by GelMA crosslinking after printing.

FIG. 6C illustrates GelMA:Laponite (0.5%) bioinks according to an embodiment of the disclosure.

FIGS. 9A-9D illustrate the utilization of a handheld bioprinter for in situ printing of scaffolds according to embodiments of the disclosure.

FIG. 16F illustrates SEM images of 5% and 7% (w/v) lyophilized GelMA hydrogels with encapsulated cells post differentiation 14 days of culture according to embodiments of the disclosure.

DETAILED DESCRIPTION

Reference will now be made in detail to specific embodiments or features, examples of which are illustrated in the accompanying drawings. Wherever possible, corresponding or similar reference numbers will be used throughout the drawings to refer to the same or corresponding parts. Moreover, references to various elements described herein, are made collectively or individually when there may be more than one element of the same type. However, such references are merely exemplary in nature. It may be noted that any reference to elements in the singular may also be construed to relate to the plural and vice-versa without limiting the scope of the disclosure to the exact number or type of such elements unless set forth explicitly in the appended claims.

Figure 1:
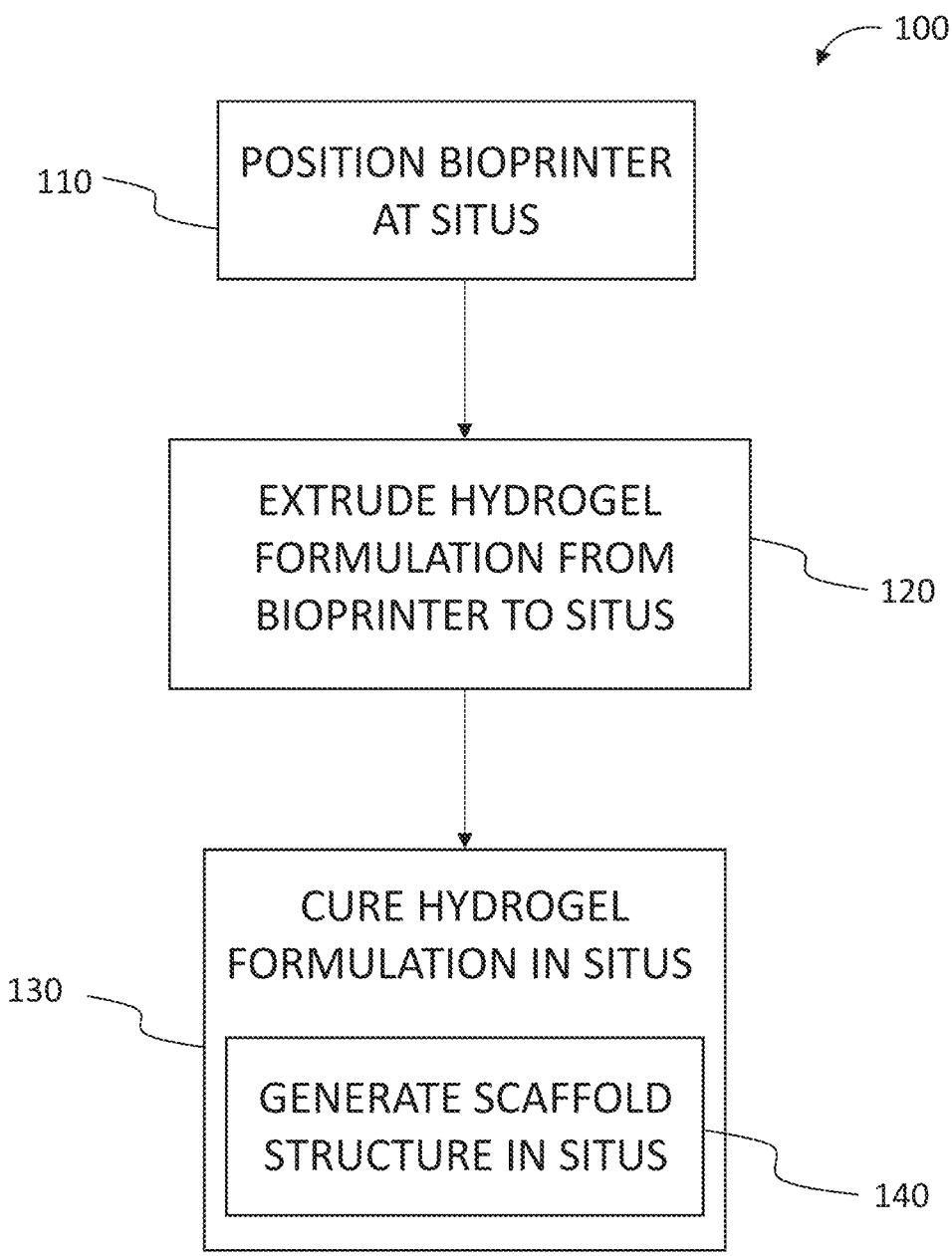
FIG. 1 is a flow chart of a method of treatment of musculoskeletal and/or skin disorders according to an embodiment of the disclosure.

FIG. 1 is a flow chart of a method 100 for treating a musculoskeletal disorder of a patient. In one embodiment, the patient is a human being and the method 100 is applied in a medical practice setting. In another embodiment, the patient is an animal, and the method 100 is applied in a veterinary practice setting. The method 100 includes positioning 110 a bioprinter at a situs of the musculoskeletal disorder (e.g., VML) in the patient. With the bioprinter so positioned 110, the method 100 includes extruding 120 a hydrogel formulation from the bioprinter into the situs. The method 100 includes curing 130 the hydrogel in the situs. As described in further detail herein, including by way of examples, the hydrogel formulation has a composition that is effective to generate 140, upon the curing 130, a scaffold structure in the situs to facilitate muscle hypertrophy and/or new muscle fiber formation in the situs. The muscle hypertrophy so facilitated leads to formation of new muscle fibers in, and proximal to, the situs of the musculoskeletal disorder in the patient.

In another embodiment, the steps (110, 120, 130 and 140) of method 100 are applied to a skin disorder in a patient, either instead of, or in addition to, being applied to a musculoskeletal disorder. In the embodiment, the hydrogel formulation has a composition that is effective to generate 140, upon the curing 130, a scaffold structure in the situs to facilitate skin growth in the situs. The skin growth so facilitated leads to wound healing in, and proximal to, the situs of the skin disorder in the patient.

Figure 2A:
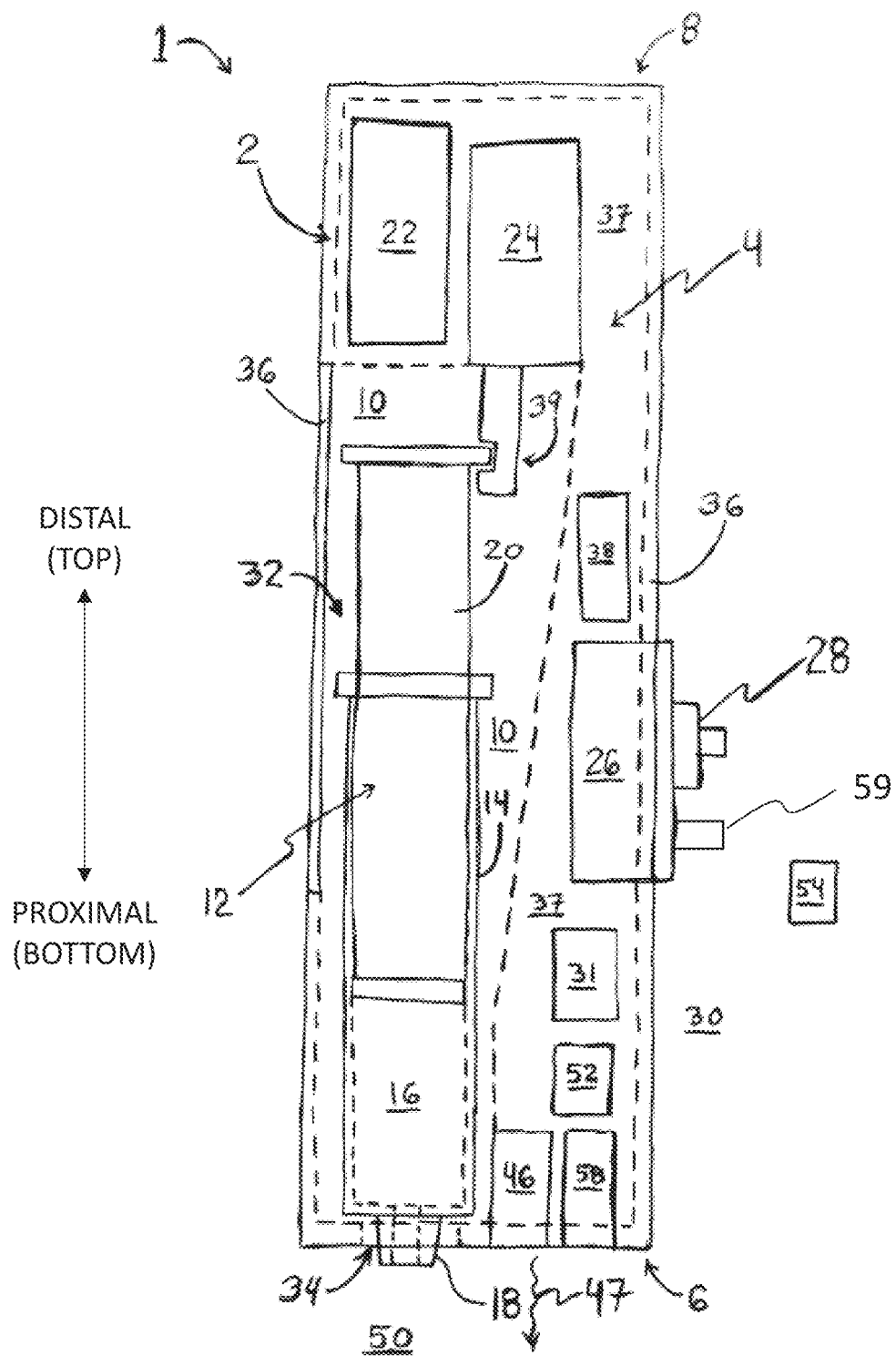

FIG. 2A is a schematic diagram of a bioprinter system 1. System 1 includes a device 2 having a housing 4. Housing 4 defines: a proximal end 6, and a distal end 8 opposite the proximal end 6. The housing 4 includes a receptacle 10 for receiving at least a portion of a syringe assembly 12 within the housing 4. System 1 thus includes the syringe assembly 12 for positioning at least partially in the receptacle 10. The syringe assembly 12 includes: a barrel 14 for containing a liquid 16, a nozzle 18 in flow communication with the barrel 14, and a plunger 20 slidably disposed inside the barrel 14.

Device 2 includes a power supply 22 disposed within the housing 4. In one embodiment, the power supply 22 includes one or more batteries. Where power supply 22 is at least one rechargeable battery, device 2 may include circuitry and connector ports for recharging the at least one rechargeable battery, such as a port for receiving a mating plug from a charger cable, and a power converter or regulator circuit for transmitting electric power at a required voltage and/or current to the rechargeable battery. Device 2 includes an electric actuator 24 disposed within the housing 4 and operably coupled to at least a portion of the plunger 20. A variety of electric actuator(s) 24 may be used in device 2. For example, and without limitation, the electric actuator 24 may be at least one of: a stepper motor, a direct current (DC) motor, and a linear actuator. In some embodiments, the electric actuator 24 is a pneumatic actuator, and device 2 includes a subsystem for compressing air or compressing fluid for use with the pneumatic actuator. In any event, the electric actuator 24 is disposed, at least in part, within the housing 4 at a position that is sufficient to facilitate an operable coupling of the electric actuator 24 to at least a portion of the plunger 20 of the syringe assembly 12 upon an insertion of the syringe assembly 12 into the receptacle 10. As an example, a stepper, or DC, motor may have a geared shaft and at least a portion of the plunger 20 may have corresponding teeth. In such embodiments of system 1, a user may insert the nozzle 18 and barrel 14 into the receptacle 10 such that the teeth on the plunger 20 align with teeth of the gear of the electric actuator 24 motor shaft. In another example, a linear actuator may have a notched working end 39. In such embodiments of system 1, a user may insert the nozzle 18 and barrel 14 into the receptacle 10 such that a corresponding portion of the plunger 20 (e.g., a flange of the plunger 20) aligns with the notch of the linear actuator working end 39. In any event, the positioning of the electric actuator 24 in the housing 4 enables at least a portion of the plunger 20 to be operably coupled to the electric actuator 24 so that the plunger 20 may be moved alternately proximally and distally by the electric actuator 24.

Device 2 includes a control interface 26 positioned at least partially within the housing 4. Control interface 26 includes at least one control device 28 operable from an exterior 30 of the housing 4. Device 2 includes a controller 31 disposed within the housing 4 and coupled to: the power supply 22, the electric actuator 24, and the control interface 26. The controller 31 regulates actuation of the plunger 20 by the electric actuator 24 by regulating a flow of power from the power supply 22 to the electric actuator 24 based on signals received from the at least one control device 28, to facilitate regulating a flow of the liquid 16 from the barrel 14 through the nozzle 18 and to the exterior 30 of the housing 4. In one embodiment, the device 2 includes a light source 46 for directing light 47 proximally from the proximal end 6. In one embodiment, the liquid 16 extruded 120 in method 100 is cured 130 using ultraviolet (UV) light, and the bioprinter device 2 used in method 100 includes a UV light source 46. In another embodiment, the liquid 16 extruded 120 in method 100 is cured 130 using visible light, and the bioprinter device 2 used in method 100 includes a visible light source 46. In yet another embodiment, the liquid 16 extruded 120 in method 100 is cured 130 using heat, and the bioprinter device 2 used in method 100 includes a light source 46 that is capable of generating and directing infrared (IR) energy proximally from the proximal end 6. In still another embodiment, the liquid 16 extruded 120 in method 100 is cured 130 using, at least in part, a chemical-based curing 130 technique (e.g., $CaCl_2$ fumes passed over and/or onto the extruded 120 liquid 16), either instead of, or in addition to, curing 130 by directing light and/or heat from the light source 46 onto the extruded 120 liquid 16 in the situs.

When embodiments of system 1 having light source 46 are utilized in method 100, the curing 130 step of method 100 may include directing light (and/or, in the case of thermal curing 130, heat) from the light source 46 of the bioprinter device 2 onto the extruded 120 liquid 16 (e.g., a hydrogel formulation, as described in greater detail, by way of examples, below). In those embodiments of method 100 where the curing 130 includes directing light onto the extruded 120 liquid 16, and where the liquid 16 is a hydrogel formulation, the hydrogel formulation includes a photoinitiator at a concentration effective to facilitate the curing 130.

A variety of control device(s) 28 may be used in device 2. For example, and without limitation, the control device(s) 28 may be at least one of: switches, toggles, variable resistors, potentiometers, buttons, nubs, knobs, levers, dials, and tactile or spring-loaded, touchpads. In one embodiment, the at least one control device 28 includes a first control device and at least a second control device. In a handheld embodiment of system 1, the first control device may be positioned proximal the second control device to facilitate ease of use by a user to manipulate the first and second control devices with his or her fingers while holding device 2. The device 2 includes a master power switch 59 that, when in an "on" position, enables an electric connection (e.g., closes a corresponding circuit branch) between the power supply 22 and the controller 31. Upon an appropriate user manipulation, the first control device transmits a first signal to the controller 31 to cause the controller 31 to alternately increase and decrease an actuation rate of the electric actuator 24. Upon an appropriate user manipulation, the second control device transmits a second signal to the controller 31 to cause the controller 31 to alternately maintain and change an actuation direction of the electric actuator 24. For instance, the first control device may be a potentiometer with an attached knob, and the second control device may be a two position toggle switch, where a first position of the two position toggle switch corresponds to a proximal direction of movement of a linear actuator, and a second position of the two position toggle switch corresponds to a distal direction of movement of a linear actuator. With the master power switch 59 in the on position, and the two position toggle switch in the first position, user may turn the knob from an "off" position through a series of intermediate knob positions to achieve a desired actuation rate for the linear actuator, and thereby achieve a desired fluid 16 flow rate from the nozzle 18 for use in method 100. Upon completion of method 100 and/or upon all liquid 16 being extruded 120 from barrel 14, user may manipulate the two position toggle switch to the second position to have the controller 31 cause the plunger 20 to be actuated by the linear actuator in the distal direction to thereby achieve a position to facilitate the removal of the syringe assembly 12 from the receptacle 10 by the user.

In the example shown in FIGS. 2B and 2C, the at least one control device 28 includes a first 62, a second 64, a third 66, and at least a fourth 68 control device 28. In this embodiment, the first 62 control device 28 is a button. System 1 user may manipulate the single button 62 from an "off" to an "on" position to enable an electric connection (e.g., close a corresponding circuit branch) between the power supply 22 and the controller 31, to thereby enable the electric actuator 24 and the light source 46 to be energized upon further command by the user. In this regard, the single button 62 may carry out a function that is equivalent, or at least similar, to the master power switch 59 of the above-described embodiment. The second 64 control device 28 is a two position toggle switch, and the third 66 control device 28 is another two position toggle switch. The fourth 68 control device 28 is rotational potentiometer (e.g., having a knob attached thereto). With the button 62 in the on position, upon an appropriate user manipulation, the electric actuator 24 is turned off and the light source 46 is turned on by moving the two position toggle switch 64 from a first to a second position. Likewise, the user moving the two position toggle switch 64 from the second to the first position turns off the light source 46 and turns the electric actuator 24 back on. With the electric actuator 24 moving the plunger 20 in the proximal direction, for example, the user moving the two position toggle switch 66 from a first to a second position reverses the actuation direction from proximal to distal. The user moving the knob of the rotational potentiometer 68 in a first direction increases the actuation rate (e.g., as shown by the curved arrow in FIG. 2B), while moving the potentiometer 68 knob in a second, opposite, direction decreases the actuation rate, where the potentiometer 68 knob turned fully by the user to a stop in the second direction causes the electric actuator 24 to stop actuating the plunger 20.

Alternatively, and instead of having the button 62 for the first 62 control device 28 and the two position toggle switch 64 for the second 64 control device 28, the second 64 control device 28 may be a three position toggle switch (not shown in FIG. 2A) having first (middle), second (e.g., left, or proximal), and third (e.g., right, or distal) positions. The middle position corresponds to the "off position of the button 62, the left, or proximal, position corresponds to the first position of the two position toggle switch 64 described above, and the right, or distal, position corresponds to the second position of the two position toggle switch 64 described above. Similarly, in another example, the left, or proximal, position may correspond to the second position, and the right, or distal, position may correspond to the first position, of the two position toggle switch 64, respectively.

The controller 31, and the control devices 28 manipulated by system 1 users as described in the above use cases, provide fine control over the extruding 120 and curing 130 steps of method 100. In one embodiment, the control device(s) 28 may be manipulated by system 1 users to enable the extruding 120 and curing 130 steps to be performed simultaneously in method 100 (e.g., by having the electrical actuator 24 and the light source 46 turned on at the same time). In another embodiment, in method 100, a performance of the extruding 120 step and a performance of the curing 130 step are separated by a small time gap in method 100. In one example, the duration of the small time gap is determined by how much time the system 1 user is able, or desires, to turn the two position toggle switch from the first to the second position, as described above. In another example, the controller 31 is a clocked controller (e.g., a microprocessor) and the controller 31 automatically pauses extruding 120 for a predetermined duration and energizes the light source 46 for that predetermined duration, including, without limitation, according to a predetermined timing sequence. In such embodiments, providing a time gap between the extruding 120 and curing 130 in method 100 facilitates the liquid 16 contacting and/or penetrating into the situs of the musculoskeletal and/or skin disorder so as to facilitate contact between the generated 140 scaffold structure and the situs upon the curing 130.

In an embodiment, the receptacle 10 defines: a first opening 32, and a second opening 34, through a wall 36 of the hollow housing 4, where the wall 36 separates an interior cavity 37 of the housing 4 from the exterior 30 of the housing 4. The first opening 32 is positioned distally from the second opening 34 to facilitate access to the syringe assembly 12 from the exterior 30 of the housing 4. In one embodiment, the first opening 32 is positioned to further facilitate a removable insertion of at least a portion of the syringe assembly 12 into the receptacle 10 through the first opening 32. The second opening 34 is positioned at, or proximal to, the proximal end 6 to facilitate: access to the nozzle 18 from the exterior 30 of the housing 4 through the second opening 34, and to facilitate a flow of the liquid 16 from the barrel 14 through the nozzle 18 to the exterior 30 of the housing 4. In one embodiment, the second opening 34 is positioned to further facilitate access to the nozzle 18 from the exterior 30 upon the removable insertion of at least a portion of the syringe assembly 12 into the receptacle 10. The receptacle 10, and the syringe assembly 12, are thus configured to facilitate a removable insertion of at least a portion of the syringe assembly 12 into the receptacle 10 through the first opening 32. In the embodiment, the device 2 is a reusable device able to be repeatedly sequentially loaded with syringe assemblies 12. Reusable devices 2 may, for example, be fabricated from component material(s) of construction that are repeatedly and sequentially sterilizable using thermal and/or chemical techniques that are known to persons having skill in the art. In other embodiment, device 2 is disposable, or designed for use for only a limited period of time, and, as such, need not be fabricated from component material(s) of construction that are sterilizable.

As shown in FIGS. 2B and 2C, in one embodiment, device 2 includes a window 76 positioned through a portion of the wall 36 such that a user of system 1 may view the contents of the barrel 14 of the syringe assembly 12. Device 2 includes an elongate tip 40 in flow communication with the nozzle 18. In an example, the tip 40 is removably coupled to the nozzle 18, as by the Luer-lock configuration. The tip 40 includes: a distal end 42 coupled (e.g., removably coupled) to the nozzle 18, and a proximal end 44 extending proximally from the nozzle 18. The tip 40 is hollow, where openings into the hollow cavity of the tip 40 are defined by the distal 42 and proximal 44 ends of the tip 40. In one embodiment, the tip 40 is tapered, where a diameter of the opening at the tip 40 distal end 42 is greater that a diameter of the opening at the tip 40 proximal end 44. In another embodiment (not shown in FIGS. 2B and 2C), the diameters of the distal 42 and proximal 44 ends of the tip 40 are equal (e.g., where tip 40 is embodied in a straight needle). In an embodiment, the diameter of the tip 40 proximal end 44 is between 100 and 1000 microns (μm). In another embodiment, the diameter of the tip 40 proximal end 44 is between 400 and 600 μm.

In one embodiment, the liquid 16 contained in the barrel 14 of the syringe assembly 12 is a hydrogel formulation. The hydrogel formulation may include a plurality of live cells (e.g., muscle and/or skin cells—which may or may not be obtained and/or derived from the patient's own cells—that are capable of proliferation and/or differentiation in the situs in the presence of the extruded 120 and cured 130 scaffold structure) suspended, or otherwise mixed, in the hydrogel formulation. Additionally, or instead, the hydrogel formulation may include at least one of: biological factors, drugs, platelet rich plasma, platelet rich fibrin, nanoparticles, microparticles, conductive materials, bioceramic, and polymeric particles. In another embodiment, the hydrogel formulation does not include live cells. In such embodiments, method 100 may include depositing the live cells onto the scaffold structure in the situs after the extruding 120, and optionally after the curing 130, step(s) of method 100. Additionally, or instead, method 100 may include depositing at least one of the biological factors, drugs, platelet rich plasma, platelet rich fibrin, nanoparticles, microparticles, conductive materials, bioceramic, and polymeric particles onto the scaffold structure in the situs after the extruding 120, and optionally after the curing 130, step(s) of method 100.

In one embodiment, the hydrogel formulation includes nanomaterials and/or nanoparticles at a concentration effective to facilitate sheer thinning of the generated 140 scaffold structure upon the curing 130 (e.g., by curing of the shear thinning materials by removal of shear stress). For hydrogel formulations that are cured 130 in method 100 using heat, the hydrogel formulation may include thermoresponsive materials that are cured by an induced temperature change on the surface (e.g., the situs of the musculoskeletal and/or skin disorder) upon which the hydrogel formulation is extruded 120 in method 100. The generated 140 scaffold structure resulting from performance of method 100 including, for example and without limitation, using system 1 with device 2, exhibits physical properties that facilitate greater success in treatment outcomes of musculoskeletal and/or skin disorders, as compared to known methods of treatment for such disorders. The scaffold structure resulting from performance of method 100 using, for example, system 1 with device 2, is adhesive to body tissues including skeletal muscles, skin, bone, tendon, ligaments, and so forth. The scaffold structure has pore sizes (e.g., as a pore size distribution) ranging from less than 10 nanometers (nm, but>0 nm) to 10 millimeters (mm). In one embodiment, the pore sizes of the scaffold structure are from 10 nm to 10 mm. The scaffold structure has an ultimate shear adhesion stress to skeletal muscle of from 50 to 75 kilopascals. The scaffold structure has a compressive modulus of from 10 kilopascals to 10 gigapascals. In one embodiment, the compressive modulus of the scaffold structure is from 25 kilopascals to 2 gigapascals. In another embodiment, the compressive modulus of the scaffold structure is from 25 kilopascals to 40 kilopascals.

As described herein, the system 1 with device 2 is a handheld bioprinter system 1 and device 2, and the steps (110, 120 and 130) of method 100 are performed by hand. In other embodiments, the system 1 is integrated into an assistive device and/or a surgical robot and at least one of the steps (110, 120 and/or 130) of method 100 are performed by, for example, the surgical robot, instead of being performed by hand. In such embodiments, controller 31 is further configured to communicate with a robot controller and associated communication interface, either instead of, or in addition to, being coupled to the control device(s) 28 as described above. In other words, system 1 with device 2 may either be configured for dedicated use with automated systems like surgical robots, or it may be a dual use system 1 capable of being used entirely by hand or entirely with automated systems like surgical robots.

In an embodiment, device 2 includes a temperature regulation device 38 disposed within the housing 4. The temperature regulation device 38 is positioned in device 2, includes a pump, and is configured to maintain the liquid 16 in the barrel 14 at or near a constant temperature. In one embodiment, temperature regulation device 38 includes heating and/or cooling elements to alternately heat and/or cool a fluid other than liquid 16, where the pump directs a flow of the heated or cooled fluid through passages positioned inside, or around, a material of construction of receptacle 10 (e.g., as a jacket). With a liquid 16-filled syringe assembly 12 barrel 14 positioned at least partially in the receptacle 10 having the jacket, regulation of the temperature of the fluid flowing in the jacket passages facilitates a corresponding regulation of the temperature of the liquid 16 in the barrel 14. This temperature regulation facilitated by the temperature regulation device 38 may include cooling and/or heating the jacket fluid in order to correspondingly cool and/or heat the fluid 16 in the barrel 14. The jacket fluid may be a liquid (e.g., an aqueous glycol solution contained in a reservoir in, on or proximal the housing 4) or a gas (e.g., air from the exterior 30 of housing 4).

Figure 2D:
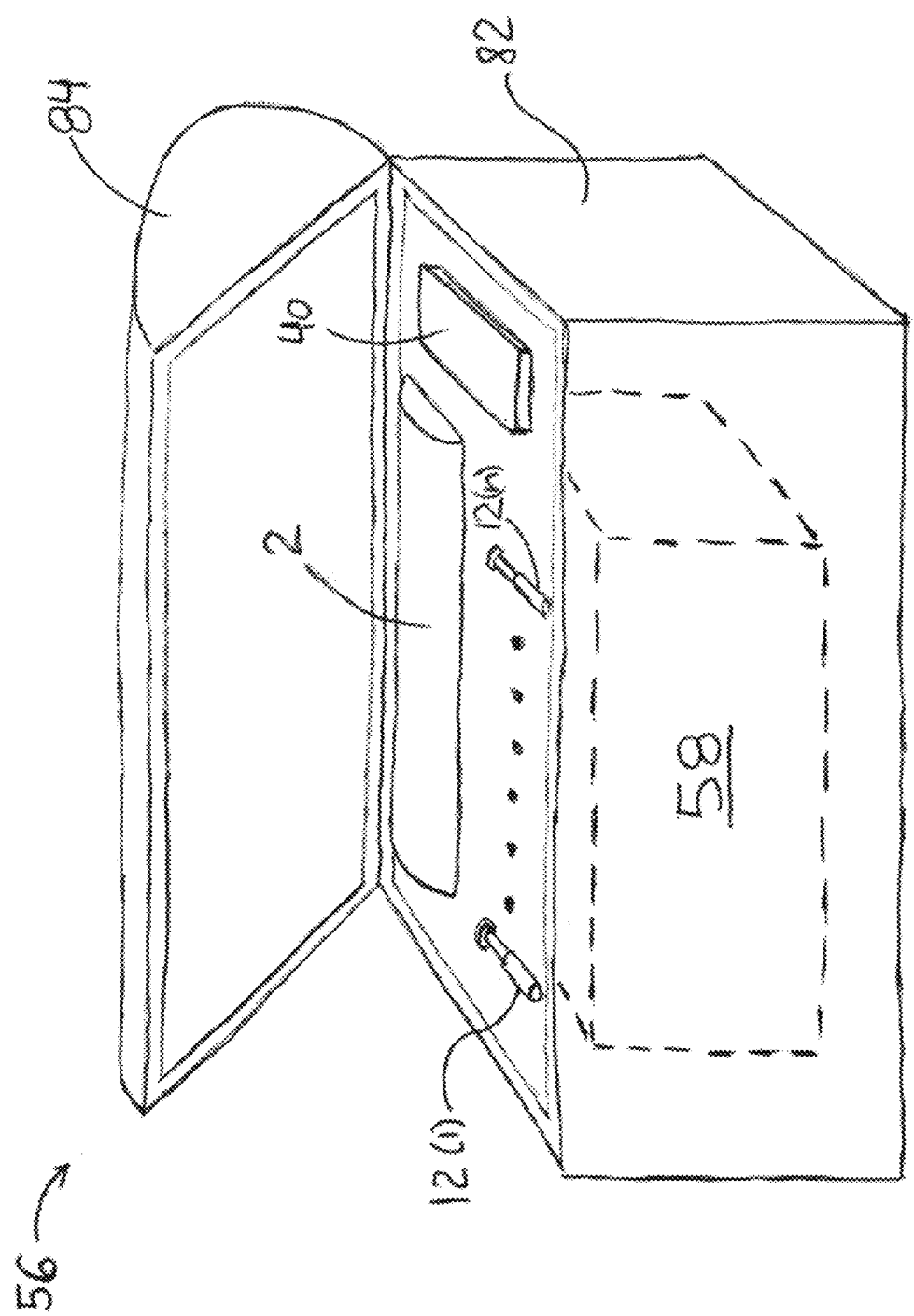

The device 2 may be a part of a bioprinter kit 56, as shown in FIG. 2D. The bioprinter kit 56 includes: at least one syringe assembly 12 having a barrel 14 at least partially filled with liquid 16 (e.g., a plurality of syringe assemblies 12(1)-12(n), each having their barrel 14 filled with the hydrogel formulation). The bioprinter kit 56 includes a temperature regulation means 58 for maintaining the liquid 16 in the barrel 14 at or near a constant temperature prior to the insertion of at least a portion of the syringe assembly 12 into the receptacle 10. In the example shown in FIG. 2D, the kit 56 includes a case 82 having a cover 84, and the temperature regulation means 58 is a gel pack that may either be cooled or heated before being placed proximal the syringe assemblies 12 inside the case. In another example (not shown in FIG. 2D) the temperature regulation means 58 is refrigerator and the case 82 of the refrigerator further includes a power supply or a cord and a connector for powering an electric refrigeration subsystem as part of the refrigerator temperature regulation means 58.

In embodiments of the disclosed system 1, device 2 and method 100, a variety of hydrogel formulation are useful. In some embodiments, the hydrogel formulation is preferably used as the liquid 16 in method 100 using the system 1 with device 2 at a specified temperature, or range of temperatures. The above-described temperature regulation device 38 and/or the temperature regulation means 58 may be employed for that purpose. Alternatively, the method 100 may be performed in the absence or regulating the temperature of liquid 16 prior to the positioning 110 and extruding 120 steps. Below are listed several hydrogel formulations used as the liquid 16 in method 100 according to the disclosure, along with the ranges of preferred temperatures for use:

GelMA (3-5° C.)
GelMA doped with nanoclay (e.g., Laponite) (3-37° C.)
Pluronic F127 (10-22° C.)
Alginate (2-37+° C.)

Specific preferred temperatures and/or temperature subranges for achieving and/or maintaining the hydrogel formulations before the extruding 120 step of method 100 are material dependent, including a dependence on a concentration of the base hydrogel material, as well as concentration(s) of additive(s) to the base hydrogel, as described in greater detail below by way of examples.

Referring to FIG. 2A, system 1 may include an imaging device 48 (e.g., still and/or video camera) for generating one or more videos and/or one or more still images of the exterior 30 of the housing 4 including a space 50 positioned proximal to the proximal end 6 (e.g., upon the performance of the positioning 110 step of method 100). Device 2 embodiments having the imaging device 48 may further include a transmitter 52 for transmitting the video(s) and/or image(s) to a receiver 54 positioned remote from the device 2. When such embodiments of system 1 are utilized in method 100, method 100 may further include transmitting video(s) and/or image(s) of a performance of at least one of: the positioning 110, the extruding 120, and the curing 130, from an imaging device of the bioprinter to a receiver 54 (e.g., of, or accessible by, a treatment provider supervising, at least in part, performance of one or more steps of method 100), where the receiver 54 is positioned remote from the patient and the system 1. In the embodiment, at least a portion of the method 100 as described herein may be performed by the treatment provider using telemedicine.

Example 1

In an embodiment a pen printer is provided. The pen printer is a device that can be used to print polymer hydrogels for in situ application, and can be easily operated using simple mechanical controls to extrude gels at a consistent rate. This flow can be customized to the desired flow rate. The gels are first loaded into a syringe and placed into the pen printer, where it is then extruded using electrical actuators controlled by a stepper motor. The stepper motor slowly pushes the back of the syringe towards the front, pushing the gels out. Because the gels are loaded into a standard Luer-lock syringe, the nozzle of the syringe can be optimized to the gel being used, using gage syringe tips or tapered tips. While this application can be used across a wide range of hydrogels, current hydrogels may include chitosan/alginate and GelMA-based hydrogels.

Chitosan/alginate gels are being researched for their structural and antimicrobial properties in skeletal muscle tissue applications. Gelatin Methacrylate is a gel that has been researched in the past for its customizable structural properties and large amount of binding cites for cells to latch onto. Both of these gels are derived from natural polymers, making them suitable candidates to be tested for research applications. Chitosan/alginate hydrogels are a sheer thinning material, while GelMA is photocrosslinkable. GelMA can be mixed with nanoparticles such as Laponite to become shearthinning.

The printer is connected to a UV light and a stepper motor. Attached to the board are two on/off switches that are used to control the rate of extrusion. On the exterior, attachments are provided for separate light sources and a high definition (HD) camera that can monitor the process of printing. This camera can be connected wirelessly to other devices such as a laptop or a smartphone, allowing someone to monitor the printing process from a remote location. This has huge implications as it expands the capability of printing from a local scaffold delivery method to a long-distance monitoring system. A trained medical professional can apply his knowledge to any situation that this device is needed from a distant location.

Figure 3A:
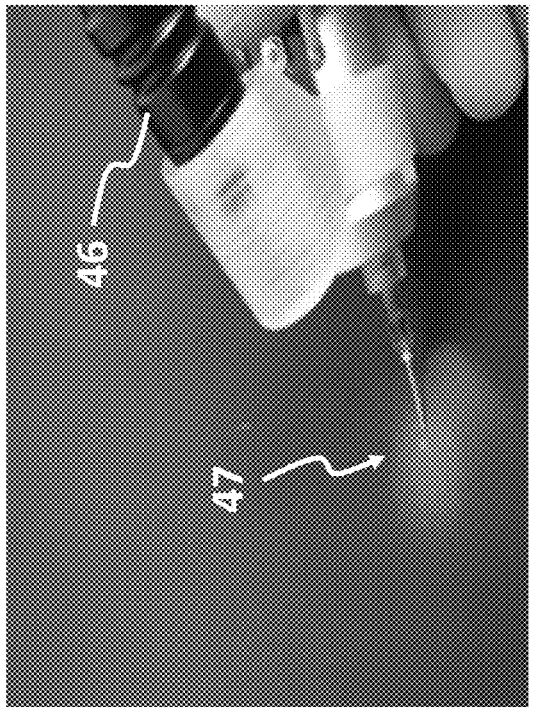
FIGS. 3A and 3B illustrate a handheld bioprinter fabricated with an integrated ultraviolet (UV) light source and camera for printing bioink and the assessment of the print quality according to embodiments of the disclosure.
Figure 3B:
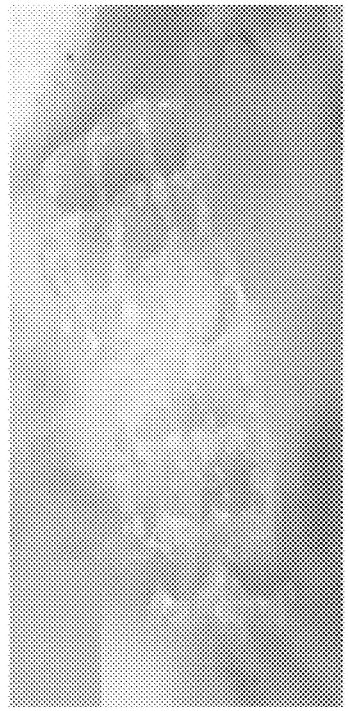
Figure 3C:
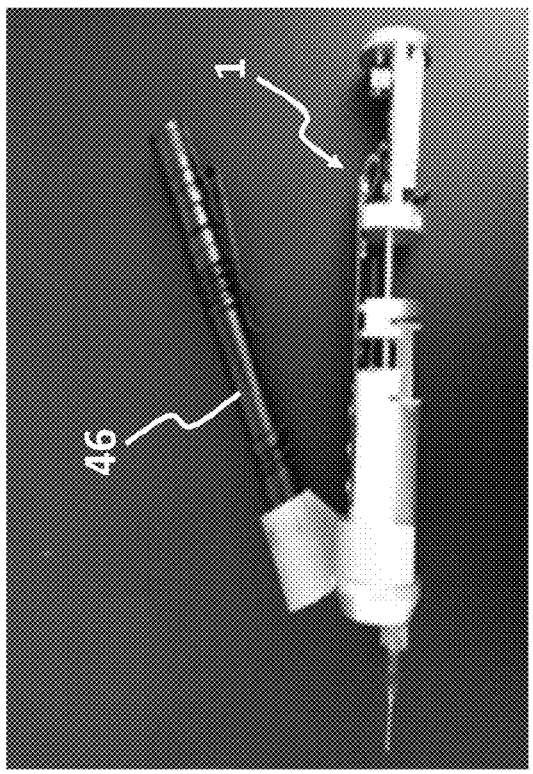
FIG. 3C illustrates a 3D scaffold fabricated from GelMA-based bioink according to an embodiment of the disclosure.
Figure 3D:
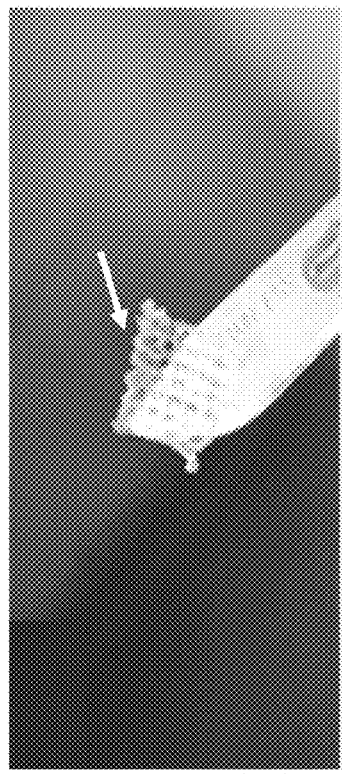
FIG. 3D illustrates in situ printing of GelMA on porcine skin showing conformal adhesion of the scaffolds to the tissue according to an embodiment of the disclosure.

FIGS. 3A and 3B show the handheld printer of Example 1 fabricated with integrated UV light source and camera for printing bioink and the assessment of the print quality. FIG. 3C shows a 3D scaffold fabricated from GelMA-based bioink according to Example 1. FIG. 3D shows in situ printing of GelMA on porcine skin showing conformal adhesion of the scaffolds to the tissue.

FIG. 4A shows the handheld printer with attached HD camera for in situ monitoring. FIG. 4B shows UV light curing capability attached to soft gel printer.

Figure 5:
FIG. 5 illustrates a view of the integrated HD camera on a smartphone display, which enables monitoring of the quality of printing by surgeons not physically present at the site according to an embodiment of the disclosure.

FIG. 5 shows a view of the integrated HD camera on a smartphone display, which enables monitoring of the quality of printing by surgeons not physically present at the site.

FIG. 6A shows pristine GelMA bioinks. These inks consist of GelMA and a photoinitiator (PI). GelMA has to be cooled to 4° C. to achieve proper viscosity for bio printing. FIG. 6B shows GelMA:Alginate (0.5%) formulation where alginate is crosslinked during printing with $CaCl_2$ fume followed by GelMA crosslinking after printing. FIG. 6C shows GelMA:Laponite (0.5%) bioinks. Laponite provides shear thinning properties and tunes bioink viscosity, it is biocompatible and biodegradable as well. After printing the structure, GelMA is crosslinked. GelMA can be crosslinked either with UV light or visible light. 2-hydroxy-4'-(2-hydroxyethoxy)-2-methyl propiophenone is used as photoinitiator for UV light and eosin Y is used as photoinitiator for the visible light.

Figure 7A:
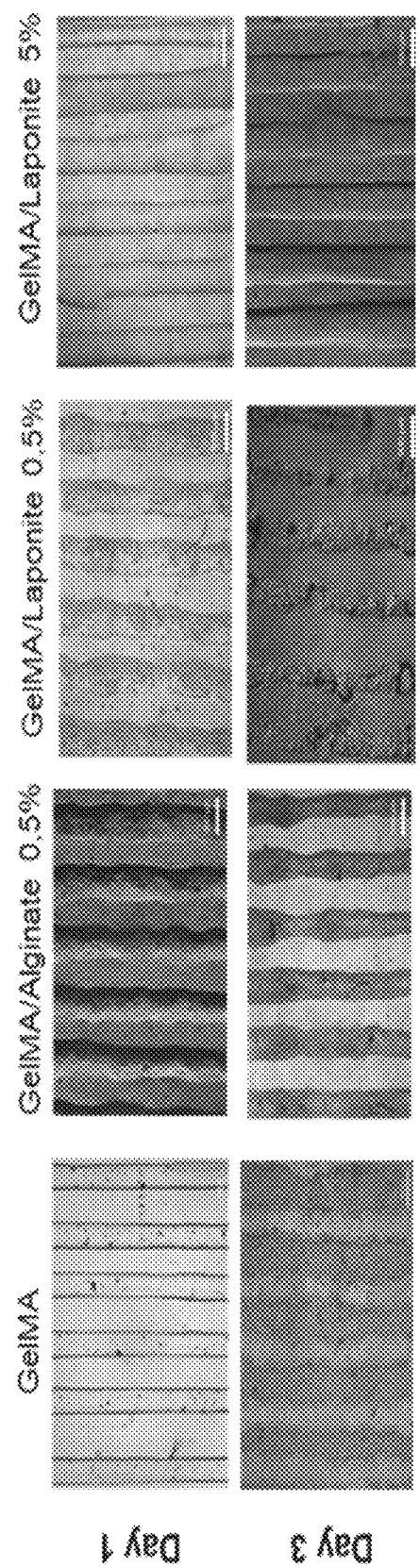
FIGS. 7A and 7B illustrate bioprinting of structures from different types of GelMA-based hydrogels according to embodiments of the disclosure.
Figure 7B:
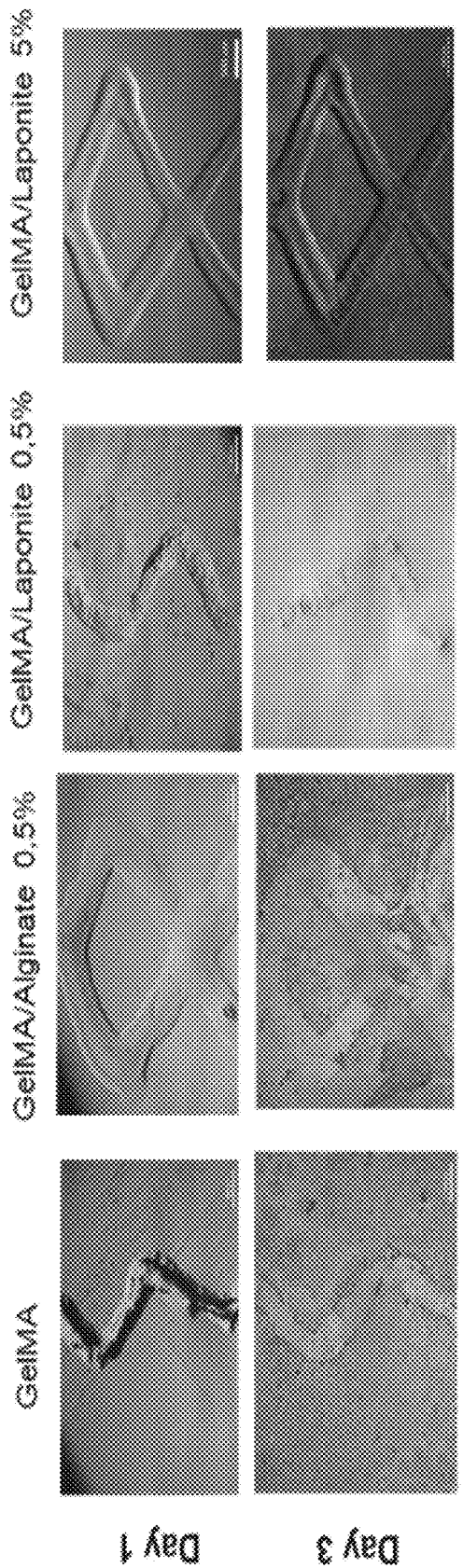

FIGS. 7A and 7B show bioprinting of structures from different types of GelMA-based hydrogels.

Figure 8A:
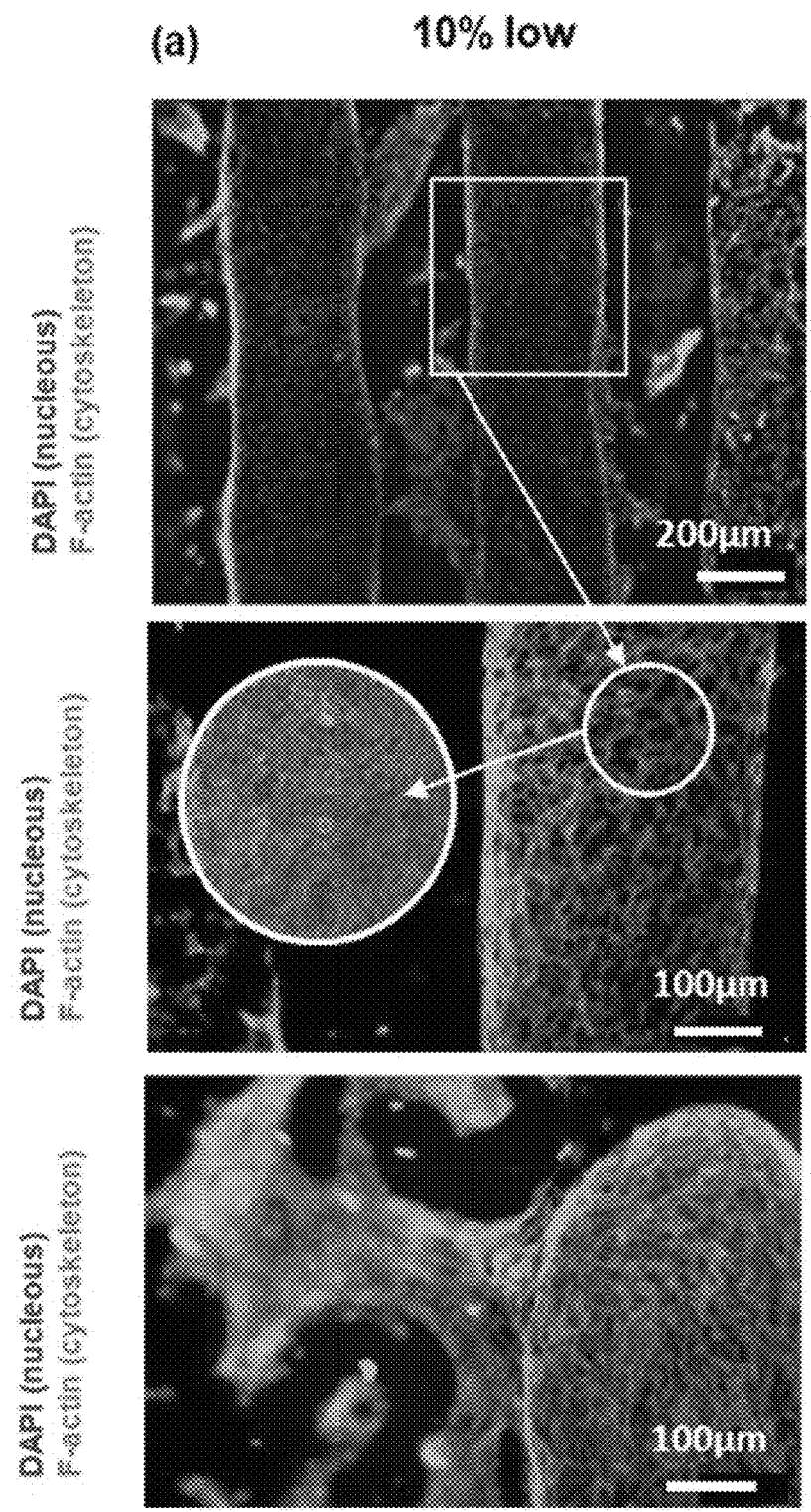
FIGS. 8A-8C illustrate assessments of the cellular morphology of 3D bioprinting GelMA hydrogels encapsulating C2C12 cells after 7 days in culture (F-actin and DAPI staining) according to embodiments of the disclosure.
Figure 8B:
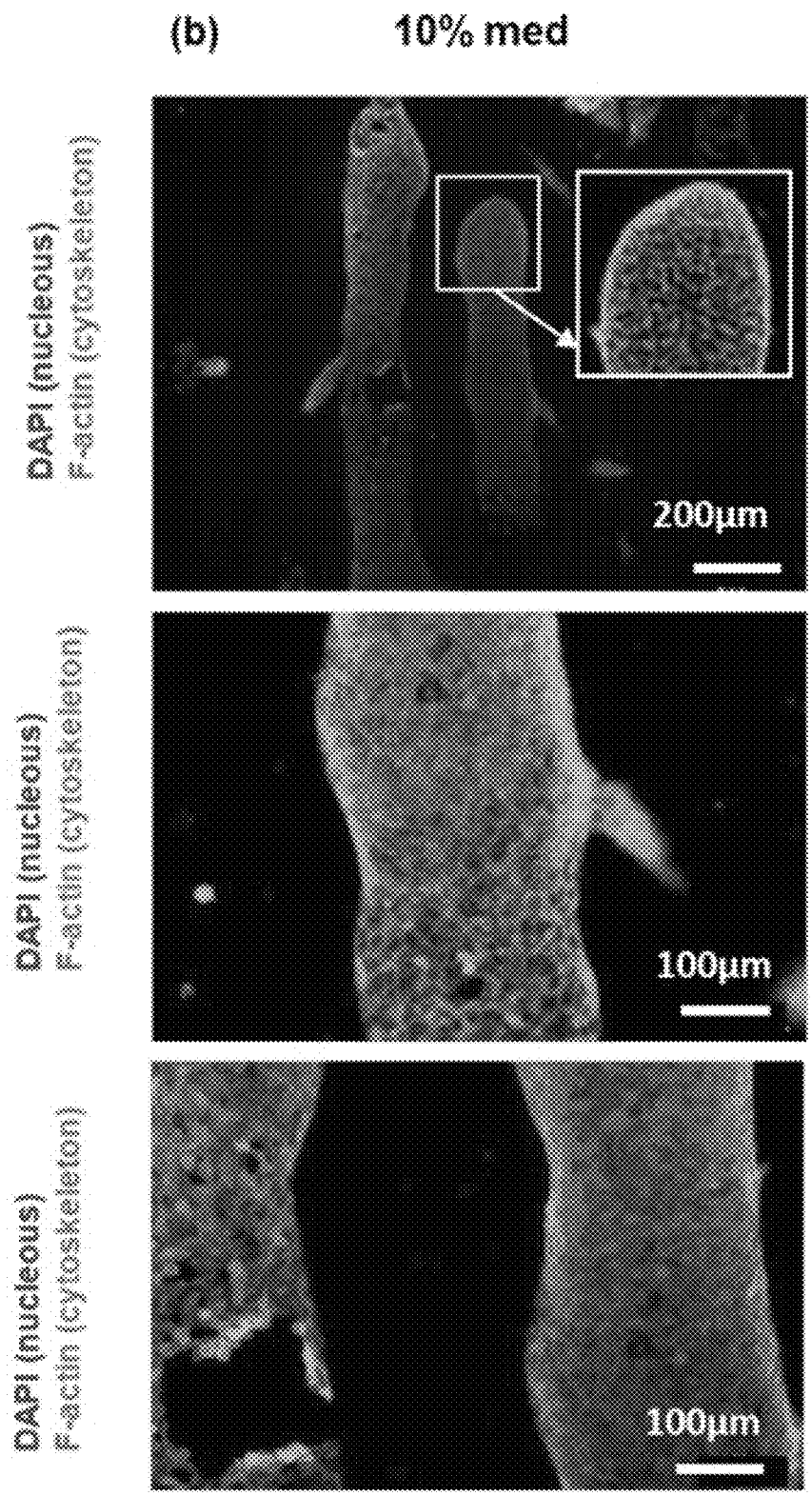
Figure 8C:
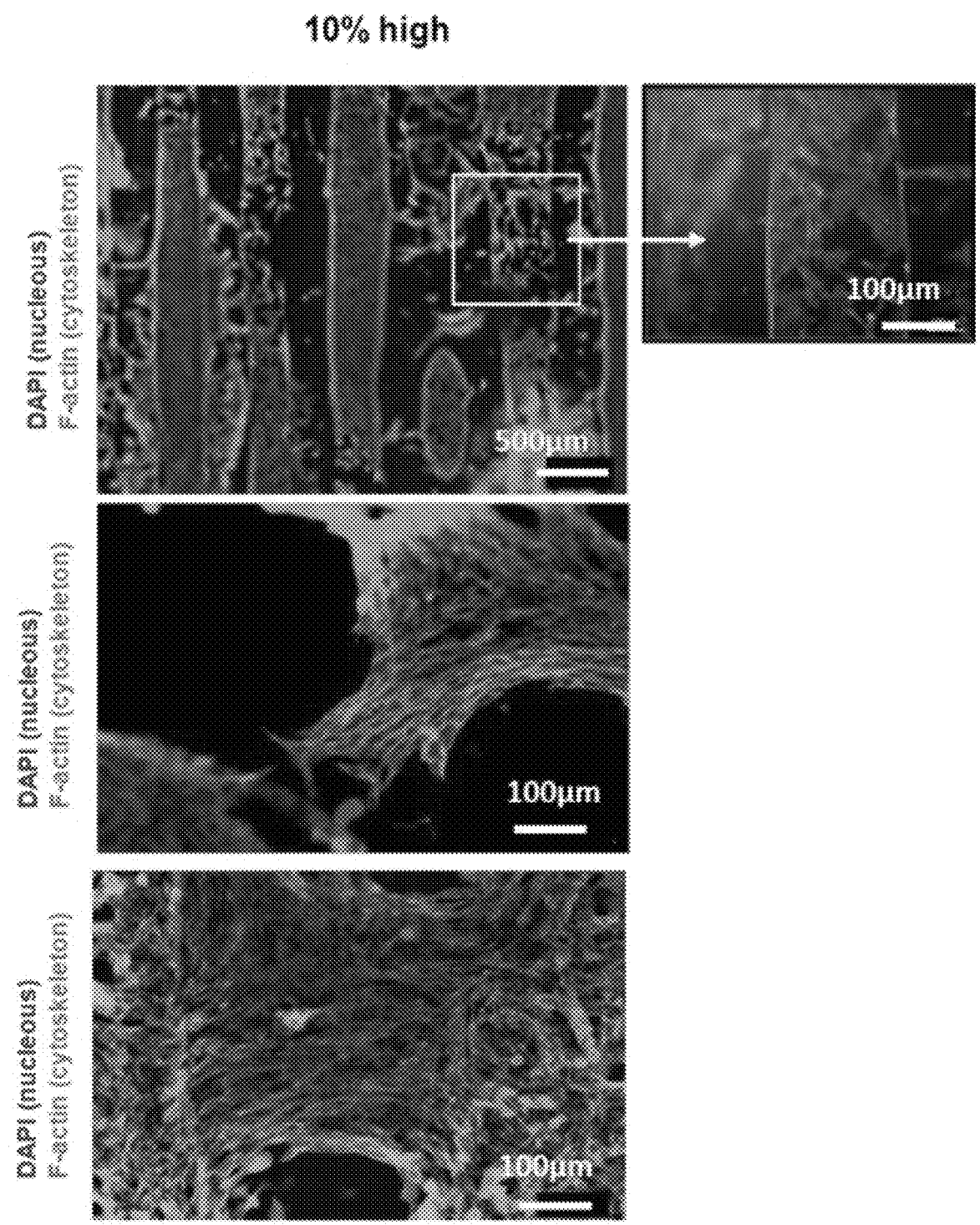

FIGS. 8A-8C show assessments of the cellular morphology of 3D bioprinting GelMA hydrogels encapsulating C2C12 cells after 7 days in culture (F-actin and DAPI staining). FIG. 8A shows 3D printing of cell-laden GelMA bioinks with 10% low methacrylation. FIG. 8B shows 3D printing of cell-laden GelMA bioinks with 10% medium methacrylation. FIG. 8C shows 3D printing of cell-laden GelMA bioinks with 10% high methacrylation.

Example 2

Figure 9A:
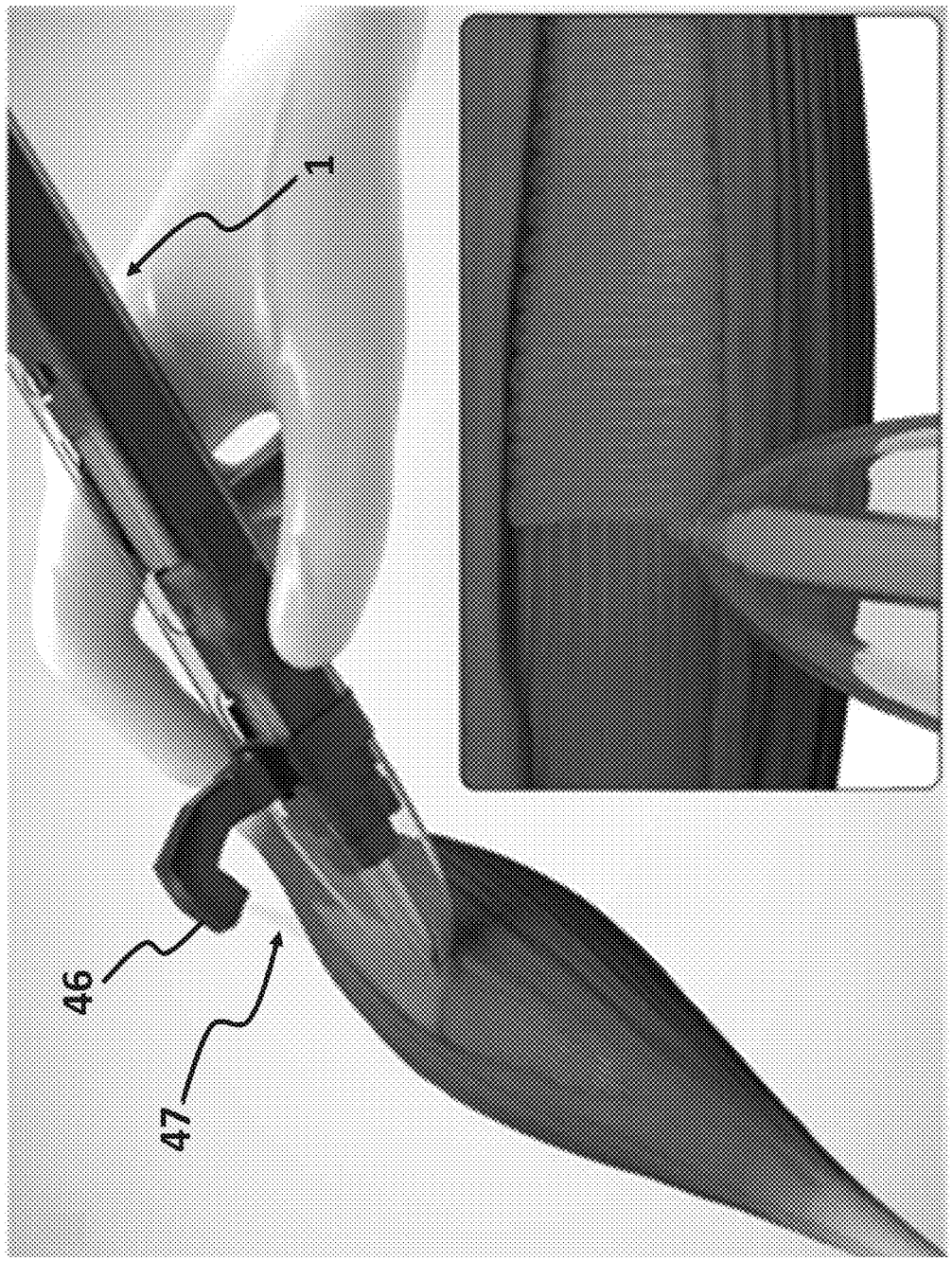

Current strategies for the treatment of VML injuries require acute stabilization of the patient, followed by delayed extremity reconstruction. Reconstructive operations include the implantation of autologous or allogeneic tissues. (13) Tissue engineering strategies, which have not yet been utilized in clinical practice, would also require a second surgical procedure to be implanted. However, an inflammatory reaction and loss of myogenesis factors following VML limit the regenerative capacity of the injured skeletal muscle. Without rapid intervention, the healing response of the body results in fibrosis rather than functional restoration of composite muscle tissue. (3) A robust strategy for VML treatment was created that can be utilized quickly, without the need for access to sophisticated surgical tools. FIGS. 9A-9D illustrate the utilization of a handheld bioprinter for in situ printing of scaffolds. FIG. 9A is a schematic diagram of the in situ bioprinting of cell-laden GelMA hydrogels for the treatment of VML injuries. FIG. 9B is a photograph of the utilized handheld 3D bioprinters equipped with a UV light source for in situ crosslinking of the printed scaffolds. FIG. 9C is a photograph of a bioprinted scaffold printed on a non-flat porcine skeletal muscle. FIG. 9D is a photograph of an N-shaped scaffold printed on a glass slide using the device of FIG. 9B, demonstrating the ease of printing of scaffolding with desired architectures. The disclosure provides a simple yet effective, portable, extrusion-based bioprinter, which is capable of in situ printing and crosslinking of photocrosslinkable bioinks (FIGS. 9A and 9B). This fully portable, partially automated bioprinter overcomes a number of challenges associated with existing stationary bioprinters, such as their inability to print on non-flat surfaces, limited scalability to print clinically-relevant scaffolds, and the challenge in creating scaffolds with proper adhesion to native tissues. None of the existing bioprinters or in situ bioprinters are capable of collectively addressing all these challenges.

Figure 10:
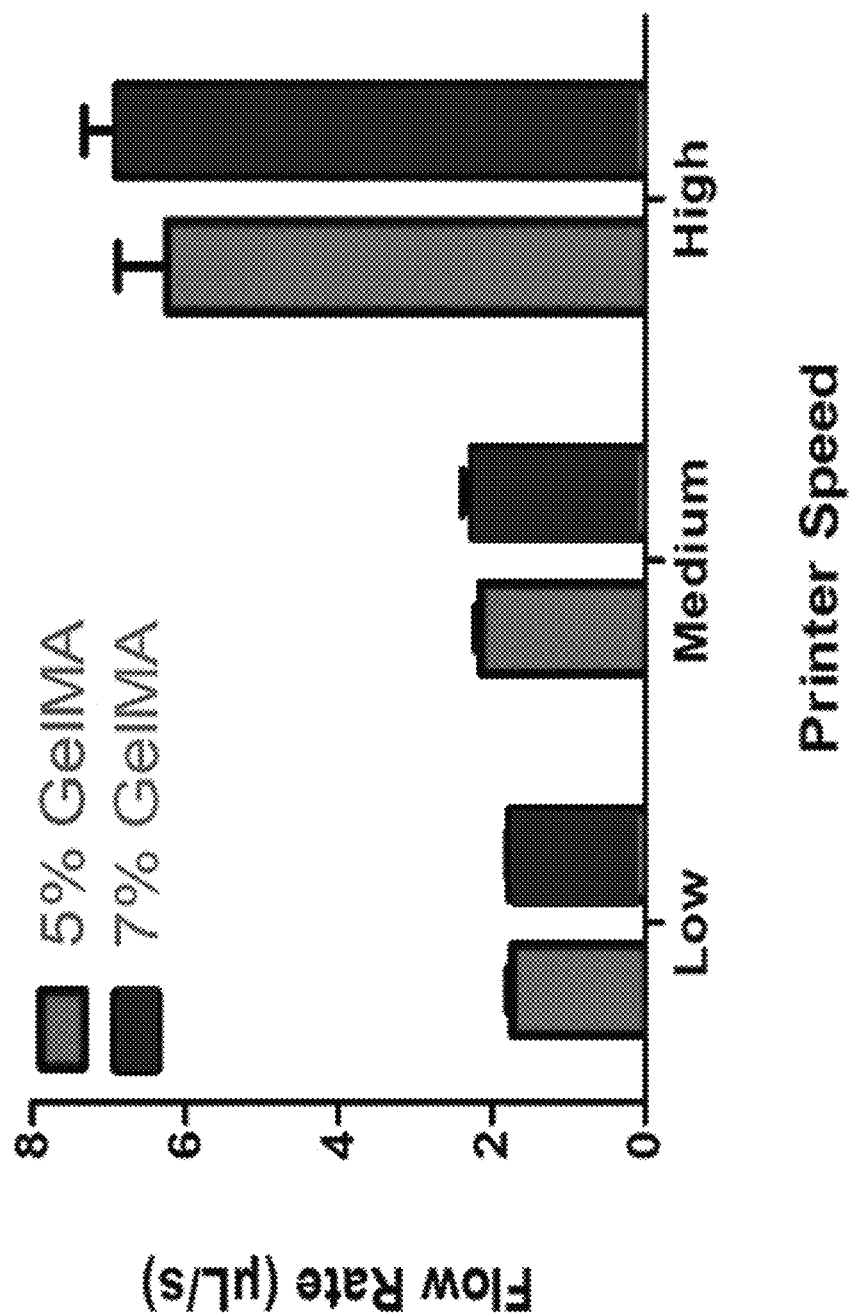
FIG. 10 is a plot of flow rate versus printing speed according to embodiments of the disclosure.

Syringes containing bioinks were loaded into the partially automated bioprinter, and a DC motor actuated a platform fitted to the syringe plunger flange to extrude the syringe contents. The extrusion rate of the bioink could be controlled by adjusting the speed of the DC motor. The printer has an integrated UV light-emitting diode pen that enables the rapid crosslinking of extruded photocrosslinkable bioinks. In this study, GelMA was used as the bioink due to its ability to be rapidly crosslinked, similarity to the collagen component of ECM in skeletal muscles, and its suitability for skeletal muscle tissue engineering. (35, 36) GelMA also adheres to various tissues if directly crosslinked on their surface. (33, 34) The partially automated bioprinter can be used for creating scaffolds with various architectures and filling cavities and defects that match the injury site in skeletal muscles (FIG. 9C). Another key advantage of the handheld partially automated bioprinter over its stationary counterparts was the possibility of printing on non-flat surfaces, which allows for conformation to the topographic conditions of injured skeletal muscle (FIG. 9C). The partially automated bioprinter is easy to maneuver and can be used to create highly defined architectures (FIG. 9D). The extrusion rate could be adjusted by changing the frequency of the electrical motor activation (FIG. 10). At each of the low, medium and high coding inputs for the controller of the electric actuator, the flow rate for 5% and 7% GelMA formulations was comparable, with the flow rate being ~0.6 µL/s greater for the 7% GelMA formulation as compared to the 5% GelMA formulation at the high coding input, as shown in FIG. 10.

The nozzle size, nozzle type, and extrusion rate were evaluated to create the best resolution for printing structures of 5% and 7% (w/v) GelMA. By varying nozzle size (400 µm and 600 µm for 5% and 7%, respectively), multilayered scaffolds could be printed with excess pressure minimally affecting the resolution of the print, providing the consistent ability to print well-defined filaments. Blunt tip and tapered tip needles were also evaluated, for the speed at which we are printing it was found that tapered tip needles printed more defined structures. Overall, the printer is significantly faster in the deposition of the scaffolding materials. More importantly, because there is no need to perform surgery to implant the printed scaffolds in comparison to conventional printers, the disclosed approach is much faster in reaching the patient. In addition, the syringe cartridge of the disclosed printer is easy-to-change and enables printing multiple centimeter-scale scaffolds.

Example 3

The physical and mechanical properties of GelMA can be changed by varying the degree of methacrylation, prepolymer concentration, temperature, photoinitiator (PI) concentration, and the light exposure time and intensity. (37) In the disclosed handheld partially automated bioprinting system, each of the bioink input variables was selected to match the necessary biological and mechanical properties of native skeletal muscle. Following established literature, the use of medium level methacrylate GelMA is mechanically and biologically suitable for muscle tissue engineering applications. (35) The lithium phenyl-2, 4, 6-trimethylbenzoylphosphinate (LAP) was used as the PI, and its concentration was selected to be 0.067% (w/v) following the previous literature. (37) The exposure time selected for printed scaffolds was 20 seconds (the estimated time that printed hydrogels are directly exposed to light). The light wavelength was 365 nm with a flux of 120 lumens at an emitted distance of 45 mm; the intensity of the light was calculated to be 493 W/m2. Thus, the major parameter that was varied throughout our experiments was the concentration of GelMA within the bioink. Initial experiments showed that stable scaffolds could be printed using the disclosed handheld partially automated bioprinter from GelMA hydrogels with the concentrations of 5% (w/v) and above. Consequently, attention was focused on two GelMA concentrations of 5% and 7% (w/v), which are widely used for the fabrication of tissue engineering scaffolds. (38, 39).

Figure 11A:
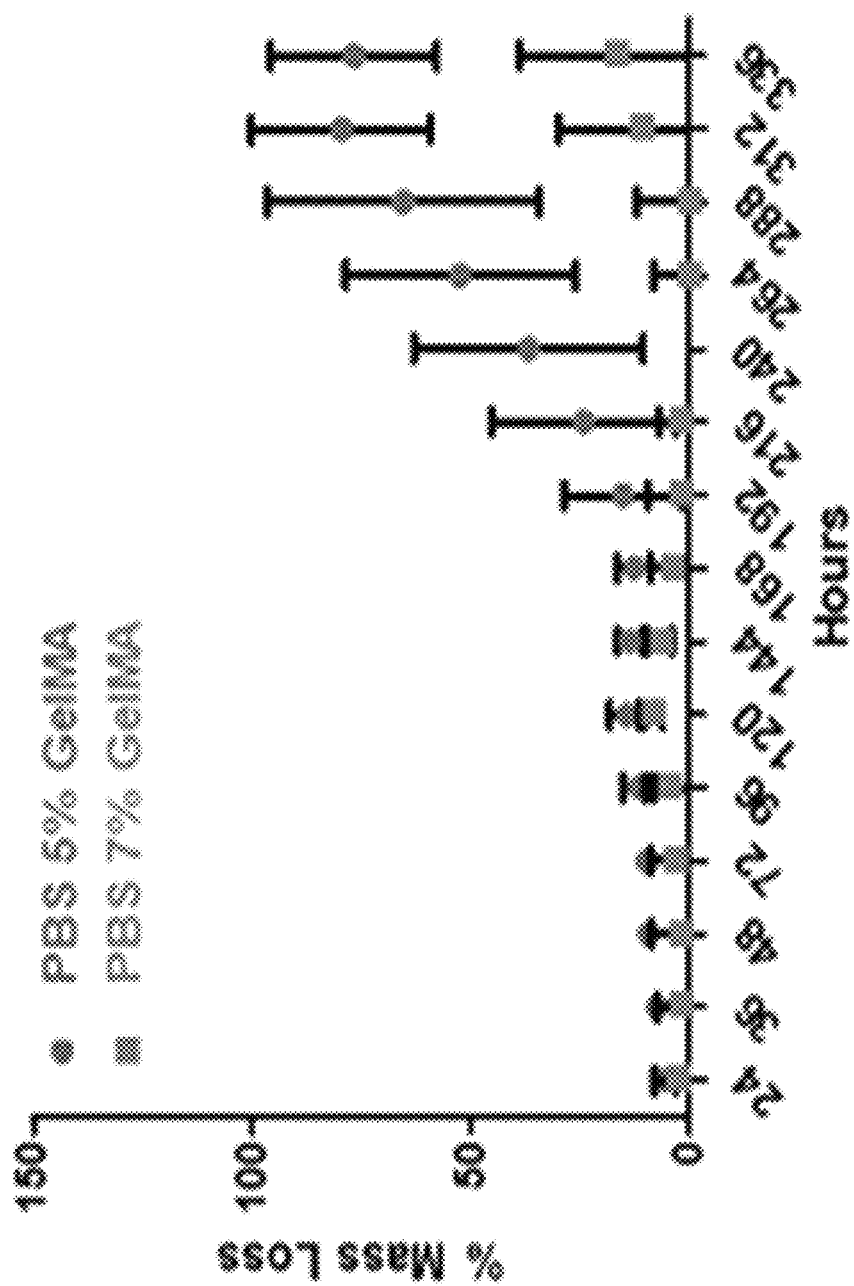
FIGS. 11A-11L illustrate physical characterization and ex vivo adhesion strength and shear strength of GelMA printed hydrogels according to embodiments of the disclosure.
Figure 11B:
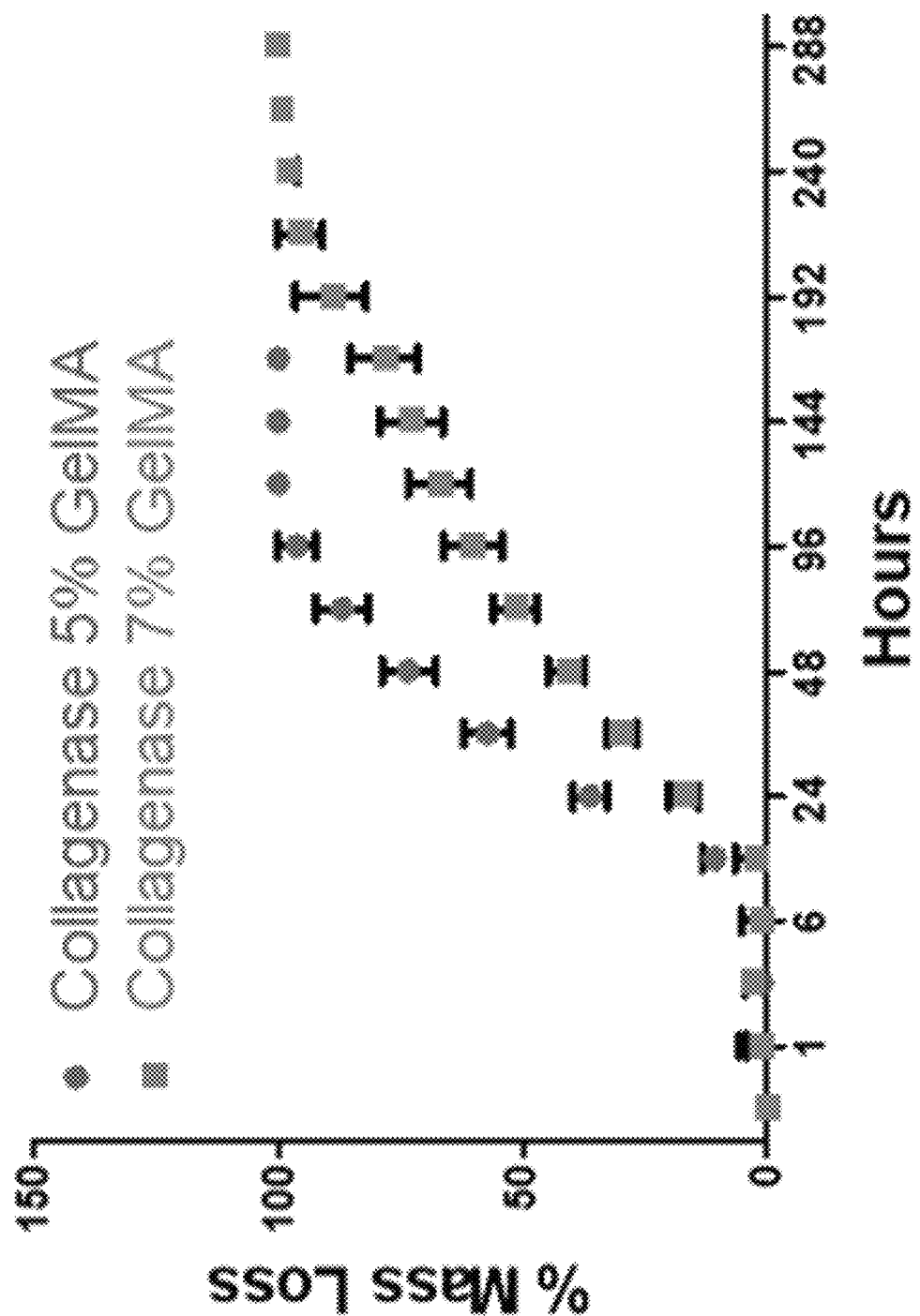
Figure 11D:
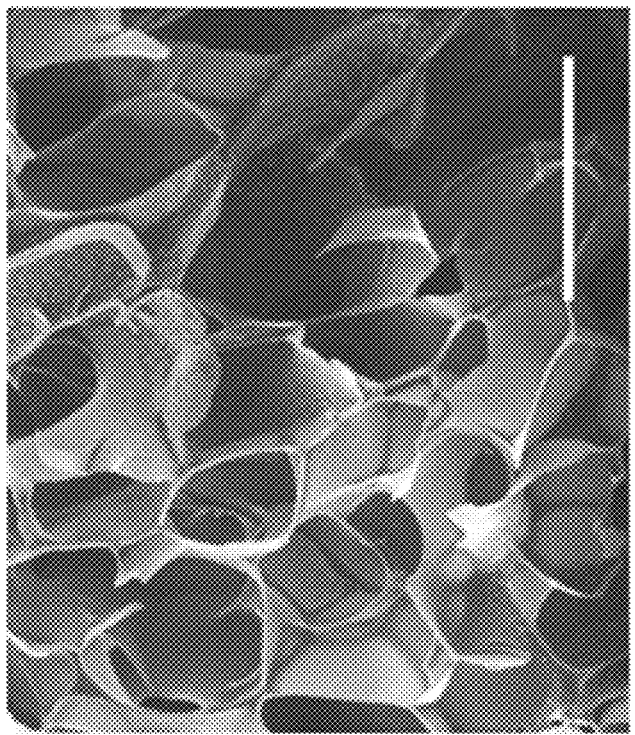

The degradation of GelMA hydrogels was measured by placing crosslinked GelMA hydrogel disks in Dulbecco's Phosphate Buffer solution (DPBS) with and without collagenase, the enzyme responsible for the degradation of collagen-derived materials in vivo. FIGS. 11A-11L show the physical characterization and ex vivo adhesion strength and shear strength of GelMA printed hydrogels. The 5% and 7% (w/v) GelMA hydrogel disks remained stable in DPBS at 37° C. without collagenase for about 8 days. After 8 days, significant degradation was observed for the 5% (w/v), while the degradation rate of 7% (w/v) GelMA hydrogel disks was slower (FIG. 11A). The degradation of 10 mm diameter and 4.5 mm tall cylinders in 1% (w/v) collagenase type I solution (1.5 µg/mL) showed that both the crosslinked 5% and 7% (w/v) GelMA disks started to degrade after 12 hours and were completely degraded after 4 and 10 days respectively (FIG. 11B). These results show that the degradation rate of the hydrogels can be tuned by adjusting the GelMA concentration.

The internal microstructure of the crosslinked GelMA samples was analyzed via a scanning electron microscope (SEM). The morphology of the lyophilized hydrogels is different from in a hydrated state, but the overall structure remains the same. The microstructure of the 5% (FIG. 11C) and 7% (FIG. 11D) cross-linked GelMA hydrogels was morphologically similar, having pores larger than 1 µm, which facilitates mass transfer and cellular infiltration. Each structure has pore sizes ranging from hundreds of nanometers to a couple of micrometers. The structure of the hydrogels allows mass transfer and cellular encapsulation and migration during proliferation and differentiation.

Figure 11C:
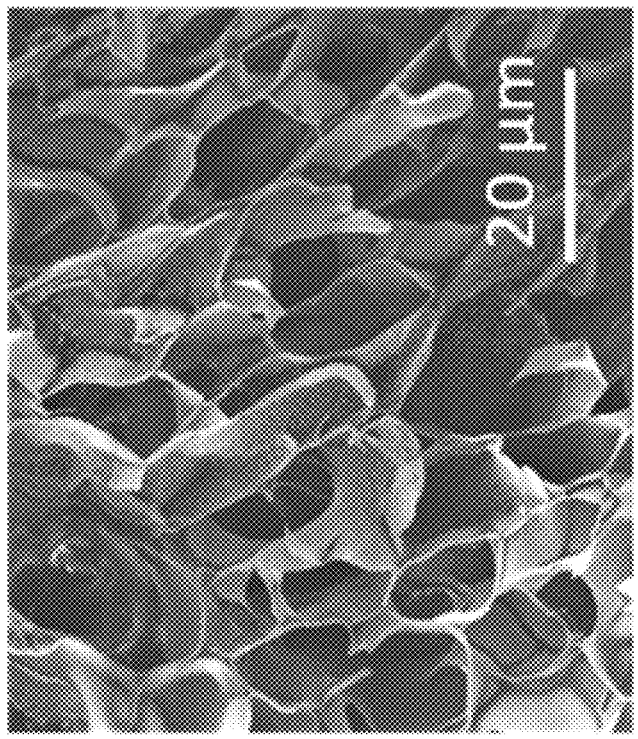
Figure 11E:
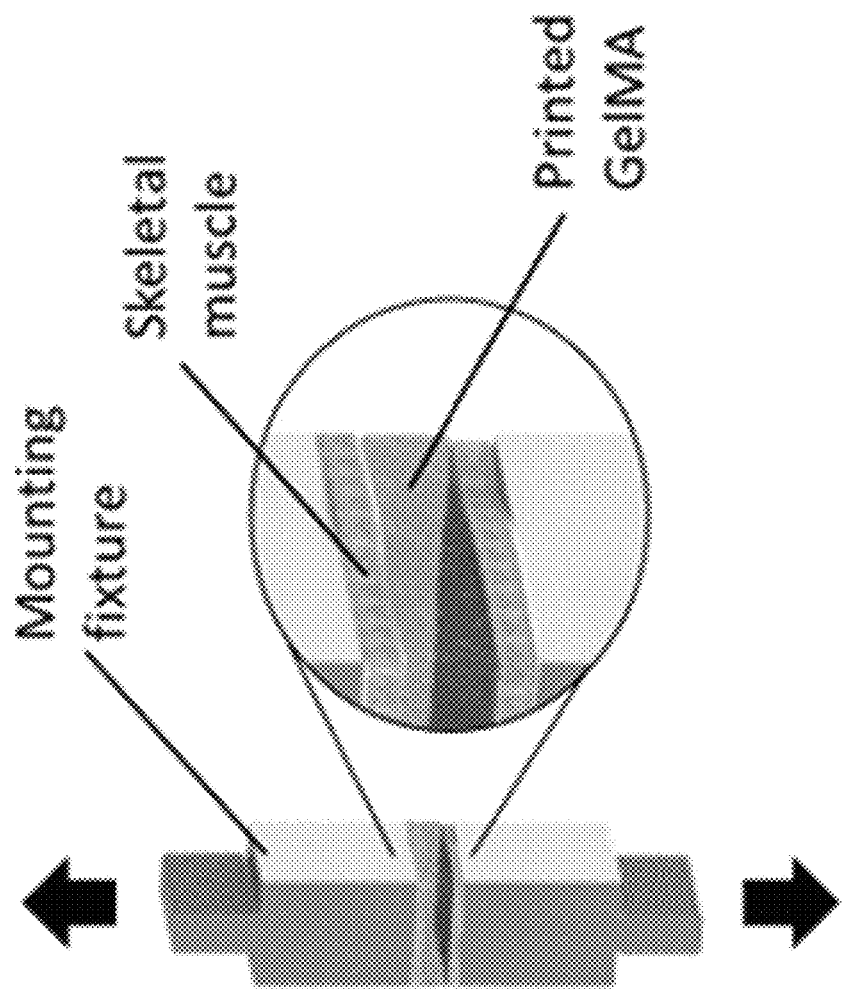
Figure 11G:
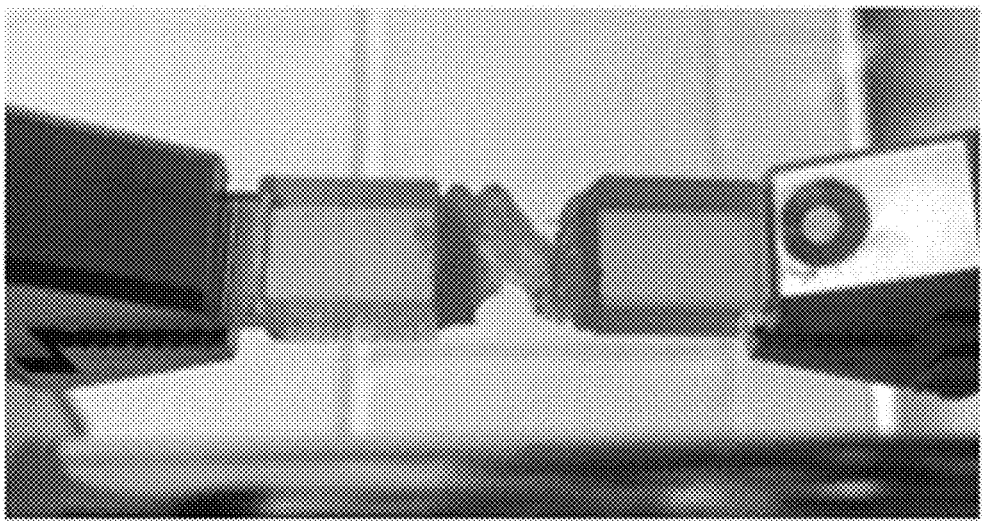
Figure 11F:
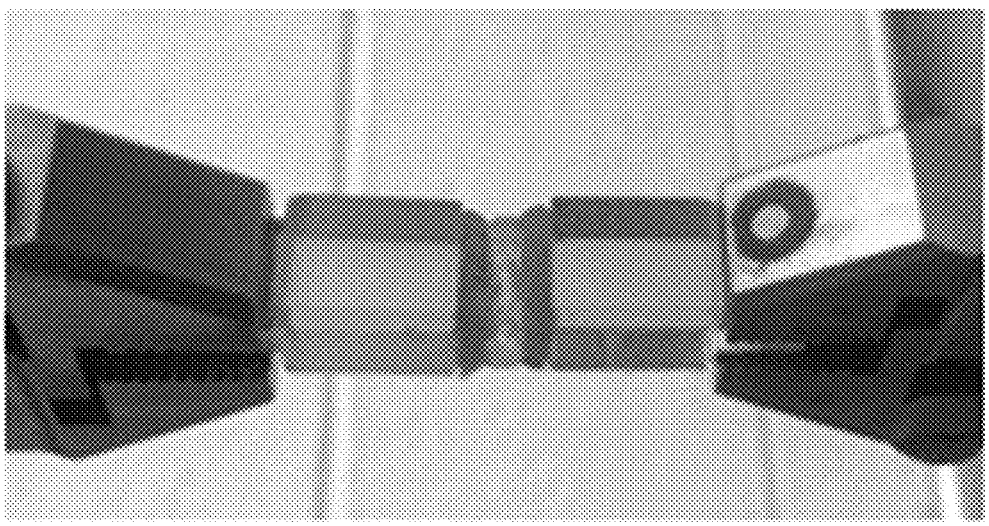
Figure 11H:
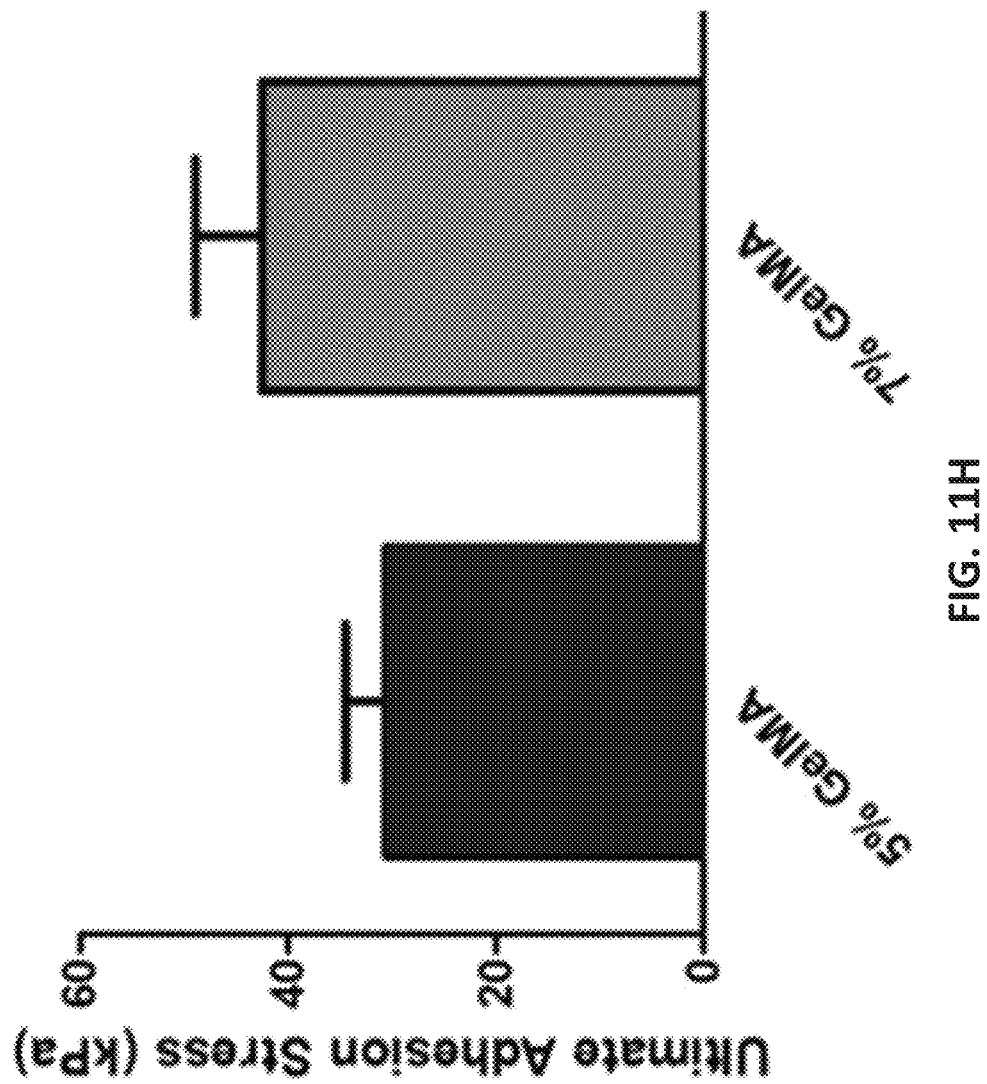
Figure 11I:
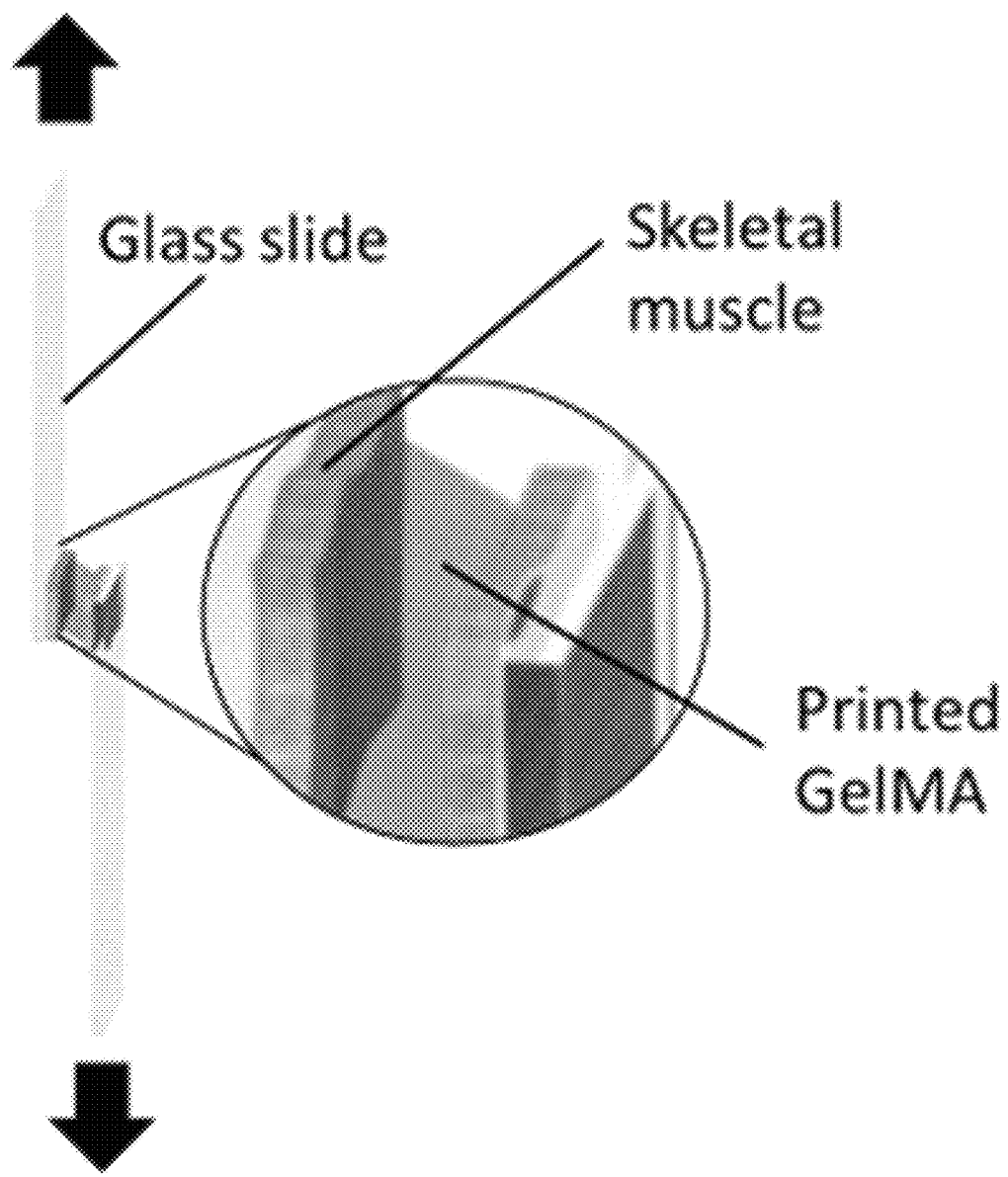
Figure 11K:
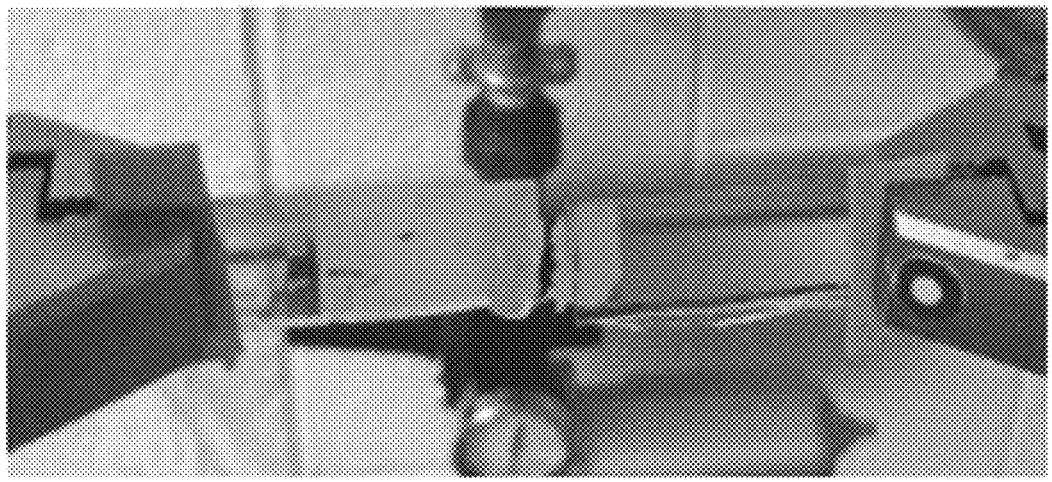
Figure 11J:
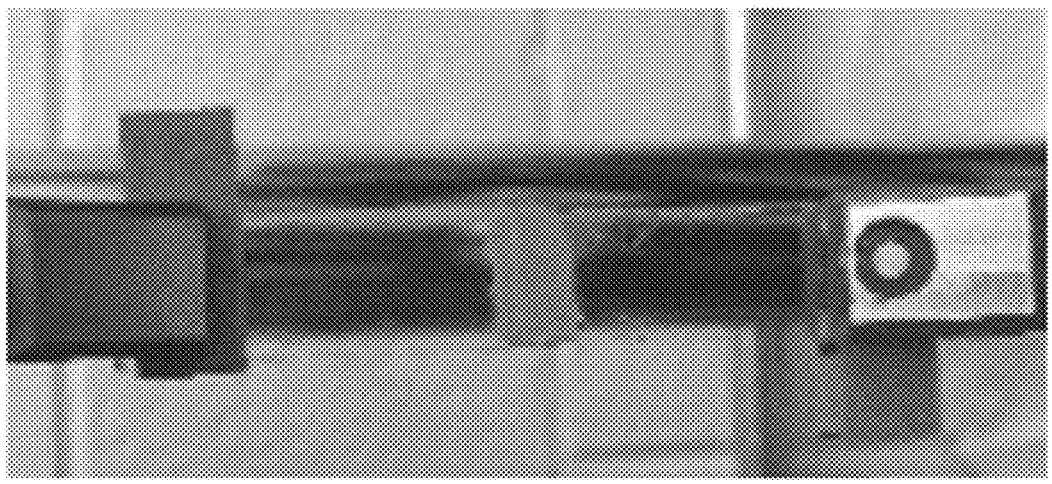
Figure 11L:
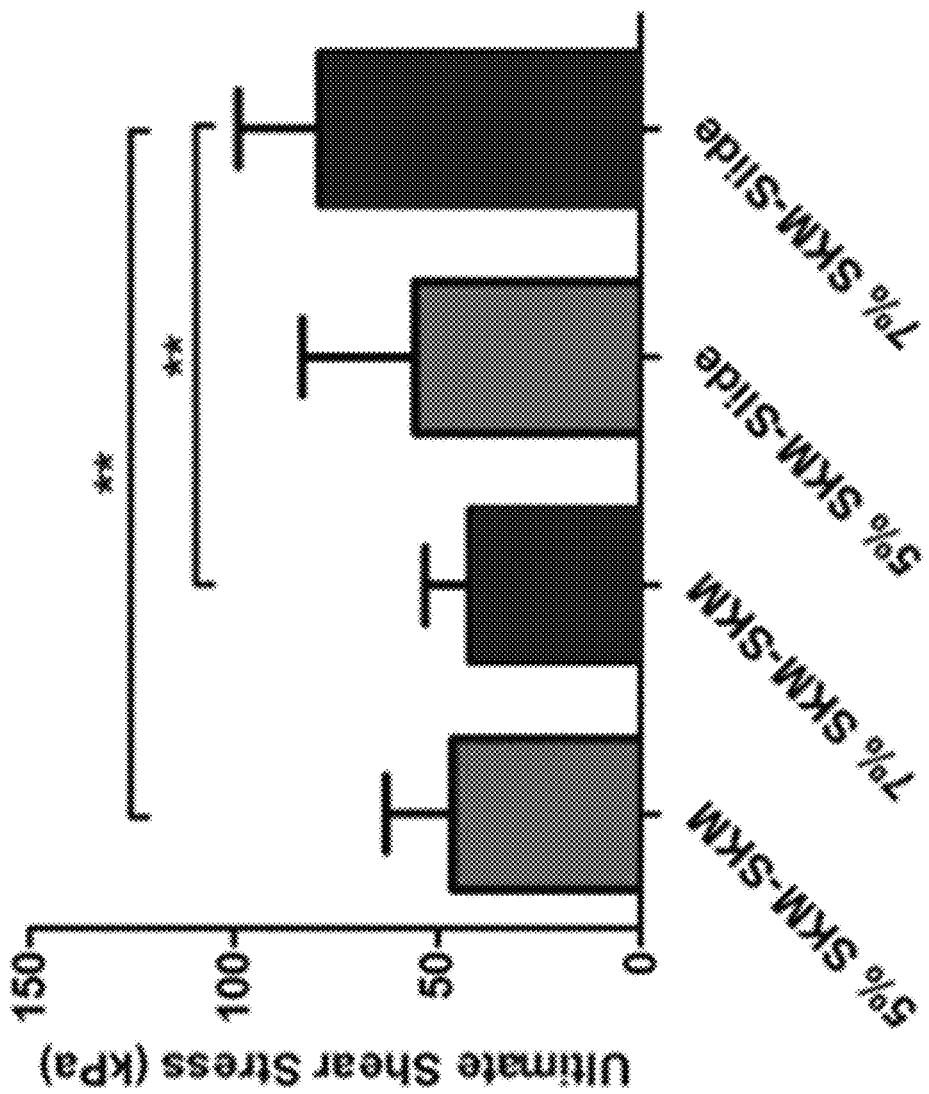

In order to act as a suitable scaffold for the recruitment of native cells, an implanted construct for VML must adhere to the surrounding tissue and support compressive loads during muscle contraction and relaxation. It has been shown that if GelMA is directly crosslinked at the interface of tissues, it adheres well with the tissue. To analyze the mechanical adhesion strength, normal and shear adhesion tests were conducted between the GelMA hydrogels and various substrate conditions. The normal adhesion stress was measured by printing the GelMA hydrogels and crosslinking them between two pieces of porcine skeletal muscle that were each previously fixed to two adapting fixtures (FIG. 11E). The crosslinked structures were stretched until failure and separation between the tissue and the hydrogel occurred (FIGS. 11F and 11G). FIGS. 11E-11G show the set up following ASTM F2458-05. (42). FIGS. 11I-11K show the set up following ASTM F2255-05. (43) The ultimate adhesion strength increases as GelMA concentration increases from 5% (w/v) (30.6+3.9 kPa) to 7% (w/v) (42.4±6.5 kPa) (FIG. 11H). This value is within the range of mechanical loads recorded in skeletal muscle of animal model. (40) The shear adhesion strength was measured by printing and crosslinking of GelMA hydrogels between substrates of two varying conditions: skeletal muscle adhered to glass slides on both sides (SKM-SKM), as well as skeletal muscle adhered to a glass slide on one side and 3-(Trimethoxysilyl) propyl methacrylate (TMSPMA)-coated glass slide on the other (SKM-Slide) (FIG. 11I). The first condition was representing the corners of the defect site in which the scaffolds is confined by the surrounding tissue, while the latter case represented the middle section where the scaffold has one interface with the host tissues. The glass slides with the various substrate conditions and crosslinked bioinks were also stretched until failure, and full separation occurred (FIGS. 11J and 11K). The ultimate shear adhesion stress to skeletal muscle tissue was approximately 53 kPa for the 5% (w/v) and 74 kPa for the 7% (w/v) GelMA (FIG. 11L), which is comparable to the typical mechanical loads reported in animal models. (40)

Figure 12A:
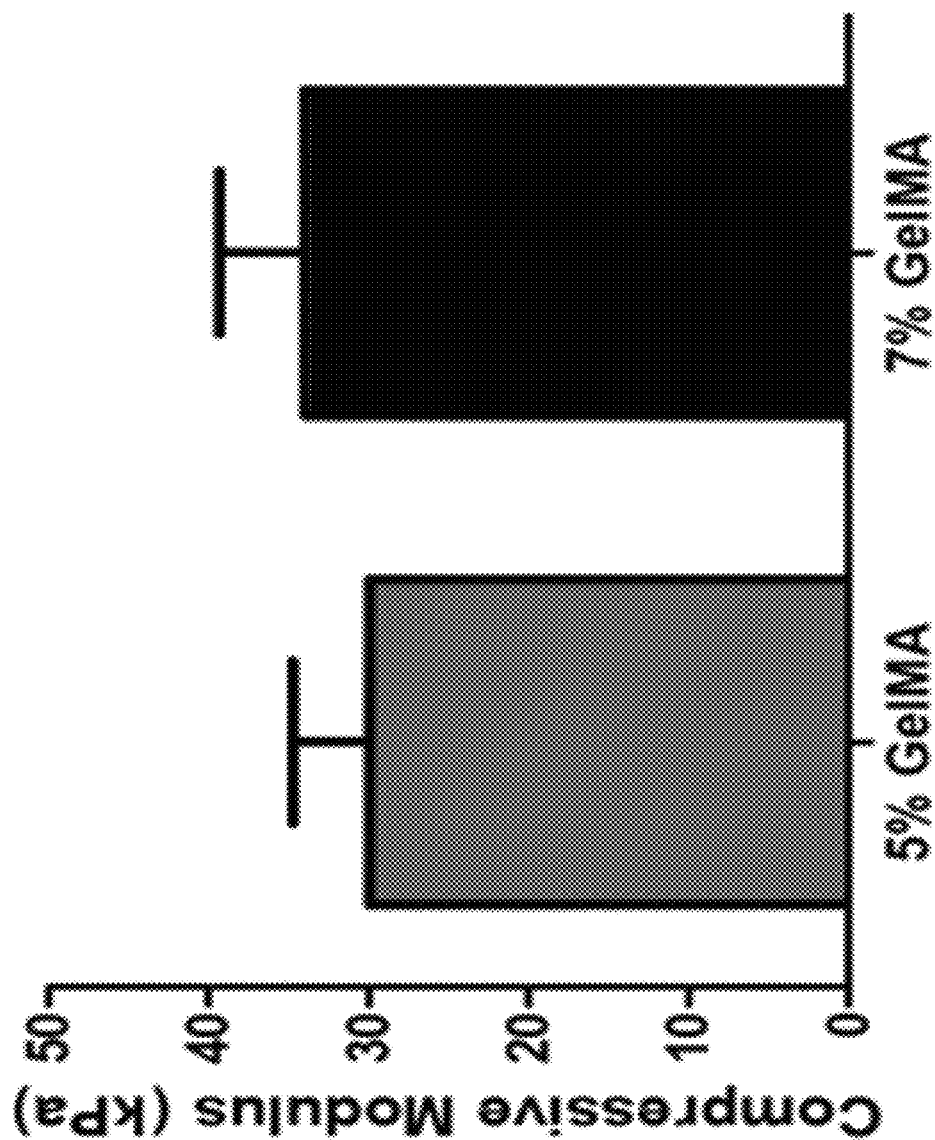
FIG. 12A is a plot of compressive modulus versus percent (%) GelMA according to embodiments of the disclosure.
Figure 12B:
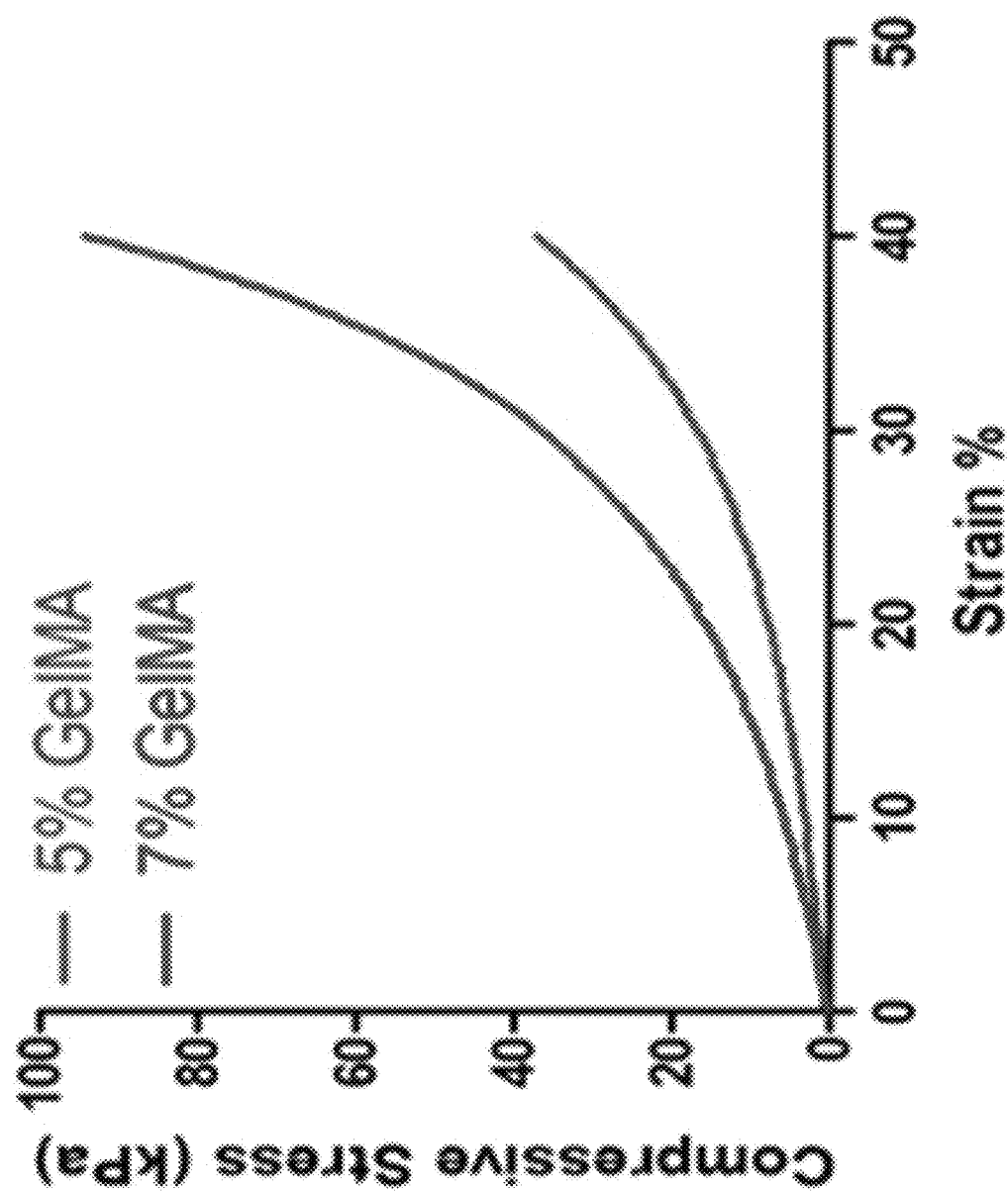
FIG. 12B is a plot of compressive stress versus strain % for 5% GelMA and 7% GelMA hydrogel formulations according to embodiments of the disclosure.

Since the scaffolds were being printed at the flexed state in the real application, they would experience compressive forces during the muscle contraction. Thus, the mechanical properties of GelMA in response to compressive mechanical forces were determined. The compressive modulus and ultimate compressive strength of 5% and 7% (w/v) GelMA hydrogels followed a similar trend seen with the adhesion and shear adhesion tests. As GelMA concentration increases the modulus and strength also increases. The compressive modulus increased from 5% (w/v) GelMA (30±5 kPa) to 7% (w/v) GelMA (34±5 kPa) (FIG. 12A). These values are comparable to the values for skeletal muscles of rodents reported in the literature. (41) The representative stress-strain curves in FIG. 12B clearly exemplify the trend seen between 5% and 7% (w/v).

Figure 13A:
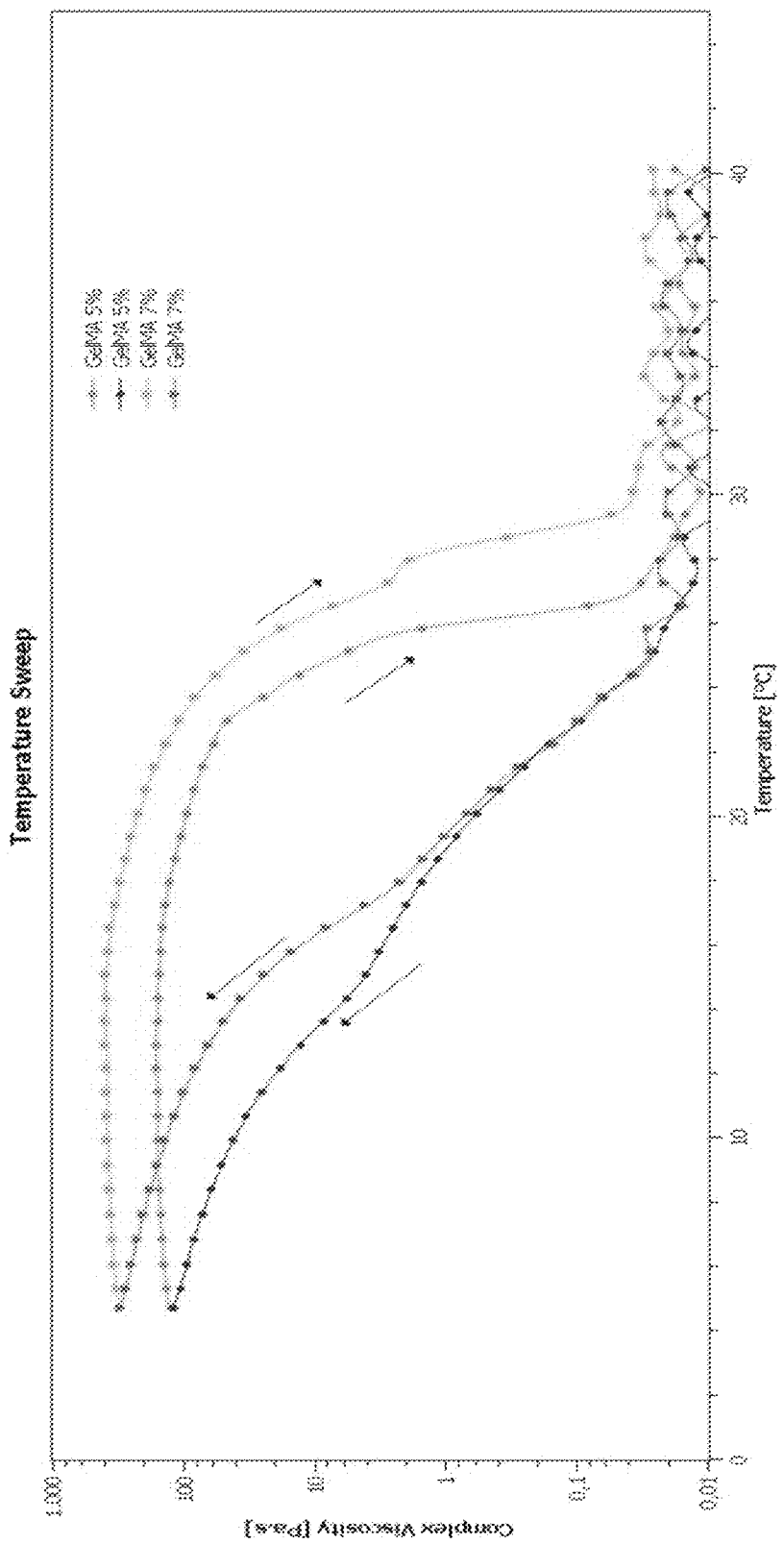
FIGS. 13A-13C are plots of rheological measurements of 5% and 7% (w/v) uncrosslinked GelMA hydrogel formulations according to embodiments of the disclosure.
Figure 13B:
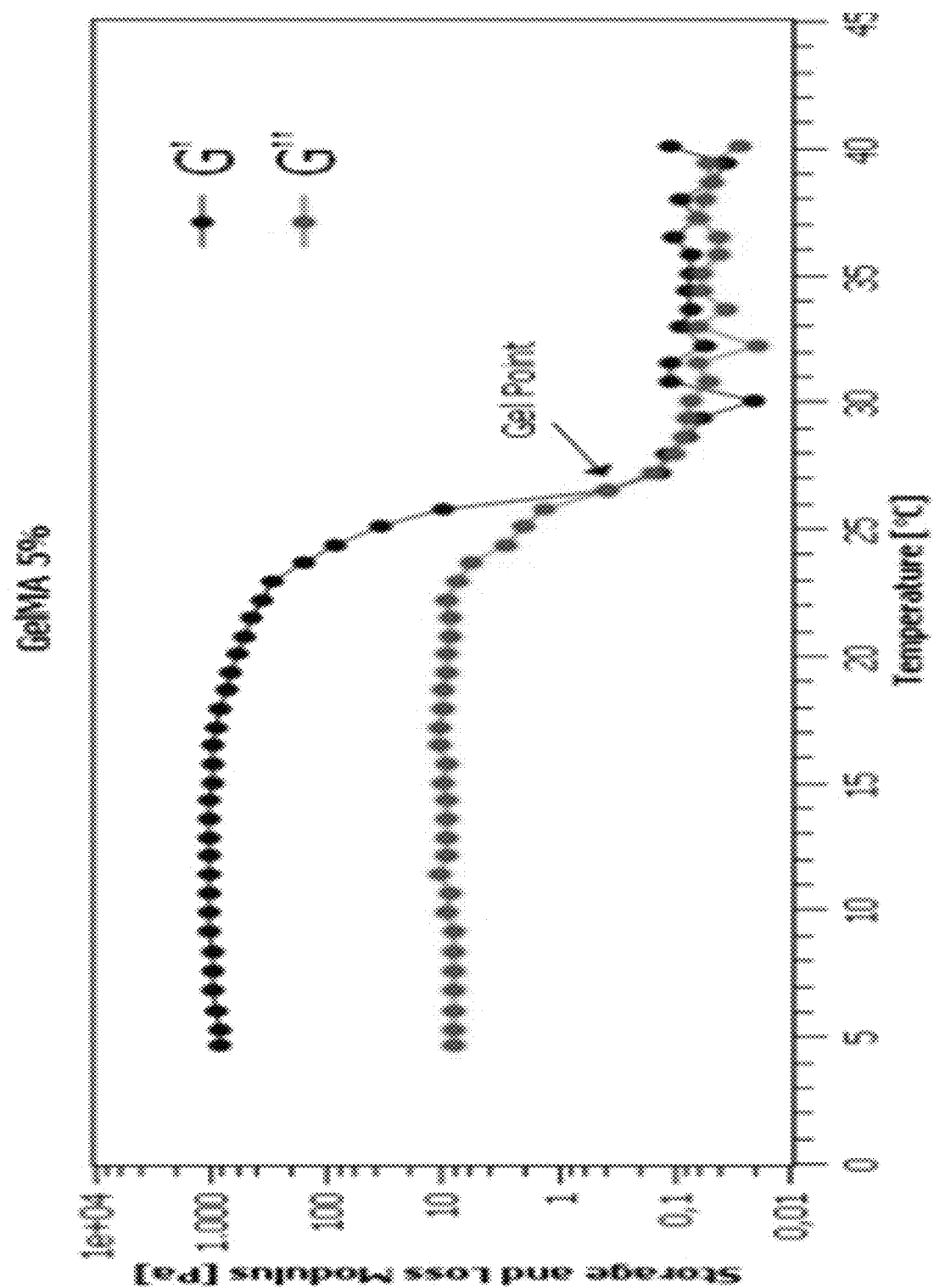
Figure 13C:
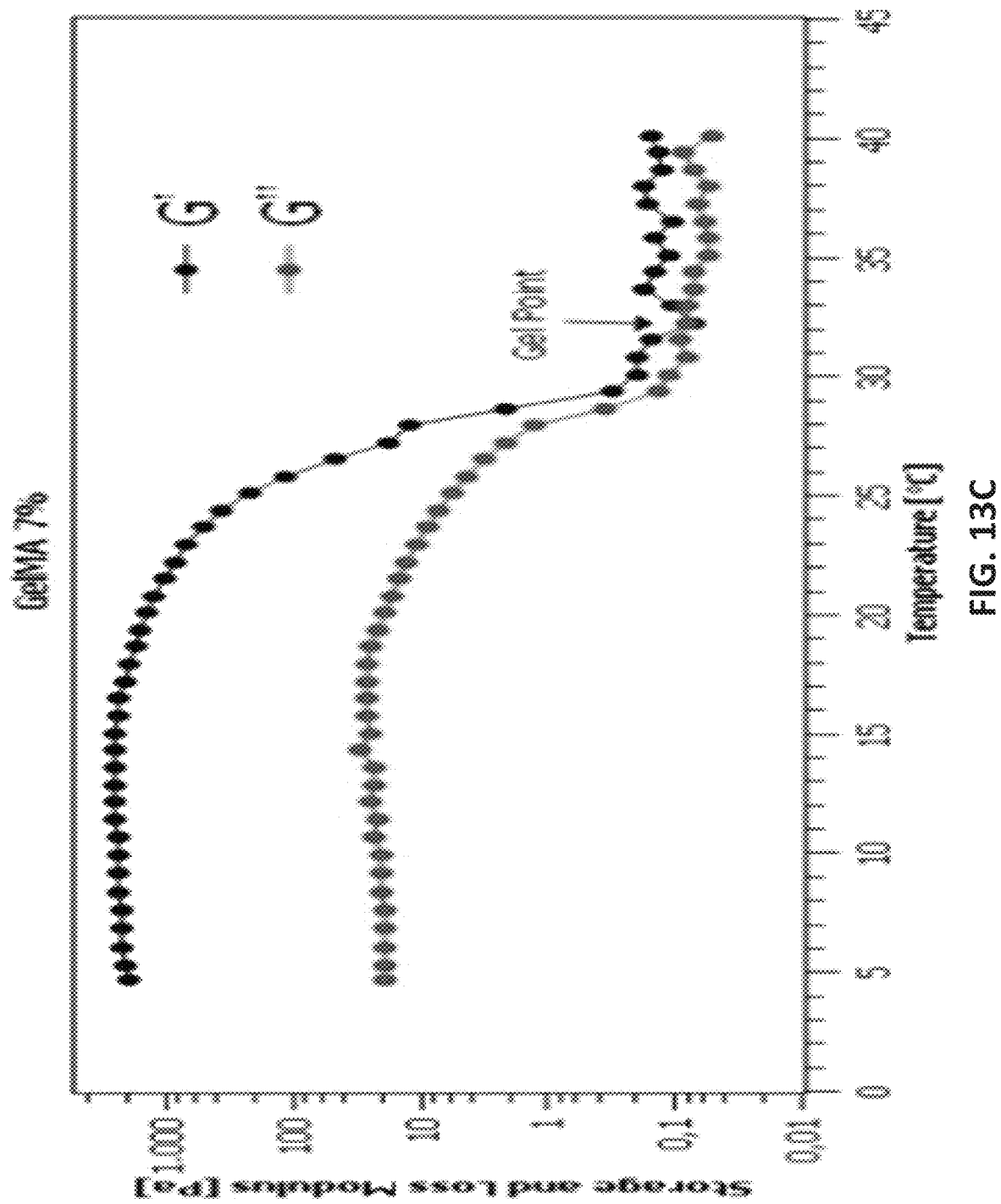

In order to investigate the printability of GelMA hydrogels, the rheological analysis was performed. Rheological measurements for 5% and 7% (w/v) uncrosslinked GelMA confirmed that the viscosity at room temperature was nearly zero resulting in droplet formation rather than fiber deposition (FIGS. 13A-11C). FIG. 13A shows a temperature sweep to measure complex viscosity of non-cross-linked 5% and 7% (w/v) GelMA hydrogel solutions in oscillatory mode from 4 to 37° C., at a constant frequency, shear rate and strain of 1 Hz, 3 s$^{-1}$, and 1%, respectively. Temperature sweep profiles of 5% and 7% (w/v) GelMA, show that the viscosity is decreasing by increasing the temperature (FIG. 13A). This shows the necessity of incubation of gel at 4° C. before the printing as the viscosity of both gels at room temperature is nearly zero and to reach to suitable viscosity to print and extrude the gel, the cold incubation is necessary. At room temperature, there was only drops formation rather than fiber deposition. FIGS. 13B and 13C shows storage modulus (G') and loss modulus (G") and their temperature dependency for different concentrations of non-crosslinked 5% and 7% (w/v) GelMA hydrogel solutions in oscillatory mode from 4 to 37° C., at constant frequency, shear rate and strain of 1 Hz, 3 s$^{-1}$, and 1%, respectively. Comparing storage modulus (G') between 5% and 7% (w/v) non-crosslinked GelMA showed that when the polymer concentration is higher, stiffer constructs are achieved that corresponds to a higher crosslinking density. Moreover, the gel point of two concentrations happens in less than 37° C., and at this point, the almost zero G' is due to the cleavage of hydrogen bonds in the range from 30 at 37° C. Upon cooling, G' of the hydrogels attempted to recover and increase rapidly but, they just crossed over the G" indicating the typical behavior of a gel-like structure. Furthermore, viscosity does increase with increasing GelMA concentrations. In confirmation with Rizwan et al., the viscosity of uncrosslinked GelMA hydrogels can be increased by increasing GelMA concentration or by decreasing temperature. (39) To obtain a viscosity required for printing, increasing the concentration of GelMA hydrogels beyond 7% (w/v) can potentially limit cellular proliferation within the scaffolds. Therefore, to obtain printable hydrogels without affecting cell viability, GelMA hydrogels were kept at 4° C. prior to printing.

Example 4

Figure 14A:
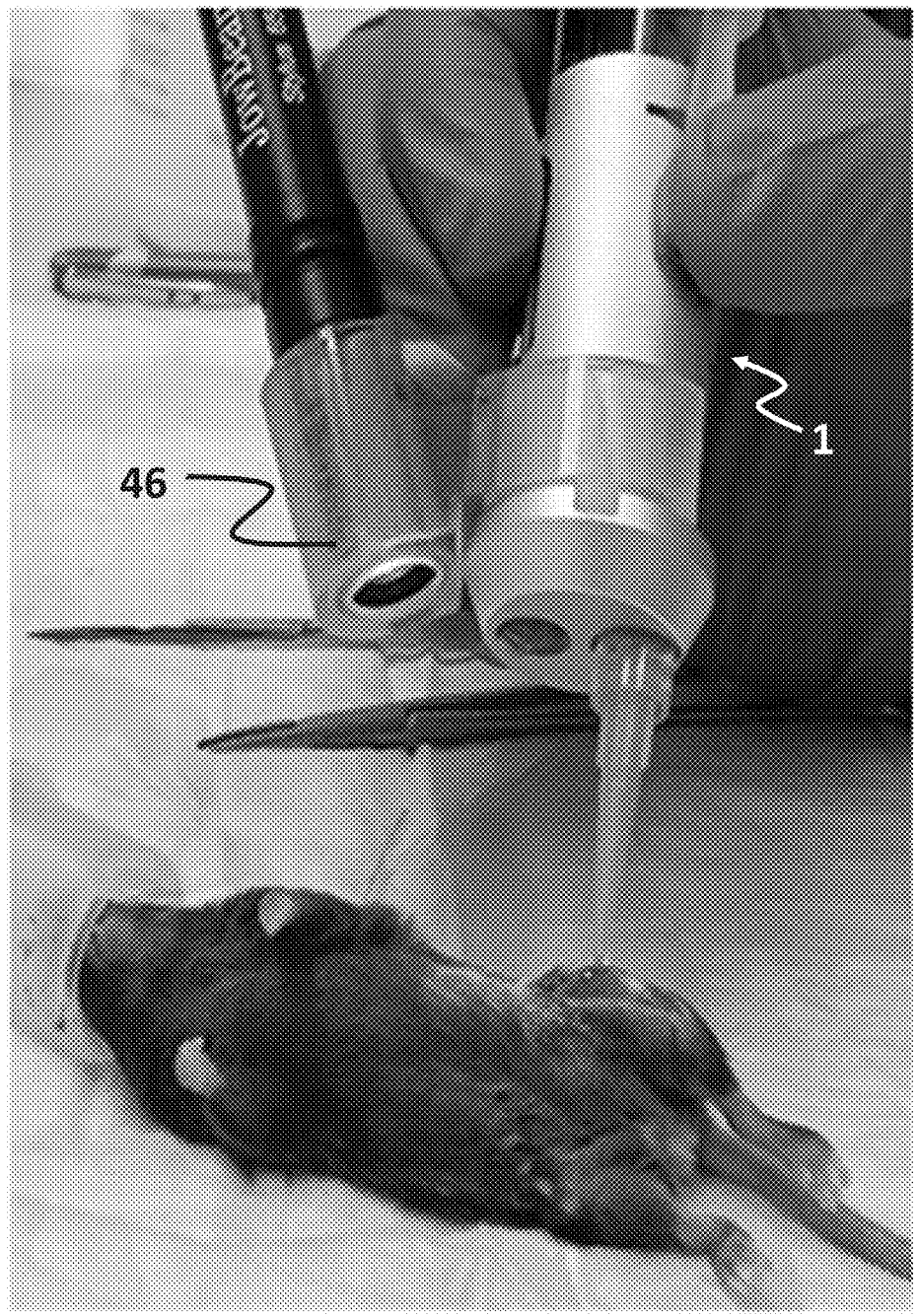
FIGS. 14A-14J illustrate in vivo application and histological assessment of in situ printing in VML injuries in the murine model after 4 weeks of implantation according to embodiments of the disclosure.
Figure 14B:
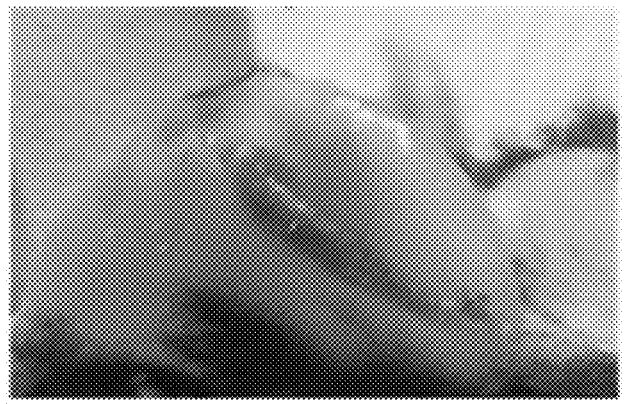
Figure 14C:
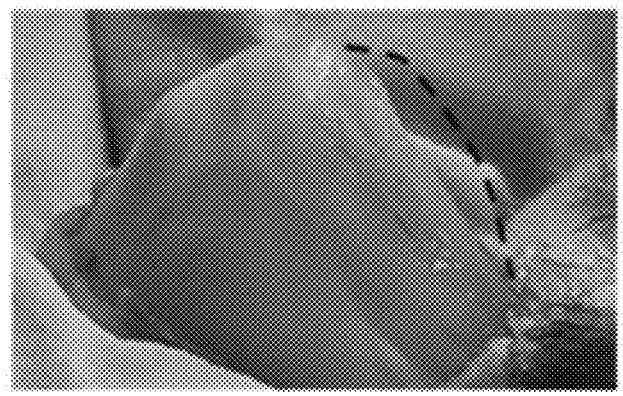
Figure 14D:
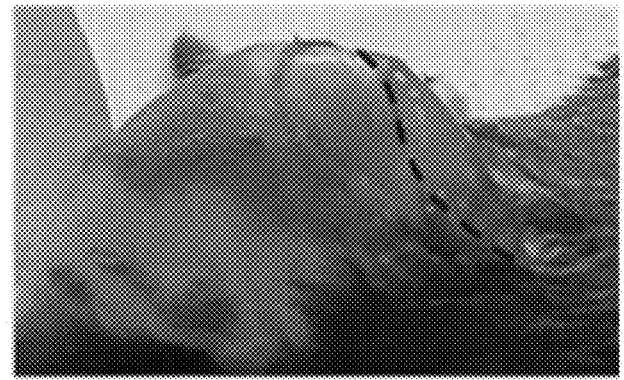

The feasibility of the in situ printing of GelMA scaffolds within the VML defects was evaluated in a murine model with a VML muscle injury. FIGS. 14A-14J depict in vivo application and histological assessment of in situ printing in VML injuries in the murine model after 4 weeks of implantation. Animals underwent unilateral volumetric loss of the quadriceps muscle to form a VML injury. Acellular GelMA hydrogels were loaded in syringes and was cooled down to about 4° C. The syringe was placed in the handheld partially automated bioprinter and then used for printing a scaffold directly within the injury site (FIG. 14A). Based on the mechanical data and the degradation profiles, GelMA at 7% (w/v) was used for the animal studies. The intact and shaved muscles are shown in FIGS. 14B-14D, and the ease-of-reconstructing the overall structure of the damaged skeletal muscle is demonstrated. FIGS. 14A-14D depict surgical implantation of GelMA hydrogels via in situ printing into murine VML injury. FIGS. 14B, 14C and 14D illustrate the murine muscle situs before VML surgery, post VML surgery, and post in situ printing of GelMA hydrogel. The main purpose of the in vivo study was to assess the feasibility of the printing process within a VML murine model. Acellular GelMA hydrogels were used to assess the tissue adhesion and inflammation at the defect site as fibrosis post-injury is one of the factors preventing any tissue regeneration. In addition, it is widely accepted that the satellite cells within the native muscle if properly stimulated without the presence of significantly inflammatory markers can fuse into existing muscle bundles and thicken them to increase their strength. Our data suggest that the in situ printed scaffolds contributed to this process and hypertrophy is achieved.

Figure 14E:
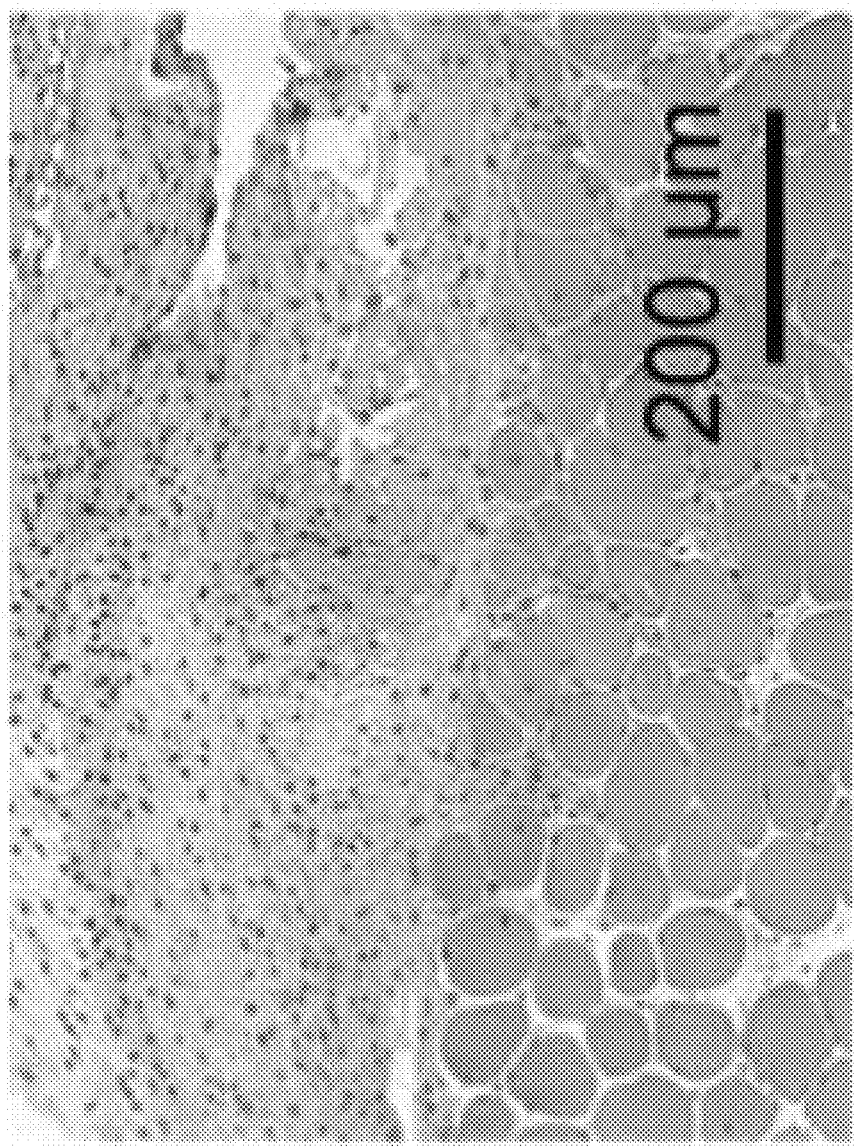

On day 28 post-surgery, the animals were euthanized, and the injured tissue was harvested. The hematoxylin and eosin (H & E) staining of the harvested samples showed their proper adhesion to the surrounding tissues and no signs of rupture in the scaffolds, confirming the suitable mechanical properties of in situ printed scaffolds (FIG. 14E). There is also evidence of integration, as well as cellular infiltration at the interface of scaffolds and muscle tissue (FIG. 14E). FIG. 14E shows H&E staining of the interface of skeletal muscle tissue and an in situ printed scaffold harvested 4 weeks post-surgery. The image of FIG. 14E shows evidence of integration of the scaffold at the 4 week time point with cellular proliferation and migration into the GelMA scaffold. In addition, no signs of severe inflammatory response such as edema and hyperthermia against the in situ printed scaffolds were observed.

Figure 14F:
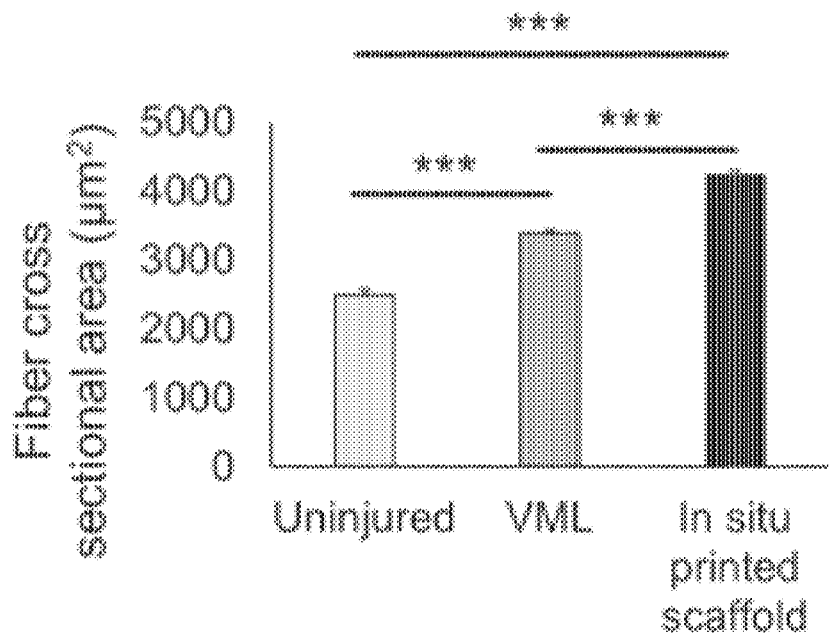
Figure 14G:
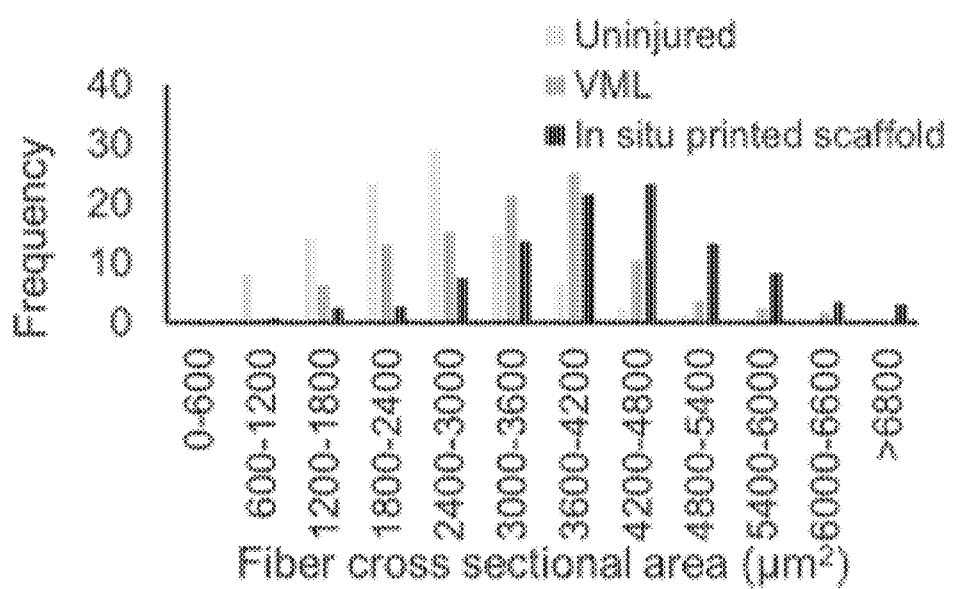
Figures 14H, 14I, 14J:
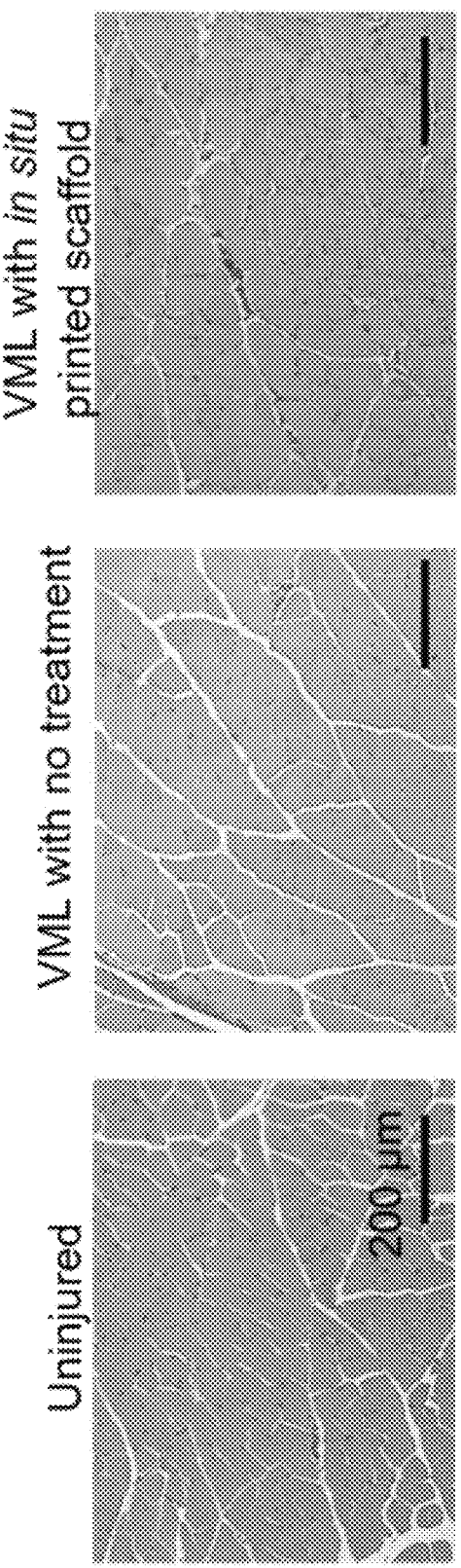

Biocompatibility of GelMA has been previously reported in the literature. (44) The fiber size in the native muscle tissue was compared in three animal groups: healthy control (no injury), VML injury without treatment (negative control), and VML injury treated with an in situ printed GelMA scaffold (FIGS. 14F-14J). As shown in FIG. 14F, average fiber central surface area ($\mu m^2$) in quadriceps muscle of uninjured mice and mice having undergone VML injury and were either untreated or treated with an in situ printed scaffold. In the VML injury group treated with in situ printed scaffolds, muscle fiber surface area was larger than VML without in situ printed scaffold muscle ($p<0.001$) and uninjured muscle ($p<0.001$). FIG. 14G shows fiber cross-sectional area ($\mu m^2$) distribution in quadriceps muscle of uninjured mice and mice having undergone VML injury and were either untreated or treated with an in situ printed scaffold. FIGS. 14H, 14I and 14J show H&E staining of the harvested quadriceps muscle of the uninjured, VML without treated, and VML treated with in situ printed scaffold, respectively. As muscle strength and function, in general, correlates with fiber size, we evaluated changes in muscle fiber hypertrophy following treatment. (45) The analysis of average fiber central surface area four weeks post-surgery showed a statistically significant difference in fiber size between the three groups (FIGS. 14F and 14G). As expected, remnant muscle fibers underwent hypertrophy following VML injury as a mechanism to compensate for muscle loss. The muscle tissue in the VML injury group receiving in situ printed scaffolds muscle tissue was on average 25% larger ($4231\pm69$ $\mu m^2$) than VML without treatment ($3394\pm46$ $\mu m^2$). The smallest fiber cross-sectional area was noted in the uninjured mice ($2497\pm79$ $\mu m^2$), as no injury occurred in this group to stimulate hypertrophy. FIG. 14G illustrates the fiber size distribution in non-regenerating fibers in the uninjured, VML injury, and VML injury with in situ printed scaffolds. The muscle mass resected was similar in both groups control VML groups and VML groups receiving GelMA scaffold. It is important to note that typically, hypertrophy post injury has been augmented by the delivery of growth factors and physical exercise. (46-48) The results from this Example 4 suggest that a suitable scaffold can also contribute to muscle hypertrophy.

Example 5

Figure 15:
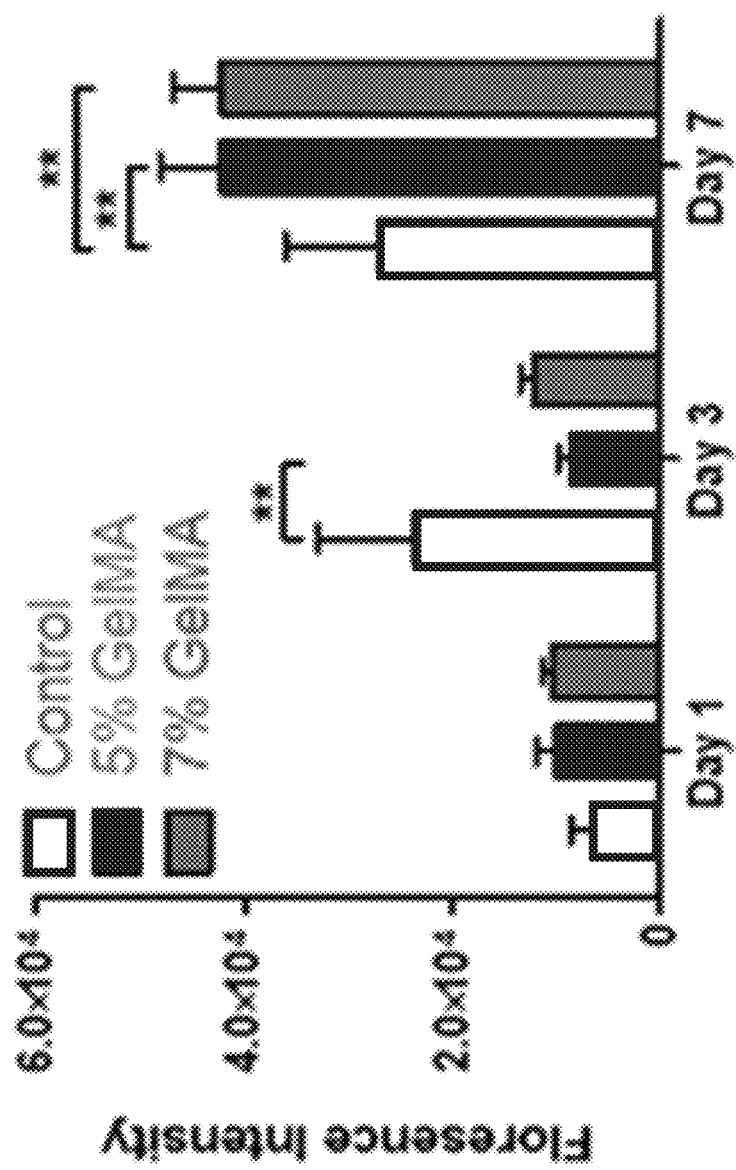
FIG. 15 is a plot of florescence intensity versus day of cell culture illustrating cell viability of 20 microLiter (μL), 500 micron (μm) sheets of 5% and 7% (w/v) GelMA over 7 days of culture.
Figure 16A:
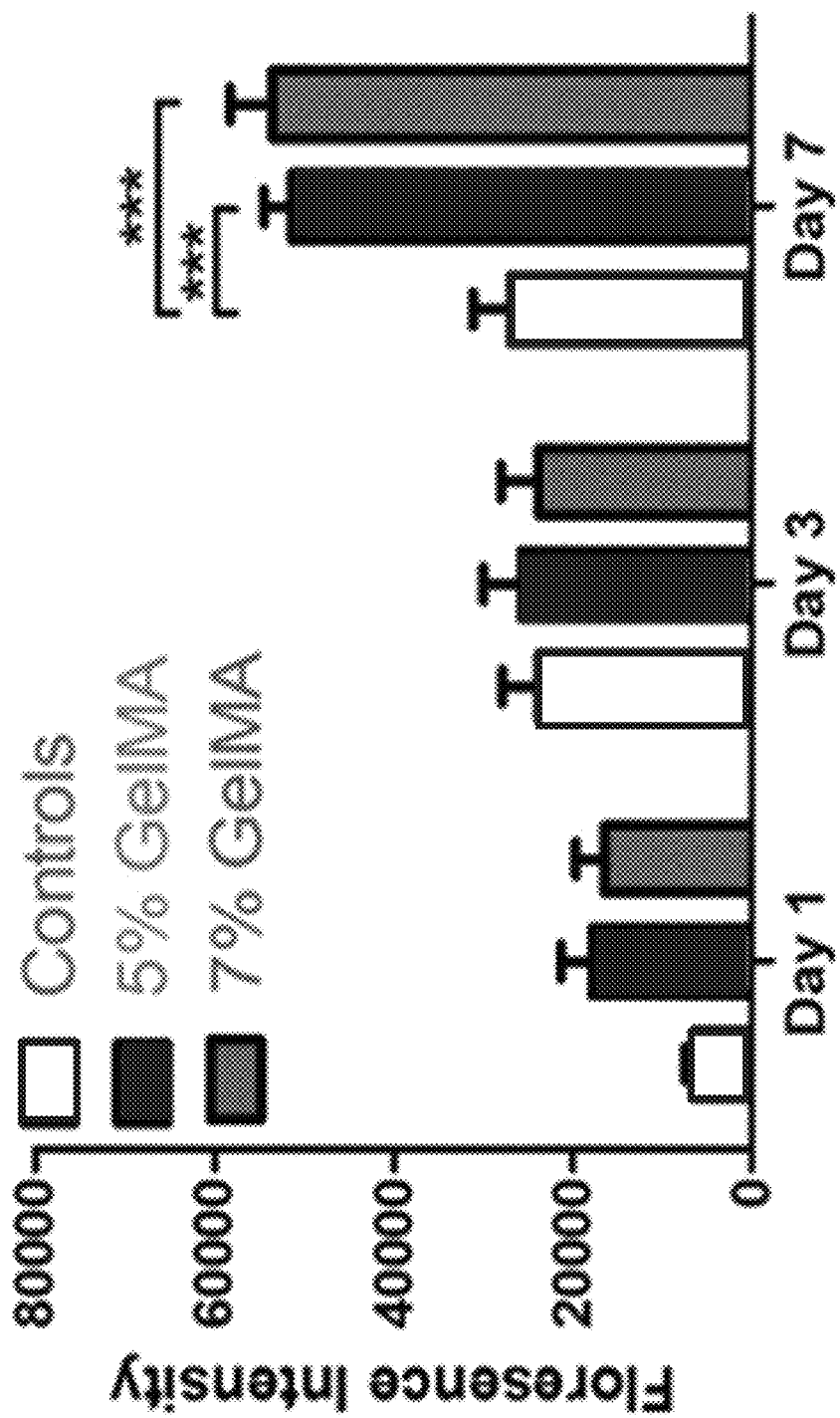
FIG. 16A illustrates results of a viability assay for evaluation of the cell proliferation rate in both 5% and 7% (w/v) GelMA hydrogel formulations over 7 days of culture.
Figure 16B:
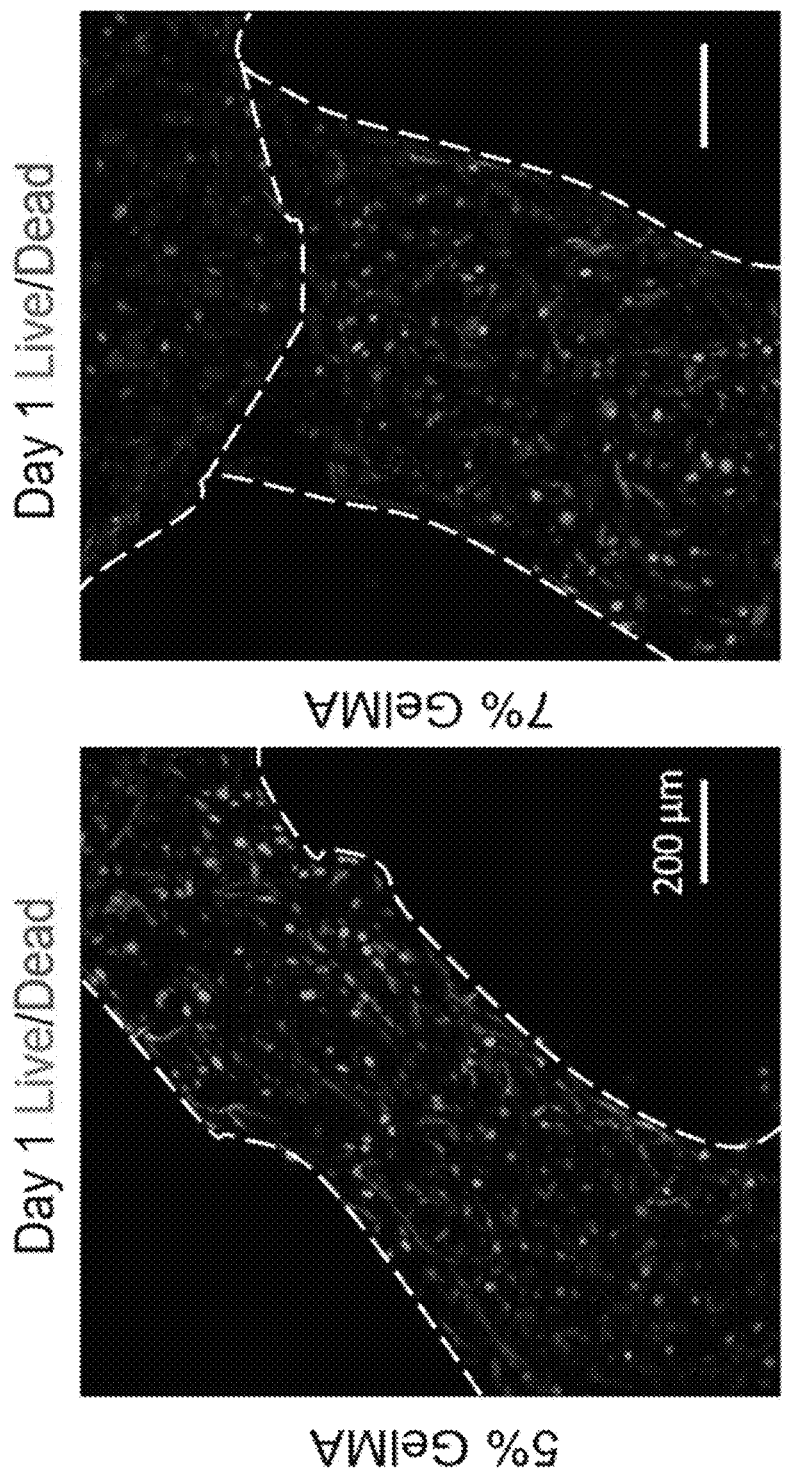
FIGS. 16B and 16C illustrate results of viability assay of cells evaluated within the in situ bioprinted scaffolds using a live/dead assay 1 day and 3 days, respectively, after printing according to embodiments of the disclosure.
Figure 16C:
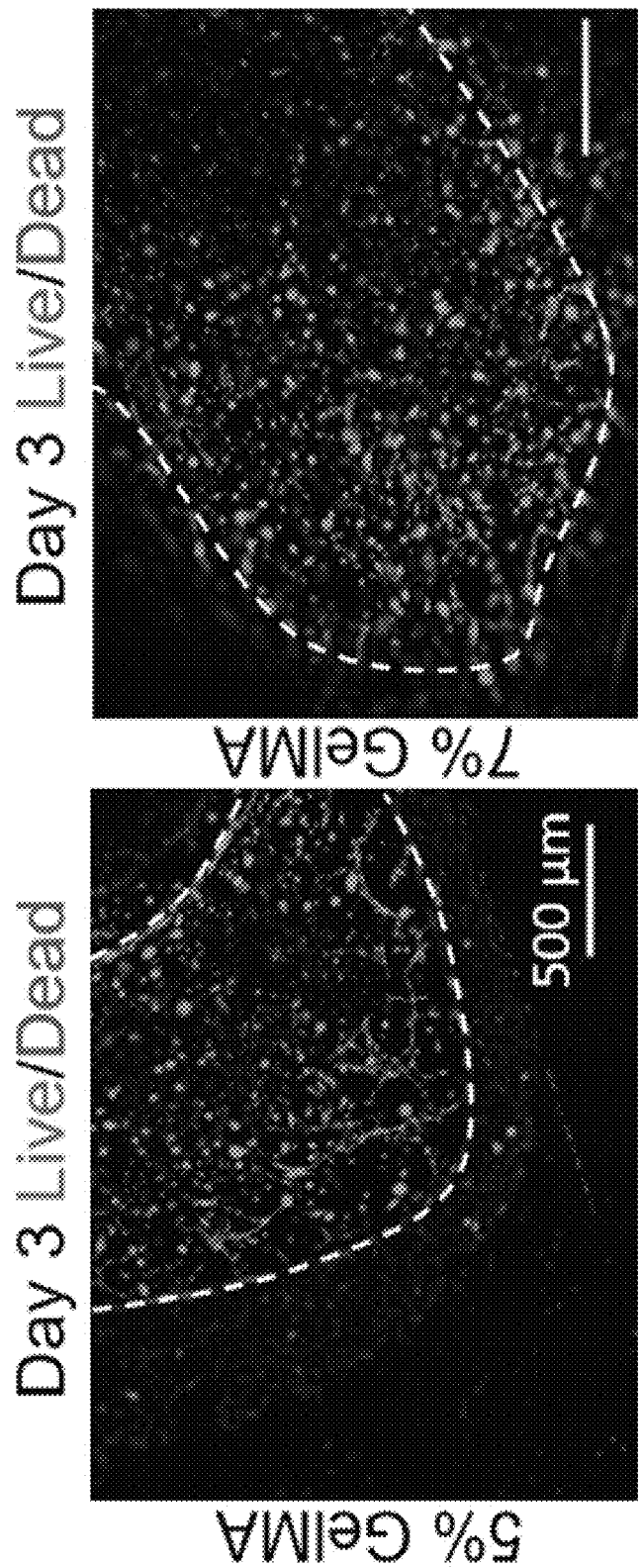
Figure 16D:
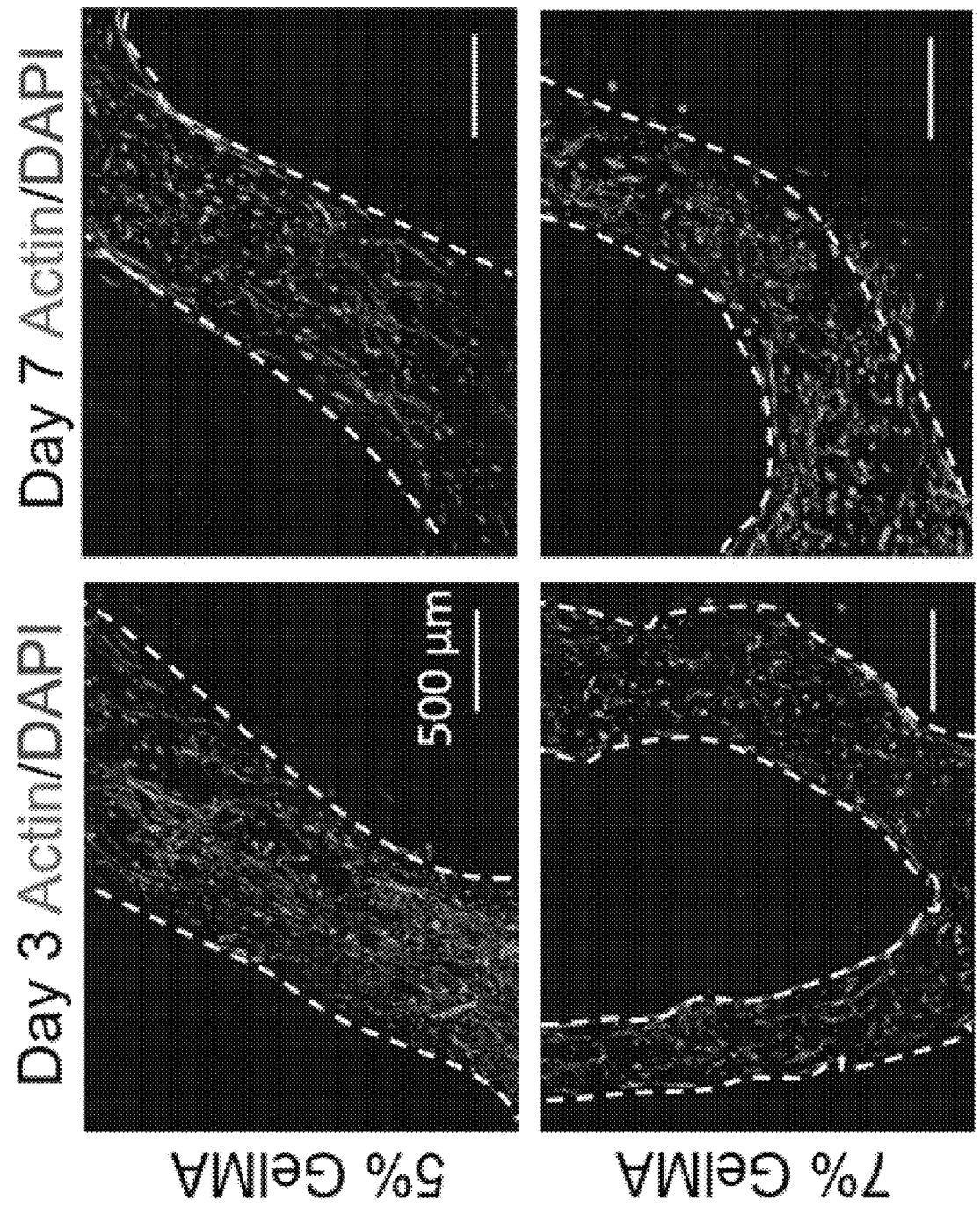
FIG. 16D illustrates F-actin and nuclei staining of cells encapsulated in 5% and 7% GelMA hydrogels, demonstrating the morphology and distribution of cells, according to embodiments of the disclosure.

In addition to extrusion of scaffolding materials and hydrogel inks, the developed handheld partially automated bioprinter can potentially be utilized for the transplantation of cells directly to the wound site. The suitability of the GelMA hydrogel was assessed for cell encapsulation and delivery of C2C12 myoblasts using the handheld partially automated bioprinter. For this reason, cells were mixed with the GelMA bioinks at a concentration of $3\times10^6$ cell/mL. To assess the interaction and printability of cells encapsulated in bioinks, 500 μm thick flat hydrogel sheets were deposited, and the metabolic activity of the cells was measured using PrestoBlue™ assay over 7 days of culture (FIG. 15, cell viability of 20 μL, 500 μm sheets of 5% and 7% (w/v) GelMA). The results confirmed that the material did not negatively affect the metabolic activity of the encapsulated cells in comparison to the tissue culture plate (TCP). To assess the potential effects of the handheld partially automated bioprinter on the encapsulated cells, scaffolds (25 μL, 1 cm long 3×3 fiber array) were bioprinted on TMSPMA-coated glass slides to ensure their proper adhesion over the course of the experiments. The metabolic activity of cells encapsulated within the in situ bioprinted scaffolds was measured over 7 days of culture. The results suggested that the metabolic activity of cells encapsulated within the scaffolds increased faster than those cultured in TCP (FIG. 16A, PrestoBlue viability assay for evaluation of the cell proliferation rate in both 5% and 7% (w/v) GelMA hydrogel formulations over 7 days of culture). This might be due to the higher surface area of the scaffolds in comparison to TCP. Moreover, it can be concluded that the bioprinting process, printing pressure, and applied shear forces did not induce significant cell death. To confirm the results of the PrestoBlue™, the viability of the cells was evaluated within the in situ bioprinted scaffolds using a Live/Dead assay 1 day (FIG. 16B) and 3 days (FIG. 16C) after printing. The dashed lines indicate borders of printed scaffolds. The majority of cells (>80%) appeared green (live) with only a few cells stained red (dead). The results are in agreement with the metabolic activity data. The morphology of encapsulated myoblasts cells in GelMA hydrogels was assessed by staining the F-actin in the cytoskeleton of cells on days 3 and 7 after printing (FIG. 16D). FIG. 16D shows F-actin (Alexa Fluor™ 488 Phalloidin, green) and nuclei (DAPI, blue) staining of cells encapsulated in 5% and 7% GelMA hydrogels, demonstrating the morphology and distribution of cells. Fluorescent images showed that the cells spread and proliferated in the entire hydrogel and the assembly of F-actin cytoskeleton of cells was not affected by the printing process.

Figure 16E:
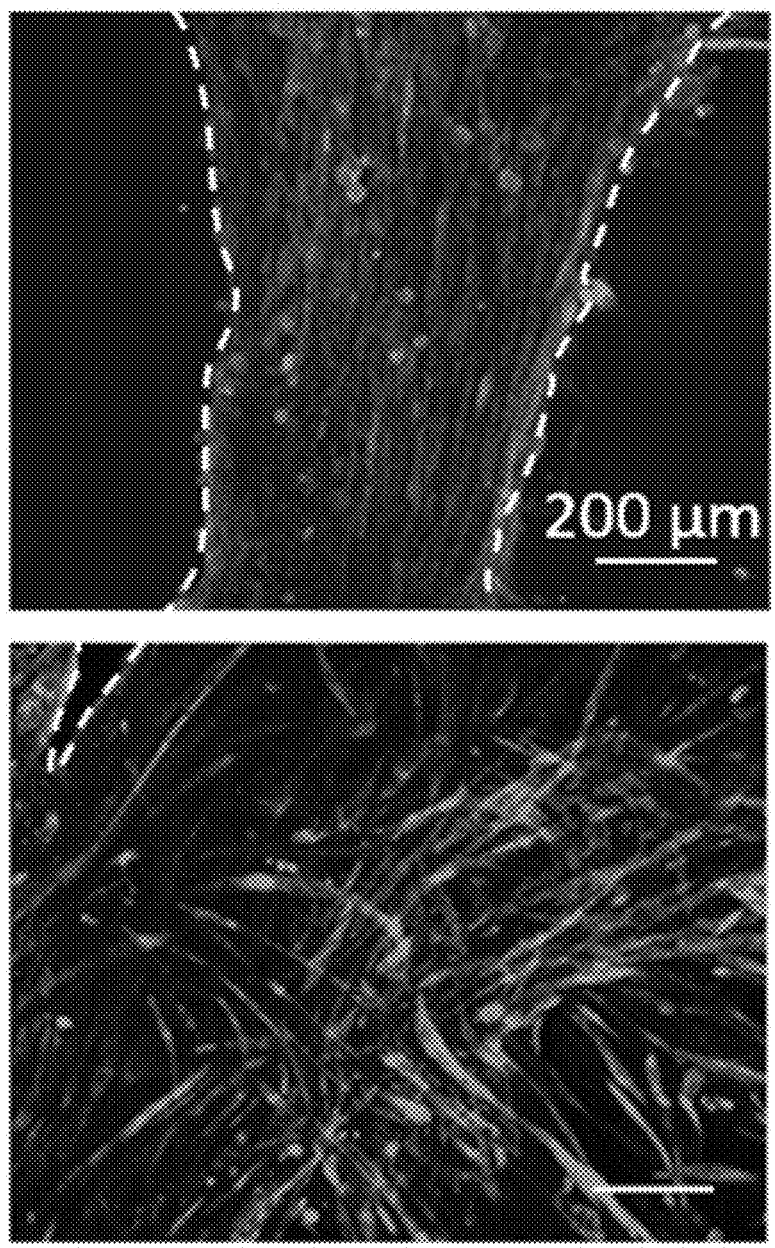
FIG. 16E illustrates MHC and DAPI immunostaining of cells on day 24 post culture in differentiation culture medium according to an embodiment of the disclosure.

The ultimate goal of delivering muscle cells to the site of injuries is to facilitate the formation of myofibers and multinucleated myotubes. The in situ bioprinted scaffolds were transferred to differentiation culture medium after 7 days of culture in growth medium. The formation of myotubes was assessed by staining against myosin heavy chains (MHCs) and nuclei (DAPI) on day 24 after differentiation. The results confirmed the formation of multinucleated millimeter long myotubes (FIG. 16E). FIG. 16E shows MHC (green) and DAPI (blue) immunostaining of cells on day 24 post culture in differentiation culture medium. FIG. 16F shows SEM images of 5% and 7% (w/v) lyophilized GelMA hydrogels with encapsulated cells post differentiation 14 days of culture (yellow arrows). The SEM images showed the formation of myotubes (shown with yellow arrows) within the 3D hydrogel network. These data show that if fine nozzles are being implemented, highly organized myotubes will be achieved. However, in skeletal muscles, the mechanical stimulation during the body movement and the interaction of neotissue with surrounding tissue is a major factor that directs the organization of cells within the new tissue.

In the foregoing Examples, the following materials and methods were employed.

All materials were purchased from Sigma-Aldrich unless mentioned otherwise and were used without any modification with the exception of GelMA, which was synthesized, following previously reported protocols. (38) Type A gelatin from porcine skin (Sigma-Aldrich) was added at 10% (w/v) in DPBS (VWR) and mixed at 50° C. until dissolved.

Methacrylic anhydride ("MA", Sigma-Aldrich) was slowly added dropwise to the solution at a 1.25% (v/v) and stirred at 50° C. and allowed to react for 1 hr. The reaction was terminated by adding a 5× dilution of DPBS. The solution was dialyzed against distilled water to remove excess salt and unreacted methacrylic anhydride using dialysis tubes with a 12-14 kDa cutoff (Fisherbrand®). Distilled water was changed every 12 hr for one week. The solution was filtered, frozen, and lyophilized for one week and stored at −20 to 4° C. for later use. Myoblast cells and cell culture media and biological reagents were purchased from Sigma-Aldrich.

Hydrogel Ink Preparation

Lyophilized GelMA was dissolved at 5% and 7% (w/v) in DPBS (Sigma-Aldrich) at 37° C. containing 0.067% (w/v) of lithium phenyl-2, 4, 6-trimethylbenzoylphosphinate (LAP) obtained from Allevi Inc. The hydrogel ink was then loaded into 2 mL plastic syringes for further experiments.

Rheological Testing

A rheometer (Anton Paar MCR 702 TwinDrive, Austria), equipped with a plate-plate geometry with the size of 22 mm was used to measure the rheological properties of non-crosslinked 5% and 7% (w/v) GelMA hydrogels solution in oscillatory mode. To evaluate the effect of temperature on complex viscosity of solutions, storage moduli (G') and loss moduli (G") temperature sweep rheometry was performed from 4 to 37° C., at a constant frequency, shear rate and strain of 1 Hz, 3 s$^{-1}$, and 1%, respectively. The measurement gap size between the sample and the plate was set to 0.6 mm. Water was added to the bottom plate geometry during the measurement to prevent sample dehydration. All of the measurements were repeated three times.

In Vitro Degradation of GelMA

The degradation of the crosslinked hydrogels was assessed in two conditions: 1) DPBS at biological pH, and 2) DPBS containing collagenase (1.75 µg/mL) to mimic enzymatic degradation of gelatin-based materials in vivo. Hydrogel disks of 10 mm in diameter and 4.5 mm in thickness with a total volume of about 400 µL were fabricated and crosslinked with UV light at 365 nm for 20 sec. To facilitate the handling of the samples, the hydrogel disks were fabricated on the surface of cut TMSPMA-coated 1 cm by 1 cm glass slides. The samples were then weighed and placed in well plates containing 2.2 mL of one of the solutions mentioned above. A total of 12 samples were used for each condition. Samples were incubated at 37° C. for 14 consecutive days. The samples were removed from the collagenase and DPBS solutions, blotted with Kimwipes™ to remove excess solution and weighed. The constructs in collagenase solution were measured at time points 1, 3, 6, 12, 24, 36, 48 hours, and every day after until the construct had been completely digested. The constructs in plain DPBS were measured every 24 hours from the initial emersion. The weight loss percentage was determined with the following equation:

$$\text{Weight Loss (\%)} = ((W_0 - W_1)/W_0) \times 100,$$

where $W_0$ is the initial dry weight and $W_1$ is the weight at the measured time points.

Assessment of the Adhesion Strength of GelMA-Based Hydrogels to Skeletal Muscle Tissues The adhesion strength of GelMA-based hydrogels to skeletal muscle tissue was assessed against tensile and shear loads. The measurements were carried out using an Electroforce 3220 (TA Instruments) mechanical tester at a displacement rate of 0.166 m/s. The zero position was adjusted to the size of the samples for each of the respective tests.

The ultimate tensile adhesion strength of GelMA hydrogels was determined according to a modified version of the standard test method ASTM F2458-05. (42) Both of the hydrogels at different concentrations were prepared as previously described. Rectangular samples (10 mm×10 mm×1 mm) of freshly harvested porcine skeletal muscle were cut and glued to a face of the adhesion clamps. The other clamp was covered either by similar skeletal muscle tissue or a piece of TMSPMA-coated glass slide. GelMA bioink with a similar width, length, and thickness in respect to the geometry of porcine skeletal muscle samples was printed between two pieces of porcine skeletal muscle and were then photocrosslinked. Using the Electroforce 3220 machine, the samples were stretched, and the stress and strain were calculated for both groups until the point of rupture and full separation; each group contained a sample size of n=10.

The ultimate adhesion strength of GelMA hydrogels against shear forces was examined following a modified version of ASTM F2255-05 standard. (43) GelMA prepolymers were prepared as previously described. Two different conditions were tested: 1) GelMA sandwiched between two pieces of porcine skeletal muscle tissues and 2) GelMA sandwiched between a TMSPMA-coated glass slide from one side and porcine skeletal muscle from the other side. TMSPMA-coated glass slides were cut to dimensions of 10 mm×35 mm. GelMA samples were printed (10 mm×5 mm×2 mm) between two glass slides and fully crosslinked using the integrated UV light. To assess the adhesion to the skeletal muscle, freshly harvested porcine muscle tissue was sliced using a meat slicer and glued to the glass slides before the printing of the GelMA hydrogels. Using an Electroforce 3220, each testing condition had a sample size of n=12, and samples were tested until the sample rupture or detachment.

The compressive modulus and strength of GelMA-based scaffolds were also determined. Cylindrical GelMA prepolymer hydrogels were prepared as previously described. The cylinders were 10 mm in diameter with a 4.5 mm height, the samples crosslinked for 20 s. Immediately after being exposed to UV light, the samples were tested using an Electroforce 3220. The compression test was conducted at a sampling rate of 0.166 m/s for both 5% and 7% (w/v) GelMA hydrogels; each group had a sample size of n=6. The compressive modulus was determined from the slope of the linear region of the stress-strain curve correlating to 0-10% strain.

Scanning Electron Microscopy (SEM)

The interconnected porous structure of crosslinked GelMA hydrogels was analyzed using an environmental SEM (FEI Quanta 200 Environmental). However, to improve the quality of the images, the samples were freeze-dried prior to imaging. Crosslinked GelMA samples were immersed and frozen in liquid nitrogen and lyophilized for 2 days. The lyophilized samples were broken to reveal their cross-sections and were sputtered with gold using a sputter coater (Cressington 106 Auto Sputter Coater). Images were captured using SEM with accelerating voltages of 3-10 kV. Cell encapsulated GelMA hydrogels were also analyzed via SEM. Myotubes after 24 days post-differentiation were fixed at room temperature in 4% (w/v) paraformaldehyde for 10 minutes and then washed with DPBS. The encapsulated cell samples were then frozen in liquid nitrogen, lyophilized, sputtered, and imaged in the same manner described above.

Cell Culture and Biological Assays

Immortalized mouse myoblasts (C2C12) (Sigma-Aldrich) were expanded by culturing in Dulbecco's Modified Eagle Medium (DMEM) supplemented with 10% (v/v) fetal bovine serum (FBS) and 1% (v/v) penicillin-streptomycin (Pen-Strep). Cells were passaged every 3 days or at 80% confluency. For the experiments, cells with a passage number of less than 6 were harvested by treatment with trypsin-EDTA (0.1%). Nine million cells were resuspended in 150 µL of growth medium and added to each 3 mL pre-prepared GelMA/LAP solution to achieve a cellular density of 3×10⁶ cell/mL. The cell-laden prepolymers were loaded into 2 mL syringes and kept at 4° C. for 10 min to induce a pre-gelation as GelMA is a temperature sensitive gel (rheology data). Cell encapsulated bioinks were printed on TMSPMA-coated glass slides (1=1 cm), photocrosslinked and placed in 24-well plates. Cell growth media was gently added to the samples and was refreshed every 2 days. During the growth phase (until day 7), the growth culture medium was used. Differentiation medium containing DMEM supplemented with 2% (v/v) horse serum and 1% (v/v) Pen-Strep was used after 7 days of culture to facilitate myotube formation. Samples were kept in culture for an additional 24 days.

Cellular viability was assessed using Live/Dead™ Viability/Cytotoxicity Kit (Invitrogen) on day 3, according to the manufacturer's instructions. In brief, samples were washed with DPBS and incubated with a DPBS solution containing 0.5 µL/mL calcein-AM and 2 µl/mL ethidium homodimer for 15 min at 37° C. The samples were imaged using an inverted Zeiss fluorescent microscope in which live, and dead cells appear in green and red colors, respectively.

Cellular (C2C12s) metabolic activities and proliferation in hydrogels were evaluated by PrestoBlue Cell Viability Assay (Invitrogen) on days 1, 3, and 7. The printed structures were incubated for 1 hr at 37° C. with a solution of culture media supplemented with 10% (v/v) of the assay reagent. Then, the fluorescent intensity of the solution was measured at 540 nm excitation and 600 nm emission using a BioTek spectrophotometer. The analysis was conducted on printed samples as well as a thin layer of cell-laden hydrogels.

The morphology of the cells was assessed by staining F-actin and cellular nuclei using Alexa Fluor™ 488 Phalloidin and DAPI to visualize the cytoskeleton and nuclei of cells, respectively. A standard staining protocol was followed in which cells were fixed using 4% (w/v) paraformaldehyde for 10 min, then permeabilized using 0.3% (v/v) Triton for 15 min, and blocked with BSA for 30 min at room temperature. The blocked samples were serially incubated with phalloidin and DAPI solution for 45 min, respectively. The samples were washed and imaged using the same inverted Zeiss fluorescent microscope.

Formation of myotubes was assessed by immunostaining anti-fast myosin skeletal heavy chain antibody (Abcam ab51263 antibody). Encapsulated cells in samples were fixed by 4% (w/v) paraformaldehyde for 10 min, then permeabilized by 0.3% (v/v) Triton for 10 min. Samples were in block solution of 1% BSA, 22.5 mg/mL glycine, and 0.1% Tween for 1 hr. Then 1/200 dilution of the first antibody in 0.1% BSA solution was incubated overnight in 4° C. and with 1/500 dilution of the secondary antibody, goat anti-mouse IgG H&L (Alexa Fluor® 488) (Abcam ab150117), and DAPI for 1 hour at 37° C.

Animal Study

Animal experiments were approved by the Institutional Animal Care and Use Committee (IACUC) and carried out in accordance with Protocol 2016N000375 at Brigham and Women's Hospital. Fourteen 11-week C57/Bl6 mice (The Jackson Laboratory, Bar Harbor, ME) were anesthetized in an induction chamber (2-4% isoflurane vaporizer). The hind limbs were prepared for surgery by removing the hair using a depilatory agent (Nair™ Hair Removal Lotion, Church & Dwight) and disinfected using Benzoin Compound Tincture USP (Humco Holding Group). A longitudinal incision was made through the skin of the limbs to expose the quadriceps, and the animals were divided into three groups. In the VML (n=5) and VML+in situ printed Scaffold (n=4) groups, an average of 79±7.5 mg and 78.5±8.2 mg of skeletal muscle was resected, respectively, preserving only a base of muscle as previously described elsewhere. (49) The remaining skin was then sutured to cover the injury site sutured using a 3-0 REDISILK® Black Braided Silk (MYCO Medical Supplies, Inc).

Histological Analysis

Four weeks post-surgery, the hind limb quadriceps muscles were harvested and the tissue prepared for histological analysis by fixing in 10% neutral buffered formalin for up to 40 hours and storing in 70% ethanol. The tissue was then embedded in paraffin, cut into sections and stained with hematoxylin and eosin (H&E) according to a standard protocol.

Calculation of Muscle Fiber Cross-Sectional Area

Fiber cross-sectional area (CSA) was measured for 14 mice (Uninjured=5, VML=5, VML+in situ printed scaffolds=4) using light-microscopy photographs of the H&E slides. Ten photos per sample were taken from three sections, and the photographs imported into ImageJ® software (Version 1.52a; Media Cybernetics, Bethesda, MA, USA). The CSA was measured by randomly selecting regenerating fibers with a non-centralized nucleus and measuring their surface area. Counts were performed under double-blinded conditions.

Statistical Analysis

Statistical analysis was conducted using GraphPad Prism 5.0 software. Values are reported as mean±standard deviation. Column analysis was performed using t-test with a minimum confidence level of 95%. The grouped analysis was performed using ANOVA with Tukey's multiple comparison posttest. The p values for all tests were less than or equal to 0.05 to be considered statistically significant. Data for the CSA measurement are expressed as mean±standard error, and the results were analyzed using the Student t-test. Values of $p<0.05$ were considered statistically significant.

This disclosure describes use of a portable bioprinter capable of in situ printing of scaffolds for the treatment of skeletal muscle injuries. The disclosed bioprinter is compatible with various types of bioinks, including photocrosslinkable hydrogels or polymeric solutions conventionally used in tissue engineering and bioprinting. Extremely viscous solutions can however affect the reliability of the device. The feasibility of in situ printing of GelMA hydrogel for the treatment of muscle injuries was tested. The bioprinter enabled printing on non-flat surfaces, which cannot be achieved using regular stationary bioprinters. In addition, the in situ printed scaffolds adhered to the surrounding tissues and the adhesion strength could be tailored by adjusting the GelMA concentration. The feasibility of using the partially automated bioprinter for in situ printing of scaffolds in muscle injury was tested in a murine VML model. Histological analysis confirmed the proper adhesion and integration of the printed scaffolds and surrounded tissues, while no signs of tearing or rupture within the scaffolds were observed. The in situ printed scaffolds supported cellular ingrowth over 28 days of implantation, and no signs of severe inflammation were observed. Importantly, the scaffold supported myogenesis and improved skeletal muscle hypertrophy following injury. The possibility of bioprinting encapsulated cells in GelMA hydrogels, and simultaneous photocrosslinking was tested. The printing pressure and applied shear stress using the handheld bioprinter did no adverse impact on the viability and proliferation of myoblasts. The encapsulated cells formed multinucleated myotubes after 24 days of differentiation as confirmed by staining for MHC.

The disclosed bioprinter represents a paradigm shift in trauma care and overcomes various challenges in the treatment of traumatic injuries. The in situ printed scaffolds can be used either in acellular or cellular forms. The bioprinter's ease-of-utilization reduces the response time for the treatment of traumatic injuries, which in turn lowers the risk of fibrosis and improves tissue regeneration and functional recovery.

Various embodiments disclosed herein are to be taken in the illustrative and explanatory sense, and should in no way be construed as limiting of the present disclosure.

While aspects of the present disclosure have been particularly shown and described with reference to the embodiments above, it will be understood by those skilled in the art that various additional embodiments may be contemplated by the modification of the disclosed machines, systems and methods without departing from the spirit and scope of what is disclosed. Such embodiments should be understood to fall within the scope of the present disclosure as determined based upon the claims and any equivalents thereof.

REFERENCES (1) Nuutila, K.; Sakthivel, D.; Kruse, C.; Tran, P.; Giatsidis, G.; Sinha, I. Gene expression profiling of skeletal muscle after volumetric muscle loss. Wound Repair and Regeneration 2017, 25 (3), 408-413, DOI: 10.1111/wrr.12547.

(2) Garg, K.; Ward, C. L.; Rathbone, C. R.; Corona, B. T. Transplantation of Devitalized Muscle Scaffolds is Insufficient for Appreciable de Novo Muscle Fiber Regeneration after Volumetric Muscle Loss Injury. Cell and Tissue Research 2014, 358 (3), 857-873, DOI: 10.1007/s00441-014-2006-6.

(3) Pollot, B. E.; Corona, B. T. Volumetric Muscle Loss. In Skeletal Muscle Regeneration in the Mouse: Methods and Protocols; Kyba, M., Ed.; Springer New York: New York, NY, 2016; pp 19-31.

(4) Grogan, B. F.; Hsu, J. R.; Consortium, S. T. R. Volumetric Muscle Loss. 2011, 19, S35-S37.

(5) Fan, C.; Jiang, P.; Fu, L.; Cai, P.; Sun, L.; Zeng, B. Functional Reconstruction of Traumatic Loss of Flexors in Forearm with Gastrocnemius Myocutaneous Flap Transfer. Microsurgery 2008, 28 (1), 71-75, DOI: 10.1002/micr.20449.

(6) Li, M. T. A.; Willett, N. J.; Uhrig, B. A.; Guldberg, R. E.; Warren, G. L. Functional analysis of limb recovery following autograft treatment of volumetric muscle loss in the quadriceps femoris. Journal of Biomechanics 2014, 47 (9), 2013-2021, DOI: https://doi.org/10.1016/j.jbiomech.2013.10.057.

(7) Chal, J.; Oginuma, M.; Al Tanoury, Z.; Gobert, B.; Sumara, O.; Hick, A.; Bousson, F.; Zidouni, Y.; Mursch, C.; Moncuquet, P.; Tassy, O.; Vincent, S.; Miyanari, A.; Bera, A.; Garnier, J.-M.; Guevara, G.; Hestin, M.; Kennedy, L.; Hayashi, S.; Drayton, B.; Cherrier, T.; Gayraud-Morel, B.; Gussoni, E.; Relaix, F.; Tajbakhsh, S.; Pourquié, O. Differentiation of Pluripotent Stem Cells to Muscle Fiber to Model Duchenne Muscular Dystrophy. Nature Biotechnology 2015, 33, 962, DOI: 10.1038/nbt.3297 https://www.nature.com/articles/nbt.3297#supplementary-information.

(8) Schiaffino, S.; Reggiani, C. Fiber Types in Mammalian Skeletal Muscles. Physiological Reviews 2011, 91 (4), 1447-1531, DOI: 10.1152/physrev.00031.2010.

(9) Criswell, T. L.; Corona, B. T.; Wang, Z.; Zhou, Y.; Niu, G.; Xu, Y.; Christ, G. J.; Soker, S. The Role of Endothelial Cells in Myofiber Differentiation and the Vascularization and Innervation of Bioengineered Muscle Tissue In Vivo. Biomaterials 2013, 34 (1), 140-149, DOI: https://doi.org/10.1016/j.biomaterials.2012.09.045.

(10) Ward, C. L.; Ji, L.; Corona, B. T. An Autologous Muscle Tissue Expansion Approach for the Treatment of Volumetric Muscle Loss. BioResearch Open Access 2015, 4 (1), 198-208, DOI: 10.1089/biores.2015.0009.

(11) Chal, J.; Al Tanoury, Z.; Hestin, M.; Gobert, B.; Aivio, S.; Hick, A.; Cherrier, T.; Nesmith, A. P.; Parker, K. K.; Pourquié, O. Generation of Human muscle Fibers and Satellite-like Cells from Human Pluripotent Stem Cells In Vitro. Nature Protocols 2016, 11, 1833, DOI: 10.1038/nprot.2016.110.

(12) Fallahi, A.; Khademhosseini, A.; Tamayol, A. Textile Processes for Engineering Tissues with Biomimetic Architectures and Properties. Trends in Biotechnology 2016, 34 (9), 683-685, DOI: https://doi.org/10.1016/j.tibtech.2016.07.001.

(13) Aguilar, C. A.; Greising, S. M.; Watts, A.; Goldman, S. M.; Peragallo, C.; Zook, C.; Larouche, J.; Corona, B. T. Multiscale Analysis of a Regenerative Therapy for Treatment of Volumetric Muscle Loss Injury. Cell Death Discovery 2018, 4 (1), 33, DOI: 10.1038/s41420-018-0027-8.

(14) Atala, A.; Kasper, F. K.; Mikos, A. G. Engineering Complex Tissues. Science Translational Medicine 2012, 4 (160), 160rv12, DOI: 10.1126/scitranslmed.3004890.

(15) Lee, K.; Silva, E. A.; Mooney, D. J. Growth factor delivery-based tissue engineering: general approaches and a review of recent developments. Journal of the Royal Society, Interface 2011, 8 (55), 153-170, DOI: 10.1098/rsif.2010.0223.

(16) Faramarzi, N.; Yazdi, I. K.; Nabavinia, M.; Gemma, A.; Fanelli, A.; Caizzone, A.; Ptaszek, L. M.; Sinha, I.; Khademhosseini, A.; Ruskin, J. N.; Tamayol, A. Patient-Specific Bioinks for 3D Bioprinting of Tissue Engineering Scaffolds. Advanced Healthcare Materials 2018, 7 (11), 1701347, DOI: 10.1002/adhm.201701347.

(17) Tamayol, A.; Najafabadi, A. H.; Aliakbarian, B.; Arab-Tehrany, E.; Akbari, M.; Annabi, N.; Juncker, D.; Khademhosseini, A. Hydrogel Templates for Rapid Manufacturing of Bioactive Fibers and 3D Constructs. Advanced Healthcare Materials 2015, 4 (14), 2146-2153, DOI: 10.1002/adhm.201500492.

(18) Ostrovidov, S.; Salehi, S.; Costantini, M.; Suthiwanich, K.; Ebrahimi, M.; Sadeghian, R. B.; Fujie, T.; Shi, X.; Cannata, S.; Gargioli, C.; Tamayol, A.; Dokmeci, M. R.; Orive, G.; Swieszkowski, W.; Khademhosseini, A. 3D Bioprinting in Skeletal Muscle Tissue Engineering. Small 0 (0), 1805530, DOI: 10.1002/sml1.201805530.

(19) Whitaker, M. J.; Quirk, R. A.; Howdle, S. M.; Shakesheff, K. M. Growth Factor Release from Tissue Engineering Scaffolds. Journal of Pharmacy and Pharmacology 2001, 53 (11), 1427-1437, DOI: 10.1211/0022357011777963.

(20) Farzin, A.; Miri, A. K.; Sharifi, F.; Faramarzi, N.; Jaberi, A.; Mostafavi, A.; Solorzano, R.; Zhang, Y. S.; Annabi, N.; Khademhosseini, A.; Tamayol, A. 3D-Printed Sugar-Based Stents Facilitating Vascular Anastomosis. Advanced Healthcare Materials 2018, 7 (24), 1800702, DOI: 10.1002/adhm.201800702.

(21) Derby, B. Printing and Prototyping of Tissues and Scaffolds. Science 2012, 338 (6109), 921, DOI: 10.1126/science.1226340.
(22) Byambaa, B.; Annabi, N.; Yue, K.; Trujillo-de Santiago, G.; Alvarez, M. M.; Jia, W.; Kazemzadeh-Narbat, M.; Shin, S. R.; Tamayol, A.; Khademhosseini, A. Bioprinted Osteogenic and Vasculogenic Patterns for Engineering 3D Bone Tissue. Advanced Healthcare Materials 2017, 6 (16), 1700015, DOI: 10.1002/adhm.201700015.
(23) Lee, Y.-B.; Polio, S.; Lee, W.; Dai, G.; Menon, L.; Carroll, R. S.; Yoo, S.-S. Bio-printing of collagen and VEGF-releasing fibrin gel scaffolds for neural stem cell culture. Experimental Neurology 2010, 223 (2), 645-652, DOI: https://doi.org/10.1016/j.expneurol.2010.02.014.
(24) Duchi, S.; Onofrillo, C.; O'Connell, C. D.; Blanchard, R.; Augustine, C.; Quigley, A. F.; Kapsa, R. M. I.; Pivonka, P.; Wallace, G.; Di Bella, C.; Choong, P. F. M. Handheld Co-Axial Bioprinting: Application to in situ surgical cartilage repair. Scientific Reports 2017, 7 (1), 5837, DOI: 10.1038/s41598-017-05699-x.
(25) Koffler, J.; Zhu, W.; Qu, X.; Platoshyn, O.; Dulin, J. N.; Brock, J.; Graham, L.; Lu, P.; Sakamoto, J.; Marsala, M.; Chen, S.; Tuszynski, M. H. Biomimetic 3D-printed scaffolds for spinal cord injury repair. Nature Medicine 2019, 25 (2), 263-269, DOI: 10.1038/s41591-018-0296-z.
(26) Kim, S. H.; Yeon, Y. K.; Lee, J. M.; Chao, J. R.; Lee, Y. J.; Seo, Y. B.; Sultan, M. T.; Lee, O. J.; Lee, J. S.; Yoon, S.-i.; Hong, I.-S.; Khang, G.; Lee, S. J.; Yoo, J. J.; Park, C. H. Precisely Printable and Biocompatible Silk Fibroin Bioink for Digital Light Processing 3D Printing. Nature Communications 2018, 9 (1), 1620, DOI: 10.1038/s41467-018-03759-y.
(27) Groll, J.; Burdick, J. A.; Cho, D. W.; Derby, B.; Gelinsky, M.; Heilshorn, S. C.; Jüngst, T.; Malda, J.; Mironov, V. A.; Nakayama, K.; Ovsianikov, A.; Sun, W.; Takeuchi, S.; Yoo, J. J.; Woodfield, T. B. F. A Definition of Bioinks and Their Distinction from Biomaterial Inks. Biofabrication 2018, 11 (1), 013001, DOI: 10.1088/1758-5090/aaec52.
(28) Lee, V. K.; Lanzi, A. M.; Haygan, N.; Yoo, S.-S.; Vincent, P. A.; Dai, G. Generation of Multi-Scale Vascular Network System within 3D Hydrogel using 3D Bio-Printing Technology. Cellular and molecular bioengineering 2014, 7 (3), 460-472, DOI: 10.1007/s12195-014-0340-0.
(29) Hakimi, N.; Cheng, R.; Leng, L.; Sotoudehfar, M.; Ba, P. Q.; Bakhtyar, N.; Amini-Nik, S.; Jeschke, M. G.; Gunther, A. Handheld Skin Printer: In Situ Formation of Planar Biomaterials and Tissues. Lab on a Chip 2018, 18 (10), 1440-1451, DOI: 10.1039/C7LC01236E.
(30) O'Connell, C. D.; Di Bella, C.; Thompson, F.; Augustine, C.; Beirne, S.; Cornock, R.; Richards, C. J.; Chung, J.; Gambhir, S.; Yue, Z.; Bourke, J.; Zhang, B.; Taylor, A.; Quigley, A.; Kapsa, R.; Choong, P.; Wallace, G. G. Development of the Biopen: a handheld device for surgical printing of adipose stem cells at a chondral wound site. Biofabrication 2016, 8 (1), 015019, DOI: 10.1088/1758-5090/8/1/015019.
(31) Albanna, M.; Binder, K. W.; Murphy, S. V.; Kim, J.; Qasem, S. A.; Zhao, W.; Tan, J.; El-Amin, I. B.; Dice, D. D.; Marco, J.; Green, J.; Xu, T.; Skardal, A.; Holmes, J. H.; Jackson, J. D.; Atala, A.; Yoo, J. J. In Situ Bioprinting of Autologous Skin Cells Accelerates Wound Healing of Extensive Excisional Full-Thickness Wounds. Scientific Reports 2019, 9 (1), 1856, DOI: 10.1038/s41598-018-38366-w.
(32) Yue, K.; Trujillo-de Santiago, G.; Alvarez, M. M.; Tamayol, A.; Annabi, N.; Khademhosseini, A. Synthesis, Properties, and Biomedical Applications of Gelatin Methacryloyl (GelMA) Hydrogels. Biomaterials 2015, 73, 254-271, DOI: https://doi.org/10.1016/j.biomaterials.2015.08.045.
(33) Annabi, N.; Rana, D.; Shirzaei Sani, E.; Portillo-Lara, R.; Gifford, J. L.; Fares, M. M.; Mithieux, S. M.; Weiss, A. S. Engineering a Sprayable and Elastic Hydrogel Adhesive with Antimicrobial Properties for Wound Healing. Biomaterials 2017, 139, 229-243, DOI: https://doi.org/10.1016/j.biomaterials.2017.05.011.
(34) Shirzaei Sani, E.; Kheirkhah, A.; Rana, D.; Sun, Z.; Foulsham, W.; Sheikhi, A.; Khademhosseini, A.; Dana, R.; Annabi, N. Sutureless Repair of Corneal Injuries using Naturally Derived Bioadhesive Hydrogels. Science Advances 2019, 5 (3), eaav1281, DOI: 10.1126/sciadv.aav1281.
(35) Ebrahimi, M.; Ostrovidov, S.; Salehi, S.; Kim, S. B.; Bae, H.; Khademhosseini, A. Enhanced Skeletal Muscle Formation on Microfluidic Spun Gelatin Methacryloyl (GelMA) Fibres Using Surface Patterning and Agrin Treatment. Journal of Tissue Engineering and Regenerative Medicine 2018, 12 (11), 2151-2163, DOI: 10.1002/term.2738.
(36) Rezaei Nejad, H.; Goli Malekabadi, Z.; Kazemzadeh Narbat, M.; Annabi, N.; Mostafalu, P.; Tarlan, F.; Zhang, Y. S.; Hoorfar, M.; Tamayol, A.; Khademhosseini, A. Laterally Confined Microfluidic Patterning of Cells for Engineering Spatially Defined Vascularization. Small 2016, 12 (37), 5132-5139, DOI: 10.1002/smll.201601391.
(37) Monteiro, N.; Thrivikraman, G.; Athirasala, A.; Tahayeri, A.; Franca, C. M.; Ferracane, J. L.; Bertassoni, L. E. Photopolymerization of cell-laden gelatin methacryloyl hydrogels using a dental curing light for regenerative dentistry. Dental Materials 2018, 34 (3), 389-399, DOI: https://doi.org/10.1016/j.dental.2017.11.020.
(38) Nichol, J. W.; Koshy, S. T.; Bae, H.; Hwang, C. M.; Yamanlar, S.; Khademhosseini, A. Cell-laden microengineered gelatin methacrylate hydrogels. Biomaterials 2010, 31 (21), 5536-5544, DOI: 10.1016/j.biomaterials.2010.03.064.
(39) Rizwan, M.; Peh, G. S. L.; Ang, H.-P.; Lwin, N. C.; Adnan, K.; Mehta, J. S.; Tan, W. S.; Yim, E. K. F. Sequentially-crosslinked bioactive hydrogels as nano-patterned substrates with customizable stiffness and degradation for corneal tissue engineering applications. Biomaterials 2017, 120, 139-154, DOI: https://doi.org/10.1016/j.biomaterials.2016.12.026.
(40) Haas, C.; Best, T. M.; Wang, Q.; Butterfield, T. A.; Zhao, Y. In Vivo Passive Mechanical Properties of Skeletal Muscle Improve with Massage-like Loading following Eccentric Exercise. Journal of biomechanics 2012, 45 (15), 2630-2636, DOI: 10.1016/j.Thiomech.2012.08.008.
(41) Kot, B. C. W.; Zhang, Z. J.; Lee, A. W. C.; Leung, V. Y. F.; Fu, S. N. Elastic modulus of muscle and tendon with shear wave ultrasound elastography: variations with different technical settings. PloS one 2012, 7 (8), e44348.
(42) Committee, F. (2015) ASTM F2458-05: Test Method for Wound Closure Strength of Tissue Adhesives and Sealants; ASTM International.
(43) Committee, F. (2015) ASTM F2255-05: Test Method for Strength Properties of Tissue Adhesives in Lap-Shear by Tension Loading; ASTM International.
(44) Chen, Y.-C.; Lin, R.-Z.; Qi, H.; Yang, Y.; Bae, H.; Melero-Martin, J. M.; Khademhosseini, A. Functional Human Vascular Network Generated in Photocrosslinkable Gelatin Methacrylate Hydrogels. Advanced Functional Materials 2012, 22 (10), 2027-2039, DOI: 10.1002/adfm.201101662.

(45) Haun, C. T.; Vann, C. G.; Roberts, B. M.; Vigotsky, A. D.; Schoenfeld, B. J.; Roberts, M. D. A Critical Evaluation of the Biological Construct Skeletal Muscle Hypertrophy: Size Matters but So Does the Measurement. Frontiers in physiology 2019, 10, 247-247, DOI: 10.3389/fphys.2019.00247.

(46) Grasman, J. M.; Zayas, M. J.; Page, R. L.; Pins, G. D. Biomimetic scaffolds for regeneration of volumetric muscle loss in skeletal muscle injuries. Acta biomaterialia 2015, 25, 2-15, DOI: 10.1016/j.actbio.2015.07.038.

(47) Wang, L.; Cao, L.; Shansky, J.; Wang, Z.; Mooney, D.; Vandenburgh, H. Minimally Invasive Approach to the Repair of Injured Skeletal Muscle with a Shape-memory Scaffold. Molecular Therapy 2014, 22 (8), 1441-1449.

(48) Eftestol, E.; Egner, I. M.; Lunde, I. G.; Ellefsen, S.; Andersen, T.; Sjåland, C.; Gundersen, K.; Bruusgaard, J. C. Increased Hypertrophic Response with Increased Mechanical Load in Skeletal Muscles Receiving Identical Activity Patterns. American Journal of Physiology-Cell Physiology 2016, 311 (4), C616-C629, DOI: 10.1152/ajpcell.00016.2016.

(49) Sicari, B. M.; Agrawal, V.; Siu, B. F.; Medberry, C. J.; Dearth, C. L.; Turner, N. J.; Badylak, S. F. A Murine Model of Volumetric Muscle Loss and a Regenerative Medicine Approach for Tissue Replacement. Tissue engineering. Part A 2012, 18 (19-20), 1941-1948, DOI: 10.1089/ten.TEA.2012.0475.

(50) Corona B T, Rivera J C, Greising S M. Inflammatory and Physiological Consequences of Debridement of Fibrous Tissue after Volumetric Muscle Loss Injury. Clinical and Translational Science. 2018; 11(2):208-17. doi: doi:10.1111/cts.12519.

(51) Sicari B M, Rubin J P, Dearth C L, Wolf M T, Ambrosio F, Boninger M, Turner N J, Weber D J, Simpson T W, Wyse A. An acellular biologic scaffold promotes skeletal muscle formation in mice and humans with volumetric muscle loss. Science translational medicine. 2014; 6(234):234ra58-ra58.

(52) Kang H-W, Lee S J, Ko I K, Kengla C, Yoo J J, Atala A. A 3D bioprinting system to produce human-scale tissue constructs with structural integrity. Nature biotechnology. 2016; 34(3):312.

(53) Murphy S V, Atala A. 3D bioprinting of tissues and organs. Nature biotechnology. 2014; 32(8):773.

(54) Wu S, Duan B, Qin X, Butcher J T. Living nano-micro fibrous woven fabric/hydrogel composite scaffolds for heart valve engineering. Acta Biomaterialia. 2017; 51:89-100. doi: https://doi.org/10.1016/j.actbio.2017.01.051.

(55) Akbari M, Tamayol A, Laforte V, Annabi N, Najafabadi A H, Khademhosseini A, Juncker D. Composite Living Fibers for Creating Tissue Constructs Using Textile Techniques. Advanced Functional Materials. 2014; 24(26): 4060-7. doi: doi:10.1002/adfm.201303655.

In this disclosure, references to the above sources, which are numbered in single parentheses "( )", are made using the corresponding number in the single parentheses, in the same manner as those sources are listed as references, above.

What is claimed is:

1. A bioprinter device, comprising:
a housing defining: a proximal end, and a distal end opposite the proximal end,
the housing including a receptacle for receiving at least a portion of a syringe assembly within the housing, the receptacle defining:
a first opening, and a second opening, through a wall of the housing,
the first opening positioned distally from the second opening to facilitate a removable insertion of at least the portion of the syringe assembly into the receptacle through the first opening, and
the second opening positioned at, or proximal to, the proximal end to facilitate access to a nozzle of the syringe assembly from an exterior of the housing through the second opening upon the removable insertion of at least the portion of the syringe assembly into the receptacle;
a power supply disposed within the housing;
an electric actuator disposed within the housing at a position sufficient to facilitate an operable coupling of the electric actuator to at least a portion of a plunger of the syringe assembly upon an insertion into the receptacle;
a control interface positioned at least partially within the housing and including at least one control device operable from the exterior of the housing; and
a controller disposed within the housing and coupled to: the power supply, the electric actuator, and the control interface,
the controller configured to regulate a flow of power from the power supply to the electric actuator based on signals received from the at least one control device, to facilitate regulating an actuation of the plunger by the electric actuator.

2. The device of claim 1 further comprising a light source configured to direct light proximally from the proximal end.

3. The device of claim 1 further comprising an imaging device configured to generate one or more videos and/or one or more images of the exterior of the housing including a space positioned proximal to the proximal end.

4. The device of claim 3 further comprising a transmitter configured to transmit the one or more videos and/or the one or more images to a receiver positioned remote from the device.

5. The device of claim 1, wherein the at least one control device includes: a first control device, and a second control device,
the first control device configured to cause the controller to alternately increase and decrease an actuation rate of the electric actuator; and
the second control device configured to cause the controller to alternately maintain and change an actuation direction of the electric actuator.

6. The device of claim 1 further comprising a bioprinter kit, the kit including:
at least one syringe assembly having a barrel at least partially filled with a liquid; and
a temperature regulation means for maintaining the liquid in the barrel at or near a constant temperature.

7. The device of claim 6, wherein the temperature regulation means include a pump that is configured to direct a flow of heated fluid or cooled fluid to maintain the liquid in the barrel at or near the constant temperature.

8. The device of claim 1, wherein the electric actuator includes a stepper motor, a direct current (DC) motor, a linear actuator, or a pneumatic actuator.

9. A bioprinter system, comprising:
a housing defining: a proximal end, and a distal end opposite the proximal end,
the housing including a receptacle, the receptacle defining:
a first opening, a second opening, through a wall of the housing,
the first opening positioned distally from the second opening to facilitate access to a syringe assembly from an exterior of the housing, and
the second opening positioned at, or proximal to, the proximal end to facilitate access to a nozzle from the exterior of the housing through the second opening, and a flow of liquid from a barrel through the nozzle to the exterior of the housing;
the syringe assembly positioned at least partially in the receptacle and including: the barrel for containing the liquid, the nozzle in flow communication with the barrel, and a plunger slidably disposed inside the barrel;
a power supply disposed within the housing;
an electric actuator disposed within the housing and operably coupled to at least a portion of the plunger;
a control interface positioned at least partially within the housing and including at least one control device operable from the exterior of the housing; and
a controller disposed within the housing and coupled to: the power supply, the electric actuator, and the control interface,
the controller configured to regulate an actuation of the plunger by the electric actuator by regulating a flow of power from the power supply to the electric actuator based on signals received from the at least one control device, to facilitate regulating a flow of the liquid from the barrel through the nozzle and to the exterior of the housing.

10. The system of claim 9 further comprising a temperature regulation device disposed within the housing and configured to maintain the liquid at or near a constant temperature in barrel.

11. The system of claim 9 further comprising an elongate tip in flow communication with the nozzle and having: a distal end coupled to the nozzle, and a proximal end extending proximally from the nozzle.

12. The system of claim 11, the proximal end of the tip having a diameter of between 100 and 1000 microns.

13. The system of claim 9, the controller further configured to pause extrusion of the liquid for a predetermined duration.

14. The system of claim 9, wherein the liquid includes a hydrogel formulation, the hydrogel formulation including at least one of drugs, nanoparticles, microparticles, conductive materials, bioceramic, or polymeric particles.

* * * * *